US012026770B2

(12) United States Patent
Nicholson et al.

(10) Patent No.: US 12,026,770 B2
(45) Date of Patent: *Jul. 2, 2024

(54) FINANCIAL HEALTH SMARTWATCH

(71) Applicant: Bank of America Corporation, Charlotte, NC (US)

(72) Inventors: Daralyn M. Nicholson, Charlotte, NC (US); Anna Hollifield, Charlotte, NC (US); Shaun G. Hunter, Grayson, GA (US)

(73) Assignee: Bank of America Corporation, Charlotte, NC (US)

( * ) Notice: Subject to any disclaimer, the term of this patent is extended or adjusted under 35 U.S.C. 154(b) by 850 days.

This patent is subject to a terminal disclaimer.

(21) Appl. No.: 17/065,636

(22) Filed: Oct. 8, 2020

(65) Prior Publication Data

US 2021/0027366 A1  Jan. 28, 2021

Related U.S. Application Data

(63) Continuation of application No. 16/212,201, filed on Dec. 6, 2018, now Pat. No. 10,817,933, and a
(Continued)

(51) Int. Cl.
*G06Q 20/00* (2012.01)
*G06Q 20/32* (2012.01)
(Continued)

(52) U.S. Cl.
CPC ......... *G06Q 40/02* (2013.01); *G06Q 20/3223* (2013.01); *G06Q 20/4014* (2013.01);
(Continued)

(58) Field of Classification Search
CPC . G06Q 40/02; G06Q 20/3223; G06Q 20/4014
(Continued)

(56) References Cited

U.S. PATENT DOCUMENTS 4,750,119 A   6/1988  Cohen et al.
4,823,264 A   4/1989  Deming
(Continued)

FOREIGN PATENT DOCUMENTS

JP    200350916   2/2003
WO    9314476 A1  7/1993
(Continued)

OTHER PUBLICATIONS

Dec. 15, 2021—U.S. Office Action—U.S. Appl. No. 16/817,785.
(Continued)

*Primary Examiner* — Rokib Masud
(74) *Attorney, Agent, or Firm* — Banner & Witcoff, Ltd.

(57) ABSTRACT

Computer implemented systems and methods are disclosed involving technological advancements in the processing of electronic transaction processing. A system may comprise a networked environment including heterogeneous or homogenous payment processing systems. A centrally accessible server machine storing an automatic savings program module and rules controls the generation and dissemination of new transactions derived from incoming transactions. Moreover, the networked system may be used to control authorization of electronic transactions in a near real-time manner. The networked system may be used to distribute a financial health of a user in a user-friendly, mobile form factor.

17 Claims, 29 Drawing Sheets

Related U.S. Application Data continuation-in-part of application No. 16/212,400, filed on Dec. 6, 2018, now Pat. No. 10,817,880, and a continuation-in-part of application No. 16/212,332, filed on Dec. 6, 2018, now Pat. No. 10,817,934, said application No. 16/212,201 is a continuation-in-part of application No. 14/844,875, filed on Sep. 3, 2015, now Pat. No. 10,169,749, said application No. 16/212,400 is a continuation-in-part of application No. 14/844,875, filed on Sep. 3, 2015, now Pat. No. 10,169,749, said application No. 16/212,332 is a continuation-in-part of application No. 14/844,875, filed on Sep. 3, 2015, now Pat. No. 10,169,749.

(51) Int. Cl.
*G06Q 20/40* (2012.01)
*G06Q 40/02* (2023.01)
*G16H 10/00* (2018.01)
*H04B 1/3827* (2015.01)

(52) U.S. Cl.
CPC ........... *G06Q 20/405* (2013.01); *G16H 10/00* (2018.01); *H04B 1/385* (2013.01)

(58) Field of Classification Search
USPC .......................................................... 705/16
See application file for complete search history.

(56) References Cited

U.S. PATENT DOCUMENTS

| | | | |
|---|---|---|---|
| 4,941,090 A | 7/1990 | McCarthy | |
| 5,056,019 A | 10/1991 | Schultz et al. | |
| 5,200,889 A | 4/1993 | Mori | |
| 5,287,268 A | 2/1994 | McCarthy | |
| 5,302,811 A | 4/1994 | Fukatsu | |
| 5,466,919 A | 11/1995 | Hovakimian | |
| 5,471,669 A | 11/1995 | Lidman | |
| 5,621,640 A | 4/1997 | Burke | |
| 5,787,404 A | 7/1998 | Fernandez-Holmann | |
| 5,970,480 A | 10/1999 | Kalina | |
| 5,987,429 A * | 11/1999 | Maritzen ............... G06Q 40/123 705/400 |
| 6,036,344 A | 3/2000 | Goldenberg | |
| 6,049,778 A | 4/2000 | Walker et al. | |
| 6,088,682 A | 7/2000 | Burke | |
| 6,112,191 A | 8/2000 | Burke | |
| 6,119,099 A | 9/2000 | Walker et al. | |
| 6,164,533 A | 12/2000 | Barton | |
| 6,267,670 B1 | 7/2001 | Walker et al. | |
| 6,298,329 B1 | 10/2001 | Walker et al. | |
| 6,381,590 B1 | 4/2002 | Debois | |
| 6,581,041 B1 | 6/2003 | Canney | |
| 6,598,024 B1 | 7/2003 | Walker et al. | |
| 6,631,358 B1 | 10/2003 | Ogilvie | |
| 6,965,868 B1 | 11/2005 | Bednarek | |
| 7,072,851 B1 | 7/2006 | Wilcox et al. | |
| 7,090,138 B2 | 8/2006 | Rettenmyer et al. | |
| 7,392,224 B1 | 6/2008 | Bauer et al. | |
| 7,398,226 B2 | 7/2008 | Haines et al. | |
| 7,597,255 B2 | 10/2009 | Deane et al. | |
| 7,753,261 B2 | 7/2010 | Rosenblatt et al. | |
| 7,797,208 B2 | 9/2010 | Thomas | |
| 8,301,530 B2 | 10/2012 | Carretta et al. | |
| 8,401,936 B2 * | 3/2013 | Penning ............... G06Q 40/02 705/40 |
| 8,407,137 B2 | 3/2013 | Thomas | |
| 8,416,924 B1 | 4/2013 | Barth et al. | |
| 8,635,137 B2 | 1/2014 | Carretta et al. | |
| 8,738,429 B2 | 5/2014 | Shepard | |
| 9,495,703 B1 | 11/2016 | Kaye, III | |
| 9,734,536 B2 | 8/2017 | Cruttenden et al. | |
| 2002/0046124 A1 | 4/2002 | Alderucci et al. | |
| 2002/0120513 A1 | 8/2002 | Webb et al. | |
| 2002/0161630 A1 | 10/2002 | Kern et al. | |
| 2002/0188533 A1 | 12/2002 | Sanchez et al. | |
| 2003/0009379 A1 | 1/2003 | Narasimhan et al. | |
| 2003/0061097 A1 | 3/2003 | Walker et al. | |
| 2003/0064788 A1 | 4/2003 | Walker et al. | |
| 2003/0101131 A1 | 5/2003 | Warren et al. | |
| 2003/0149629 A1 | 8/2003 | Claridge et al. | |
| 2003/0200163 A1 | 10/2003 | O'Riordan et al. | |
| 2003/0208439 A1 | 11/2003 | Rast | |
| 2003/0233317 A1 | 12/2003 | Judd | |
| 2003/0236712 A1 | 12/2003 | Antonucci et al. | |
| 2004/0039645 A1 | 2/2004 | Walker et al. | |
| 2004/0054593 A1 | 3/2004 | Van Luchen | |
| 2004/0153400 A1 | 8/2004 | Burke | |
| 2004/0193497 A1 | 9/2004 | Tanaka | |
| 2004/0222285 A1 | 11/2004 | Pohl | |
| 2005/0004867 A1 * | 1/2005 | Spector ............... G06Q 20/00 705/38 |
| 2005/0021353 A1 | 1/2005 | Aviles et al. | |
| 2005/0021363 A1 | 1/2005 | Stimson et al. | |
| 2005/0097034 A1 | 5/2005 | Loeger et al. | |
| 2005/0133590 A1 | 6/2005 | Rettenmyer et al. | |
| 2005/0251440 A1 | 11/2005 | Bednarek | |
| 2006/0047589 A1 | 3/2006 | Grau | |
| 2007/0033134 A1 | 2/2007 | Carretta et al. | |
| 2007/0094130 A1 | 4/2007 | Burke | |
| 2007/0124203 A1 | 5/2007 | Popescu et al. | |
| 2008/0103968 A1 | 5/2008 | Bies et al. | |
| 2009/0063332 A1 * | 3/2009 | Tabaczynski .......... G06Q 30/02 705/39 |
| 2009/0222358 A1 | 9/2009 | Bednarek | |
| 2010/0076776 A1 * | 3/2010 | Kopko ............... G06Q 30/0218 705/14.1 |
| 2011/0004546 A1 | 1/2011 | Thomas | |
| 2012/0072345 A1 | 3/2012 | Solomon et al. | |
| 2012/0197794 A1 | 8/2012 | Grigg et al. | |
| 2013/0030992 A1 | 1/2013 | Carretta et al. | |
| 2013/0231994 A1 | 9/2013 | Antonucci | |
| 2014/0006275 A1 | 1/2014 | Hanson et al. | |
| 2014/0012691 A1 | 1/2014 | Hanson et al. | |
| 2014/0222636 A1 * | 8/2014 | Cheng ............... G06Q 30/0201 705/35 |
| 2014/0337150 A1 | 11/2014 | Anand | |
| 2015/0081458 A1 | 3/2015 | Cruttenden et al. | |
| 2015/0193866 A1 * | 7/2015 | Van Heerden ......... G06Q 40/02 705/35 |
| 2015/0193867 A1 * | 7/2015 | Del Vecchio .......... G06Q 40/02 705/39 |
| 2015/0230045 A1 | 8/2015 | Johnson et al. | |
| 2016/0042340 A1 | 2/2016 | Burke et al. | |
| 2016/0321663 A1 | 11/2016 | Batlle | |

FOREIGN PATENT DOCUMENTS

| | | |
|---|---|---|
| WO | 03030054 A1 | 4/2003 |
| WO | 2007016697 A2 | 2/2007 |
| WO | 2008111965 A2 | 9/2008 |

OTHER PUBLICATIONS

Google Scholar NPL (non-patent literature) Search Results, dated Dec. 11, 2021. (Year: 2021).
Aug. 2, 2005—(US)—Related U.S. Appl. No. 11/161,418.
Aug. 17, 2007 (WO) International Search Report, PCT/US 06/30362, 6 pages.
Feb. 6, 2007—(PCT)—Related Application No. PCT/US07/61694.
Feb. 8, 2008—(US)—Related U.S. Appl. No. 61/027,397.
Jan. 2008—Option1 Credit Union, Options News About Opportunity, 5 pages.
Feb. 9, 2009—(US)—Related U.S. Appl. No. 12/368,034.
Sep. 4, 2009—(US)—Related U.S. Appl. No. 12/554,616.
Jul. 30, 2010—Supplementary European Search Report, PCT/US2006030362, 5 pages.
Mar. 24, 2010—(US)—Related U.S. Appl. No. 12/730,394.
Aug. 8, 2011 (CN) Second Office Action, Application No. 200780050996.5, 6 pages.

(56) References Cited

OTHER PUBLICATIONS

Dec. 13, 2011 (EP)—Office Action—Application No. Patent No. 0689359.4-221/1915731, 18 pages.
Jul. 14, 2011 (EP) Communication from European Patent Office, Application No. 06 789 359.4 0 2221, 5 pages.
Jun. 14, 2011—(PCT) Response to Office Action—Application PCT/US2006/030362, 11 pages.
Nov. 24, 2011—(PCT) Response to Office Action—PCT Application PCT/US2006/030362, 4 pages.
Apr. 27, 2012—(US) File History—U.S. Appl. No. 11/161,418, filed Aug. 2, 2005.
Nov. 27, 2012—U.S. Non-Final Office Action—U.S. Appl. No. 13/613,433.
Sep. 7, 2012—(US) File History for U.S. Appl. No. 12/554,616, filed Sep. 4, 2009.
Sep. 24, 2012 U.S. Notice of Allowance and Fee(s) Due, U.S. Appl. No. 12/554,935, 10 pages.
Sep. 7, 2012—(US) File History for U.S. Appl. No. 12/368,034, filed Feb. 9, 2009.
Aug. 28, 2013—U.S. Advisory Action—U.S. Appl. No. 12/730,394.
Dec. 17, 2013—(US)—Related U.S. Appl. No. 14/109,269.
Apr. 5, 2017—U.S. Office Action—U.S. Appl. No. 14/109,269.
Dec. 20, 2017—U.S. Office Action—U.S. Appl. No. 14/844,884.
Mar. 27, 2017—U.S. Office Action—U.S. Appl. No. 14/551,930.
Nov. 27, 2017—U.S. Office Action—U.S. Appl. No. 14/850,593.
Apr. 23, 2018—U.S. Office Action—U.S. Appl. No. 14/844,880.
Jan. 8, 2018—U.S. Office Action—U.S. Appl. No. 14/844,880.
Jan. 10, 2018—U.S. Office Action—U.S. Appl. No. 14/844,896.
Jan. 18, 2018—U.S. Office Action—U.S. Appl. No. 14/844,875.
Jan. 18, 2018—U.S. Office Action—U.S. Appl. No. 14/844,887.
Jul. 27, 2018—U.S. Office Action—U.S. Appl. No. 14/844,896.
May 21, 2018—U.S. Office Action—U.S. Appl. No. 14/850,593.
Sep. 7, 2018—U.S. Office Action—U.S. Appl. No. 14/551,930.
Banco Popular Ahorro Directo, <http://www.popular.com/ahorrodirectto/index-en.html>, downloaded Mar. 11, 2008, 3 pages.
Bank of America offers a new way to save, dated Oct. 4, 2005, www.msnbc.msn.com/id/9593071/#.UL463-SCmSo, 2 pages.
Bank of America's Twist on Debit Card Rewards, dated Oct. 6, 2005, www.depositaccounts.com/blog/2005/10/bank-of-americas-twist-on-debit-card-html, 1 page.
Bank of America's Unusual Automated Savings Plan by Jim Bruene, dated Oct. 5, 2005, © 1995-2010, Financial Insite, Inc., 2 pages.
Bank the Rest® savings program, Spend and Save. Together at last, <http://www.scotiabank.com/BankTheRest>, downloaded Jan. 25, 2012, 1 page.
Best Bets Financial Services, Premier Bank, <http://www.connectmidmissouri.com/directory/financial/premium.aspx>?id=1761644, downloaded Jan. 25, 2012, 4 pages.
Electronic Payments Primer, National Electronic Commerce Coordinating Counsel, Oct. 2002, http://www85.homepage.villanova.edu/timothy.ay/MIS3030/epayments_primer.pdf, 40 pages.
*Every Penny Counts, Inc.* v. *Bank of America Corporation and Bank of America*, N.A., Memorandum and Order, U.S. District Court, Middle District of Florida, Fort Meyers Division, Case No. 2:07-cv-042, dated May 27, 2009, 6 pages.
*Every Penny Counts, Inc.* v. *Bank of America Corporation and Bank of America*, N.A.; Opinion and Order, U.S. District Court, Middle District of Florida, Fort Meyers Division, Case No. 2:07-cv-04-FtM-29SPC, dated Sep. 29, 2008, 16 pages.
File History for U.S. Appl. No. 12/730,394, filed Mar. 24, 2010.
Finance, <http://www.fatwallet.com/t/52/799201/>, 11 pages, downloaded Jan. 11, 2008.
Fowler, G.A., These Apps Can Finally Get you to Save Money, <http://www.wsj.com/articles/these-apps-can-finally-get-you-to-save-money-1434477296?mod=djemptech_t>, printed Oct. 6, 2015; 5 pages.
Introducing Free Checking with Extra Savings on top, Savings just got a whole lot easier, Capital One Bank, Baton Rouge Advocate, Oct. 28, 2009, 1 page.
North Carolina Bank and Trust, Round Up to Save, https:/www.ncbtonline.com/productsandservices/personal/ <http://www.ncbtonline.com/productsandservices/personal/> rounduptosave.aspx, downloaded Jan. 25, 2012, 2 pages.
Option1 Credit Union Spare Change Debit Card Savings Program, <http://www.option1cu.org/about-bell-com/news.html>, downloaded Feb. 3, 2008, 2 pages.
Round It Up America®, Round up. Donate Change, Make a Difference, Support Round It Up America® today!, http://www.rounditupamerica.org/donate-online.php <http://www.rounditupamerica.org/donate-online.php>, downloaded Jan. 25, 2012, 2 pages.
Round It Up America®, Round up. Donate Change, Make a Difference. Recent News, <http://www/rounditupaemrica>.org, downloaded Jan. 25, 2012, 3 pages.
Round it Up America®, Round Up. Donate Change. Make a Difference, <http://www.rounditupamerica.org>, downloaded Nov. 8, 2010, 2 pages.
Text of First Office Action, PCT Application No. 20078005099965, Undated, 3 pages.
Wachovia Introduces New Product That Makes Saving Easy and Automatic for Consumers, http://www.wachovia.com/> inside/page/printer/0,,134_307% E1701.00.html, 3 pages, dated Jan. 11, 2008.
Wachovia offers customers Way2Save, <http://www.charlotte.com/businessA/-print/story/441323.html>, 1 page, downloaded Jan. 11, 2008.
Wachovia offers new savings incentive that offers deposit match, <http://www.timesanddemocrat.com/> articles/2008/01/11 /business/doc478, 2 pages, downloaded Jan. 11, 2008.
Wachovia Personal Finance FAQs, Way2Save Account, http://111 . wachovia.com/personal/page/ printer/0J,657_2167% 5E12663, downloaded Mar. 11, 2008, 3 pages.
Wachovia Way2Save(SM) Account Agreement, http://www.wachovia.com/misc/0, 1756,00.html, 2 <http://www.wachovia.com/misc/0%ef%bc%8c, 1756,00.html%ef%bc%8c2>, 3 pages, downloaded Jan. 18, 2008.
Wachovia's Way2Save Savings Account, with scans, <http://bankdesign.com/boardA12618.html>, 3 pages, downloaded Jan. 11, 2008.
Wachovia, My Arch-Nemesis Bank, Offers Very Tempting 5% Plus Bonus Savings Account Deal, <http://www.punny>.org/money/wachovia-my-arch-nemesis-bank-offers-v, 7 pages, downloaded Jan. 11, 2008.
Way2save, Turn Everyday Banking Into Automatic Savings brochure, © 2008, Wachovia Corporation, 6 pages.
Who Says You Can't Afford to Save? Bank on it: Spare Change Can Add Up Fast (Third Edition), Jaffe, C.A., Mar. 5, 2000 © 2012 ProQuest LLC, 3 pages.
Wolfe, Daniel, "Wachovia Links Savings, Debit to Land Customers," American Banker, vol. 173?issue 9, Jan. 14, 2008, 3 pages.
May 14, 2019—U.S. Office Action—U.S. Appl. No. 14/551,930.
Dec. 2, 2019—(US) Patent Board Decision—Examiner Reversed U.S. Appl. No. 14/109,269.

\* cited by examiner

Figure 17

| Criteria | Action | Mandatory/Optional |
|---|---|---|
| Merchant Identifier | Round up to next whole dollar amount | Mandatory |
| Location (GPS) | Round up to next whole dollar amount | Optional |
| Dollar Amount | Match coupon savings | Mandatory |
| Date (Day of Week) | Add predetermined additional amount | Optional |
| | | |
| | | |
| | | |

Figure 25

FINANCIAL HEALTH SMARTWATCH

CROSS-REFERENCE TO RELATED APPLICATIONS

This application is a continuation of application Ser. No. 16/212,201 (filed on Dec. 6, 2018), which is a Continuation-in-part of application Ser. No. 14/844,875 (which corresponds to U.S. Pat. No. 10,169,749 issued Jan. 1, 2019 filed on Sep. 3, 2015). In addition, this Applications is a Continuation-in-part of application Ser. No. 16/212,332 (filed on Dec. 6, 2018), which is a Continuation-in-part of application Ser. No. 14/844,875 filed on Sep. 3, 2015. In addition, this Applications is a Continuation-in-part of application Ser. No. 16/212,400 (filed on Dec. 6, 2018), which is a Continuation-in-part of application Ser. No. 14/844,875 filed on Sep. 3, 2015. All of the aforementioned applications in this paragraph are herein incorporated by reference in their entireties.

TECHNICAL FIELD

Computer implemented systems and methods are disclosed involving technological advancements in the processing of electronic transaction processing. A system may comprise a networked environment including heterogeneous or homogenous payment processing systems. Moreover, the networked system may be used to control authorization of electronic transactions in a near real-time manner. The networked system may be used to distribute a financial health of a user in a user-friendly, mobile form factor.

BACKGROUND

Consumers sometimes feel that saving money is difficult. Those who earn less or are supporting a family may find it particularly challenging to put money away for emergencies, a child's education, or a special purchase. Even affluent consumers sometimes feel that they should save more money. A consumer can save funds in a bank account by making deposits into the account or by transferring funds from another account. In addition, grandparents or other relatives or friends sometimes desire to contribute money to somebody else's (e.g., a grandchild's) savings account. Nevertheless, there remains room for technological improvements in systems and methods for automatically facilitating and/or encouraging savings.

BRIEF SUMMARY

The following presents a simplified summary of the disclosure in order to provide a basic understanding of some aspects. It is not intended to identify key or critical elements of the invention or to delineate the scope of the invention. The following summary merely presents some concepts of the disclosure in a simplified form as a prelude to the more detailed description provided below.

Computer implemented systems and methods are disclosed involving technological advancements in the processing of electronic transaction processing. A system may comprise a networked environment including heterogeneous or homogenous payment processing systems. A centrally accessible server machine storing an automatic savings program module and rules controls the generation and dissemination of new transactions derived from incoming transactions. Moreover, the networked system may be used to control authorization of electronic transactions in a near real-time manner. The networked system may be used to distribute a financial health of a user in a user-friendly, mobile form factor.

A computer implemented system and method are disclosed of processing a financial transaction that includes determining an automatic savings amount and rewards amount payments. The system may comprises a checking account, a savings account, an account of a merchant, and one or more computer systems including a communication interface, processor, and memory storing computer-executable instructions. The rewards amount may be calculated based on various techniques.

Aspects of the disclosure generally relate to automated funds transfer and bonus payments associated with an account.

BRIEF DESCRIPTION OF THE DRAWINGS

The present disclosure is illustrated by way of example and not limited in the accompanying figures in which like reference numerals indicate similar elements and in which:

FIG. 17 depicts an example savings message type packet in accordance with aspects of the disclosure.

FIG. 25 shows one example of an illustrative portion of an automated saving table stored in computer memory accessible to a central server computer.

DETAILED DESCRIPTION

Figure 1:
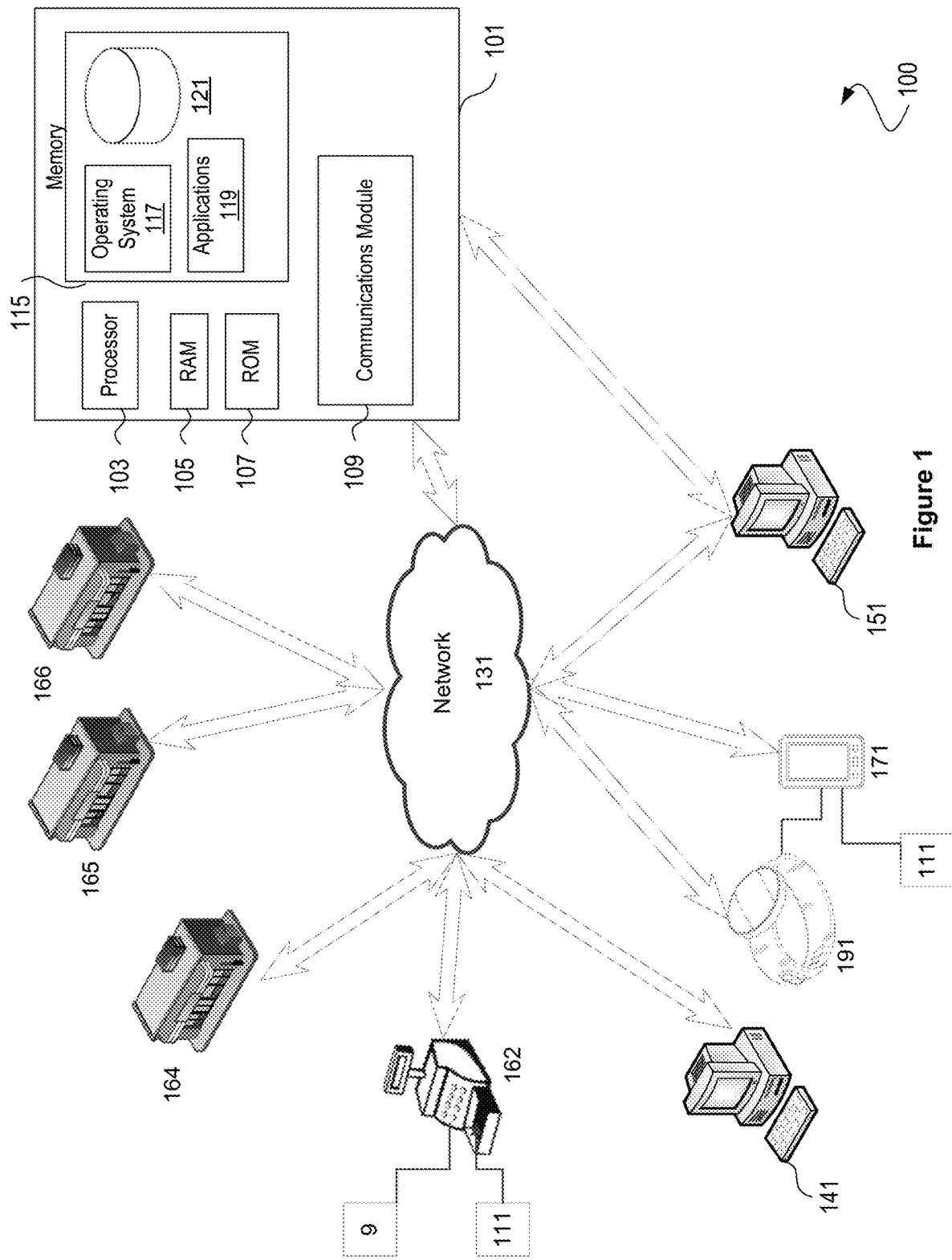
FIG. 1 shows an illustrative operating environment in which various aspects of the disclosure may be implemented.

Aspects of the disclosure generally relate to an innovative network architecture that enables the seamless connectivity of an automated savings program to an existing network of transactional systems. In one embodiment, the transactional system may comprise a plurality of homogenous computer systems belonging to a single entity. In other embodiments, the transactional system may comprise heterogeneous computer systems belonging to a plurality of entities. The seamless connectivity may permit universal sign-on and/or enrollment to an automatic savings program. The connectivity is seamless, in some embodiments, because an existing transactional system might not natively include an automatic savings program, but the innovative network architecture enables a computer server configured with an automatic savings program to interface with the existing transactional system. In one embodiment, the interface may be through a web service that integrates into an existing network of transactional system. In another embodiment, the interface may be through overloading of method calls of objects in an existing transactional system.

The transactional systems may comprise a debit network, a credit network, an online billpay network, a person-to-person payment network, a digital wallet, a cypto-currency network, and/or any other payment network. Moreover, the networked system may be used to control authorization of electronic transactions in a near real-time manner. The networked system may be used to distribute a financial health of a user in a user-friendly, mobile form factor.

In accordance with various aspects of the disclosure, a method and system for enhanced automatic savings is disclosed. In one embodiment, computer implemented systems and methods are disclosed for processing a financial transaction that may include determining an automatic savings amount, providing notifications of savings updates, and providing payments as a reward for savings. The system includes computing systems that operate to process transactions associated with various types of accounts. Examples of such accounts may include a checking account, a savings account, a merchant account, and investment account, and one or more computer systems and mobile devices including a communication interface, processor, memory storing computer-executable instructions, and savings modules. The system further includes computing systems that operate to determine reward amounts based on automatic savings. The rewards amount may be calculated based on various techniques.

In one embodiment, a computer implemented savings program automatically generates a monetary amount (e.g., a savings amount) from each financial transaction by a user of a bank or other financial institution and deposits the savings amount in the user's or somebody else's savings account; thus the user can accumulate savings conveniently and painlessly. In addition, automated loan payments, and automated contributions to charitable and charitable-like (e.g., environmental funds) organizations may be made in a similar fashion.

In another embodiment, a computer implemented savings program automatically generates a savings amount from each financial transaction by a user of a bank or other financial institution, determines when a level of savings is reached, notifies a user of the savings amount, and provides an interface presenting input elements for the user to select where the savings amount should be deposited.

In one embodiment, a computer implemented savings program automatically generates a savings amount from each financial transaction by a user of a bank or other financial institution. In addition, the savings program monitors the user's saving progress and may present the user with an option to add additional savings which are deposited in the user's or somebody else's savings account.

In another embodiment, a computer implemented savings program automatically generates a savings amount from each financial transaction by a user of a bank or other financial institution and notifies a user as to the user's progress towards a saving goal once a level of savings is reached or a certain time period has elapsed.

In another embodiment, a computer implemented savings program automatically generates a savings amount from each financial transaction by a user of a bank or other financial institution based on comparable transaction amounts for matched products or merchants.

In another embodiment, a computer implemented savings program automatically generates a savings amount from each financial transaction by a user of a bank or other financial institution based on discounts provided by merchants.

In one embodiment, a computer implemented savings program automatically generates a savings amount from each financial transaction by a user of a bank or other financial institution. In addition, the savings program monitors the user's saving progress and adjusts the automatic saving methods to keep the user on track to reach their savings goal.

FIG. 1 illustrates an example of a suitable computing system environment 100 that may be used according to one or more illustrative embodiments of the disclosure. The computing system environment 100 is only one example of a suitable computing environment and is not intended to suggest any limitation as to the scope of use or functionality of the disclosure. The computing system environment 100 should not be interpreted as having any dependency or requirement relating to any one or combination of components illustrated in the exemplary computing system environment 100.

The disclosure is operational with numerous computing system environments or configurations. Examples of computing systems, environments, and/or configurations that may be suitable for use with the disclosure include, but are not limited to, personal computers, server computers, handheld or laptop devices, multiprocessor systems, microprocessor-based systems, set top boxes, programmable consumer electronics, network PCs, minicomputers, mainframe computers, distributed computing environments that include any of the above systems or devices, and the like that have been programmed with particular instructions to carry out one or more of the functional aspects described in further detail below either individually or in conjunction with one another.

The disclosure may be described in the general context of computer-executable instructions, such as program modules, being executed by a computer. Generally, program modules include routines, programs, objects, components, data structures, and the like that perform particular tasks or implement particular abstract data types. The disclosure may also be practiced in distributed computing environments where tasks are performed by remote processing devices that are linked through a communications network. In a distributed computing environment, program modules may be located in both local and remote computer storage media including memory storage devices.

Figure 4:
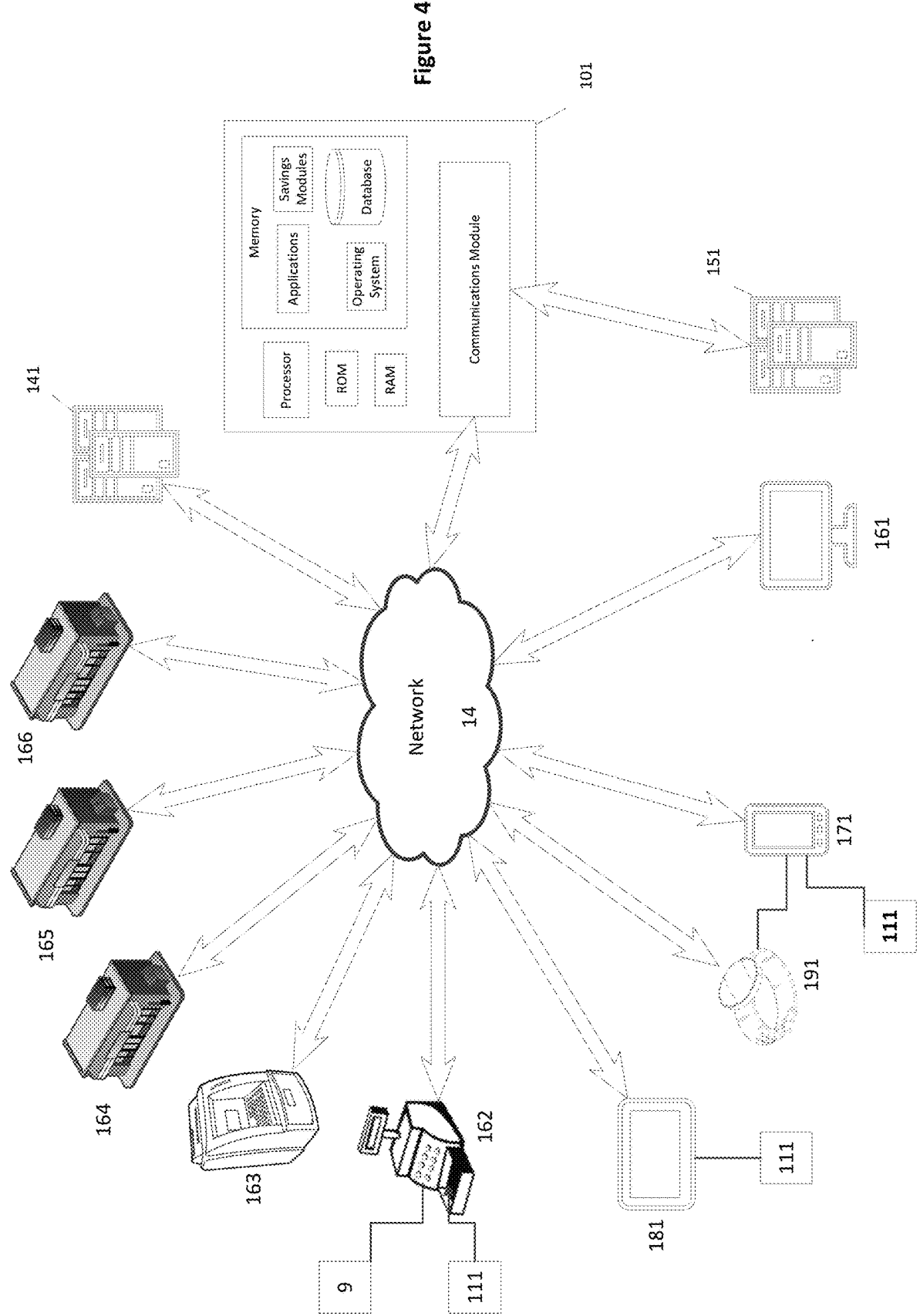
FIG. 4 shows an illustrative operating environment in which various aspects of the disclosure may be implemented.

With reference to FIG. 1 and FIG. 4, computer implemented systems for processing enhanced automatic savings are shown. The computing system environment 100 may include a computing device 101 having a processor 103 for controlling overall operation of the computing device 101 and its associated components, including RAM 105, ROM 107, communications module 109, and memory 115. Computing device 101 typically includes a variety of computer readable media. Computer readable media may be any available media that may be accessed by computing device 101 and include both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, random access memory (RAM), read only memory (ROM), electronically erasable programmable read only memory (EEPROM), flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by computing device 101. Communication media typically embodies computer readable instructions, data structures, program modules or other data in a modulated data signal such as a carrier wave or other transport mechanism and includes any information delivery media. Modulated data signal is a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media. Although not shown, RAM 105 may include one or more are applications representing the application data stored in RAM memory 105 while the computing device is on and corresponding software applications (e.g., software tasks), are running on the computing device 101.

With reference to FIG. 1 and FIG. 4, communications module 109 may include a microphone, keypad, touch screen, and/or stylus through which a user of computing device 101 may provide input, and may also include one or more of a speaker for providing audio output and a video display device for providing textual, audiovisual and/or graphical output. Software may be stored within memory 115 and/or storage to provide instructions to processor 103 for enabling computing device 101 to perform various functions. For example, memory 115 may store software used by the computing device 101, such as an operating system 117, application programs 119, and an associated database 121. Alternatively, some or all of the computer executable instructions for computing device 101 may be embodied in hardware or firmware (not shown). As described in detail below, the database 121 may provide centralized storage of account information and account holder information for the entire business, allowing interoperability between different elements of the business residing at different physical locations.

Figure 5:
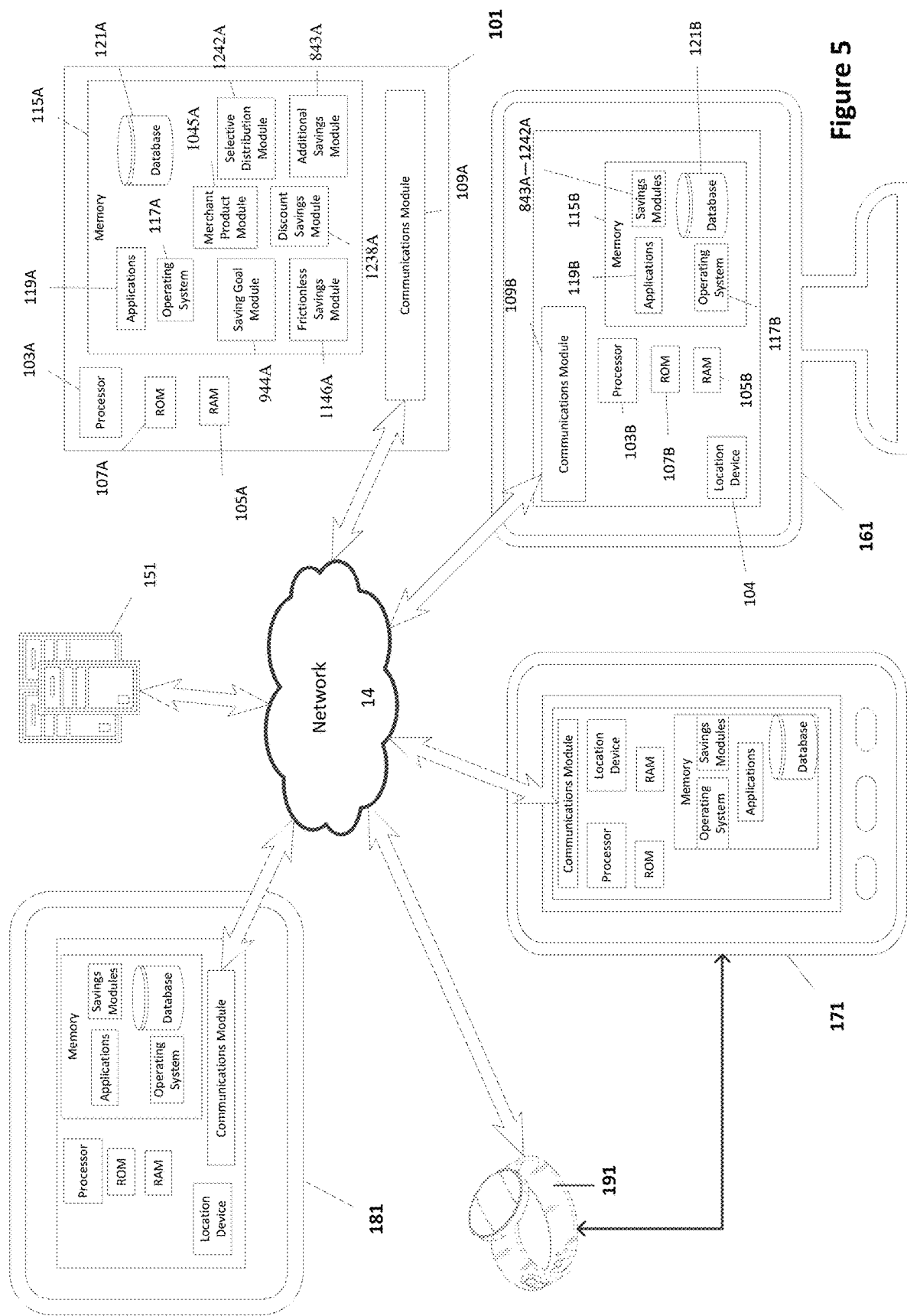
FIG. 5 shows an illustrative operating environment in which various aspects of the disclosure may be implemented.

With reference to FIG. 1, FIG. 4, and FIG. 5, computing device 101 may operate in a networked environment supporting connections to one or more remote computing devices, such as branch terminals 141 and 151, point-of-sale (POS) device 162, ATM 163, retail locations 164, 165, and 166, personal computer 161, smartphone 171, tablet 181, and smartwatch 191. The branch computing devices 141 and 151 may be personal computing devices or servers that include many or all of the elements described above relative to the computing device 101. Moreover, as with POS 162, branch terminals 141 and 151, smartphone 171, or tablet 181 may be POS devices coupled to a computer server (e.g., a computer system operated by a bank or other financial institution) via a network (e.g., one or more routers or computer systems, a computer system operated by the issuer of the credit card or debit card/check card used to make a purchase, and the like) for receiving financial account information (e.g., a credit card reader, debit card reader, check scanner, online bill pay interface, and the like). The POS devices listed above may be electronic cash registers that include barcode reader 192 that is used to read barcodes on products and to automatically enter the products and prices into POS. POS devices may further include a card reader 111 that reads account information from a credit card, debit card, or any other type of financial device that can be used to purchase an item. POS devices may include other devices, such as a keypad, that can also be used to read account information for facilitating a transaction. In one embodiment, POS devices may be located at a retailer.

The network connections depicted in FIG. 1 and FIG. 4 include a local area network (LAN) 125 and a wide area network (WAN) 129, but may also include other networks. When used in a LAN networking environment, computing device 101 is connected to the LAN 125 through a network interface or adapter in the communications module 109. When used in a WAN networking environment, the server 101 may include a modem in the communications module 109 or other means for establishing communications over the WAN 129, such as the Internet. It will be appreciated that the network connections shown are illustrative and other means of establishing a communications link between the computing devices may be used. Communications module 109 may further include a near field communications device (NFC), infrared, or short range wireless devices, such as Bluetooth. The existence of any of various well-known protocols such as TCP/IP, Ethernet, FTP, HTTP and the like is presumed, and the system can be operated in a client-server configuration to permit a user to retrieve web pages from a web-based server. Any of various conventional web browsers can be used to display and manipulate data on web pages.

Additionally, an application program 119 used by the computing device 101 according to an illustrative embodiment of the disclosure may include computer executable instructions for invoking user functionality related to communication, such as email, short message service (SMS), and voice input and speech recognition applications.

In reference to FIG. 5, computer system 101 may include additional savings module 843A, savings goal module 944A, merchant product module 1045A, frictionless savings module 1146A, discount savings module 1238A, or selective distribution module 1242A. These modules may carry out savings programs as described in aspects of the present disclosure for helping users achieve their savings goals. Additionally, personal computer 161, smartphone 171, tablet 181, smartwatch 191, computer system 151 and computer system 141 may also have additional savings module 843B, savings goal module 944B, merchant product module 1045B, frictionless savings module 1146B, discount savings module 1238B, or selective distribution module 1242B as shown at personal computer 161, but which have been omitted from smartphone 171, tablet 181, smartwatch 191, computer system 151 and computer system 141 in FIG. 5 for the sake of clarity.

In accordance with aspects of the disclosure, a method is contemplated to enhance the ability to save money. In one embodiment, the method permits a debit card holder to save as that individual makes everyday purchases. For example, when the debit card holder uses the debit card to make a purchase, the transaction amount for each purchase may be increased to the next integer dollar amount if the transaction is not already an integer dollar amount. If the transaction amount is already an integer value, under alternative embodiments in accordance with aspects of the disclosure, the transaction amount may still be increased to the next greater integer value, or alternatively, remain unchanged. The difference between the actual amount and the increased amount is transferred from the holder's checking account to another account (e.g., a savings account); thus, creating an interest-paying virtual change jar. The aforementioned approach of increasing the transaction amount may be referenced in this disclosure as "the increasing approach." One skilled in the art will appreciate after review of the present disclosure that other triggering events/acts and other techniques for determining a savings amount to transfer are contemplated.

Continuing with the above example, the account holder can receive an additional bonus or match money to encourage use of the savings program. For example, the bonus or match money may be in the form of interest that would be in addition to the interest the holder would normally earn in an interest-bearing account. For example, at the end of the year, the holder's financial institution may match the transferred savings at 100% for the first 3 months and 5% thereafter. The holder may continue to receive this 5% match reward of the transferred savings each year around the anniversary date. This bonus or match money may be capped, for example, up to a predetermined amount of money (e.g., $250). One skilled in the art will appreciate after review of the entirety disclosed herein that the disclosure contemplates other techniques for matching or providing a bonus. For example, one of numerous variations contemplated by the disclosure includes providing different percentage/amount of interest yield during a particular time period.

Disclosed herein are various techniques that may be implemented in an automated savings program as well as various aspects of such an automated savings program. First, the process for user eligibility for matching and enrollment is disclosed. Second, various aspects of savings are disclosed (e.g., calculating the amount, when the amount is transferred, saving for other purposes, credit card transactions, and the like). Third, techniques are disclosed to protect against potentially exceeding the account balance. Finally, various techniques are disclosed for providing a match or bonus. Those skilled in the art will appreciate that any combination of these techniques and aspects may be implemented.

A financial institution may offer the aforementioned financial product/method to new account holders or prospective account holders. In one aspect of the eligibility/enrollment process, based upon user segmentation (e.g., user account status—regular, premium, platinum, gold, and the like; debt card usage—low, moderate, high; and the like), the financial institution may offer varying aspects and/or levels (e.g., higher matching levels, minimum balance requirements, and the like) of financial product/methods to account holders. In another aspect of the eligibility/enrollment process, an account holder may be able to discontinue (i.e., dis-enroll) from the savings program through online and/or other (e.g., telephone, in-person, and the like) methods. Moreover, the account holder may dis-enroll temporarily, for example, to avoid exceeding the account balance. In some instances, a financial institution may configure the automated savings amount transfers such that if the source account balance is below a predefined threshold (e.g., $10) amount, then the automatic savings amount transfers are temporarily deactivated. As such, during the temporary deactivation, the account holder would not enjoy the benefit of automated savings and matching/bonus. Additional features related to exceeding the account balance are also discussed later in this disclosure. In one example, the temporary deactivation feature may be configurable by the account holder through an online interface (e.g., the financial institution's website).

Figure 6:
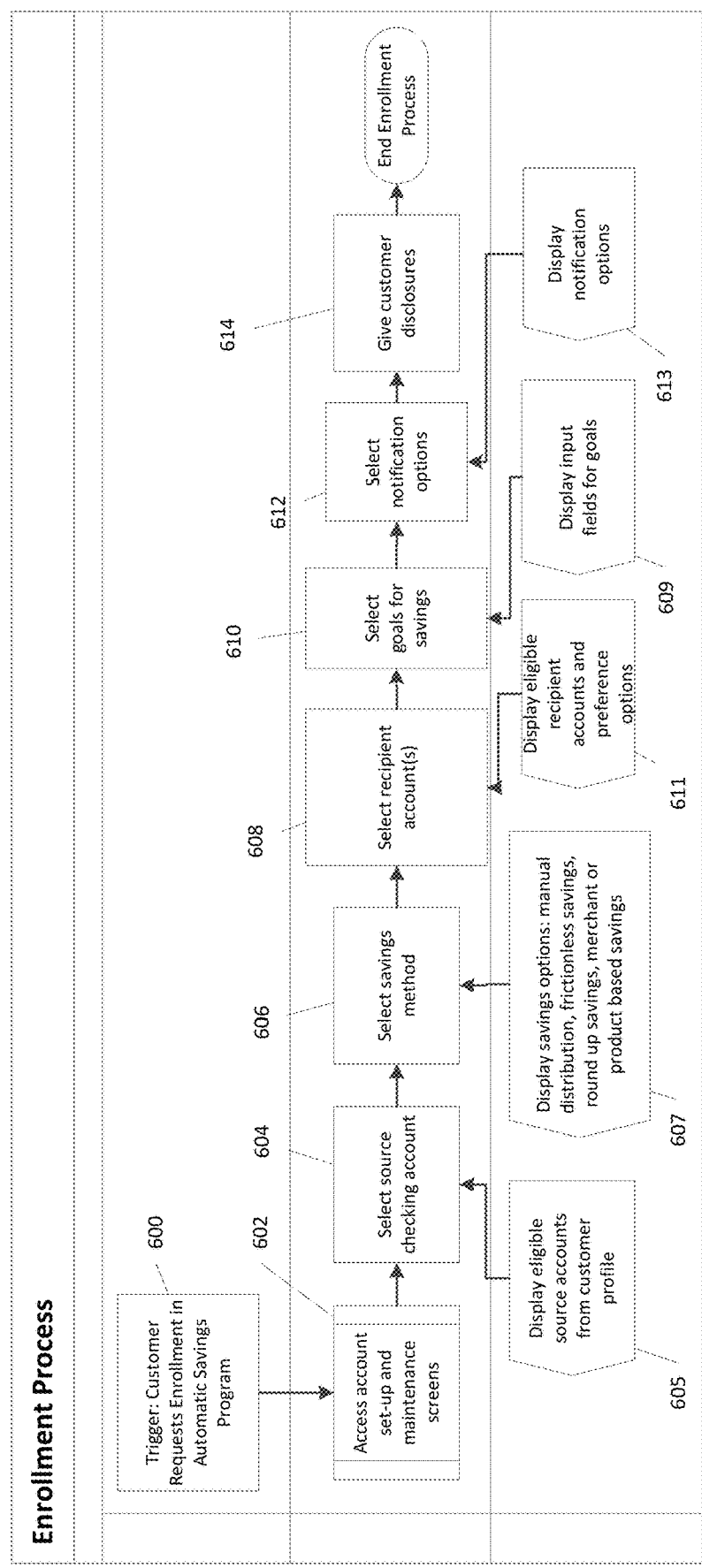
FIG. 6 illustrates a flowchart depicting an enrollment method in accordance with aspects of the disclosure.

Referring now to FIG. 6, a flow diagram of the functionality performed by computer system 101 in accordance with one embodiment of the present disclosure in order to enroll a user in the automatic savings program is shown. The disclosures below will reference elements depicted in FIG. 1 and FIG. 4.

In step 600, a customer of a financial institution requests enrollment in an automatic savings program.

In step 602, account set-up and maintenance screens/interfaces are accessed in response to a user request to enroll in the automatic savings program. In one embodiment, the screens/interfaces are accessed by bank personnel at a terminal locally or remotely connected to computer system 101. In another embodiment, a user may access the screens/interfaces at a terminal remotely connected to computer system 101 through Internet. In another embodiment, the user may access the screens/interfaces with any wireless device capable of connecting to computer system 101 through Internet, such as ATM 163, personal computer 161, tablet 181, smartphone 171, or smartwatch 191.

In step 604, the checking account that is the source of the automatic savings amount is selected. The eligible source accounts are displayed from the user's profile (step 605). In other embodiments, another type of account instead of a checking account can be used, as long as the selected account is a source of funds.

In step 606, the types of debits/transactions that are to be "round up" are selected. "Round up" refers to one method used to calculate a monetary amount (e.g., savings amount) from a transaction. In one embodiment, the round up amount is an amount of excess funds produced by applying a rounder transaction to the amount of a transaction such as a credit/debit card charge at POS 162. If the rounder transaction rounds up to the nearest dollar, for example, a purchase made for $54.08 would generate a rounded amount of $0.92. Other embodiments of the present disclosure may round up to a predetermined amount besides the nearest dollar. Still further, other embodiments of the present disclosure may calculate the savings amount using a method other than round up. For example, a fixed percentage can be applied to each transaction to calculate a savings amount, or a fixed amount of money (e.g., $1.20) can be considered the savings amount. The available debits/transaction types to be round up are displayed (step 607) and can include check card/debit card POS transactions, or any other types of debits. Examples of other debits that can be the subject of round up or other calculation of a savings amount include paper checks, electronic bill pay, electronic checks, automatic payments and Automated Clearing House ("ACH") transfers.

In step 608, the recipient account or accounts for the savings amount may be selected based on the displayed eligible recipient accounts (step 611) and preference option fields for the accounts can be inputted. In one embodiment, possible recipient accounts include the user's own recipient account, person-to-person transfer (e.g., a grandparent's round ups being credited to a grandchild's recipient account), and the like. In general, any recipient account that can accept transfers can be eligible for selection. If multiple recipient accounts are selected, the user can choose a percentage distribution for each of the recipient accounts, or another mechanism that can be used to divide the savings amount between the multiple accounts or create a preference for savings between the accounts.

In step 610, goals may be selected for the recipient account or accounts. In one embodiment, the computer system may present the user with an option to input the user's desired financial goals (step 609). To determine the user's desired financial goals, the server may request information from the user regarding the user's qualitative or quantitative goals, such as "buy a car," "pay for child's college education" or "save $2,000." The computer system can additionally request a time frame to achieve this goal, and may also request the user's income and expenditures, and any additional information that may be relevant to ascertaining the appropriate savings method for the user. A separate goal can be selected for each recipient account if multiple recipient accounts are selected for the program. The user may also select intermediate goals for a recipient account to help the user stay on track for reaching their goal for the recipient account.

In step 612, notification services may be selected for the savings accounts. The computer system may display the notification options (step 613).

In step 614, the user disclosures may be presented to the user to agree to before enrollment as display notifications (step 613).

Figure 15:
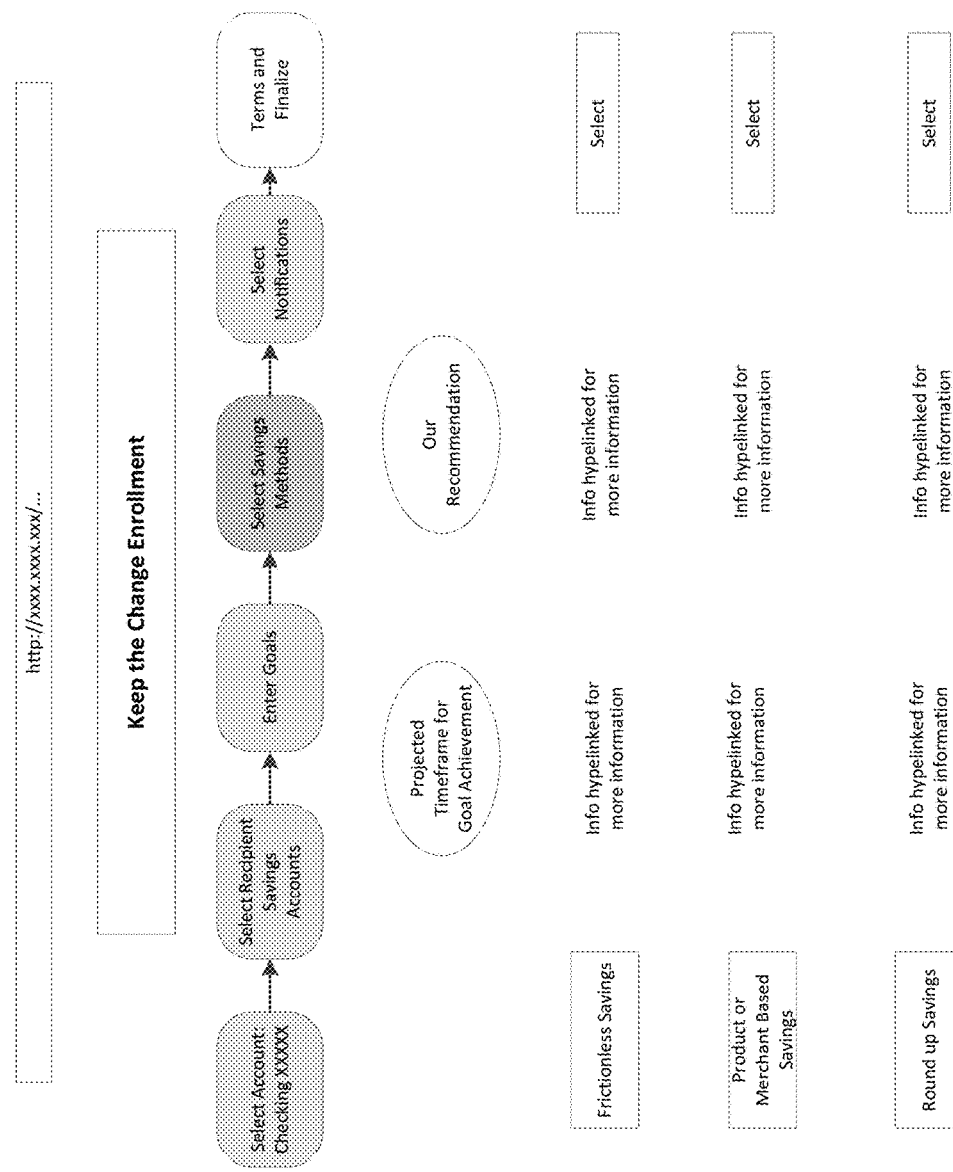
FIG. 15 depicts a graphic user interface depicting a method of enrollment in accordance with aspects of the disclosure.

Referring to FIG. 15, a graphical user interface (GUI) of an embodiment of the present disclosure showing an enrollment interface for a user to enroll in a savings program is shown. In the example disclosed in FIG. 15, a user may enroll in a savings program via a GUI interface. In reference to FIG. 5, a GUI interface may be accessed via branch terminals 141 and 151, ATM 163, retail locations 164, 165, and 166, personal computer 161, smartphone 171, tablet 181, and smartwatch 191.

In step 1500, the user selects the source checking account via the GUI interface.

In step 1502, the user selects the recipient savings account(s).

In step 1504, the user enters the savings goals for the recipient account(s).

In step 1506, the user selects the savings methods for the recipient account(s). The user may select one, or multiple savings methods as shown (step 1512). The enrollment program may also give projected time frames for completing the user's savings goals (step 1514) based on a time frame and savings amount disclosed by the user (step 1504). Further, the enrollment GUI may also recommend particular savings methods based on the goals entered by the user (1516).

In step 1508, the user selects notifications for the savings methods, as described more fully in reference to FIGS. 7-10 and 12.

In step 1510, the user is presented with terms and conditions and to finalize the enrollment process.

In one embodiment, the savings amount (e.g., monetary amount) may be transferred from a first source account (e.g., any type of account as long as it is a source of funds) to a recipient account (e.g., a money market account, a savings account, and the like). In an alternative embodiment, the savings amount may be transferred from a first source account to multiple recipient accounts. Such an alternative embodiment provides additional flexibility of the savings program for the user.

In yet another embodiment, the savings amount may be applied against outstanding debt. For example, the savings amount may be used to pay down debt (e.g., mortgage, student loans, credit cards, and the like) as another use of the money saved. Any matching (or bonus) amount may also be applied against outstanding debt. In another embodiment, the recipient account may be a retirement account (e.g., an IRA account, Roth IRA account, and the like).

In accordance with various aspects of the disclosure, the savings amount automatically transferred from an account holder's source account to a recipient account may be calculated based on one or more factors. For example, under an increasing approach a transaction amount may be increased to the next highest integer value. Meanwhile, under another approach, the transferred savings amount may be calculated by decreasing the transaction amount to the previous lowest integer value if the transaction is not already an integer dollar amount. If the transaction amount is already an integer value, under alternative embodiments in accordance with aspects of the disclosure, the transaction amount may still be decreased to the previous lowest integer value, or alternatively, remain unchanged. The aforementioned approach of decreasing the transaction amount may be referenced in this disclosure as "the decreasing approach."

As further explained below, the decreasing approach may be useful in the case of a savings program based on credit card transactions. In another example, the savings amount may be a fixed amount (e.g., $1, $0.50, $5, and the like) per transaction. In yet another example, the total savings amount for a period of time (e.g., a year) may be limited to a predefined maximum amount.

In an alternative embodiment, an account holder may customize (e.g., through an online graphical user interface) the specifics of its automated savings program. For example, the user may configure, at account enrollment and thereafter, one or more various features of the automated savings account discussed herein including, but not limited to, the following: the source account(s), the recipient account(s), the savings scheme (round-up, percentage amount, predetermined dollar amount, and the like), the aggressiveness of the savings scheme (e.g., in the case of an increasing approach, the amount of transferred savings), charitable savings, payment of exiting loans, or savings for a specified purchase item. For example, a user may designate the increasing approach to use the next highest $5 denomination. As such, the amount of transferred savings amount is greater. Likewise, the aggressiveness of the transferred savings amount may be controlled for other types of monetary amounts (e.g., savings amounts) disclosed herein and contemplated by one of skill in the art after review of the entirety disclosed herein. Such an embodiment provides customization of the savings program for the user account. Such a computer system may send information about user preferences/settings are used by an incentive engine and/or provided to a parameter-based rules engine (e.g., an incentive engine that accepts different parameters to customize the matching/savings aspects for a user in accordance with various aspects of the disclosure).

Figure 2:
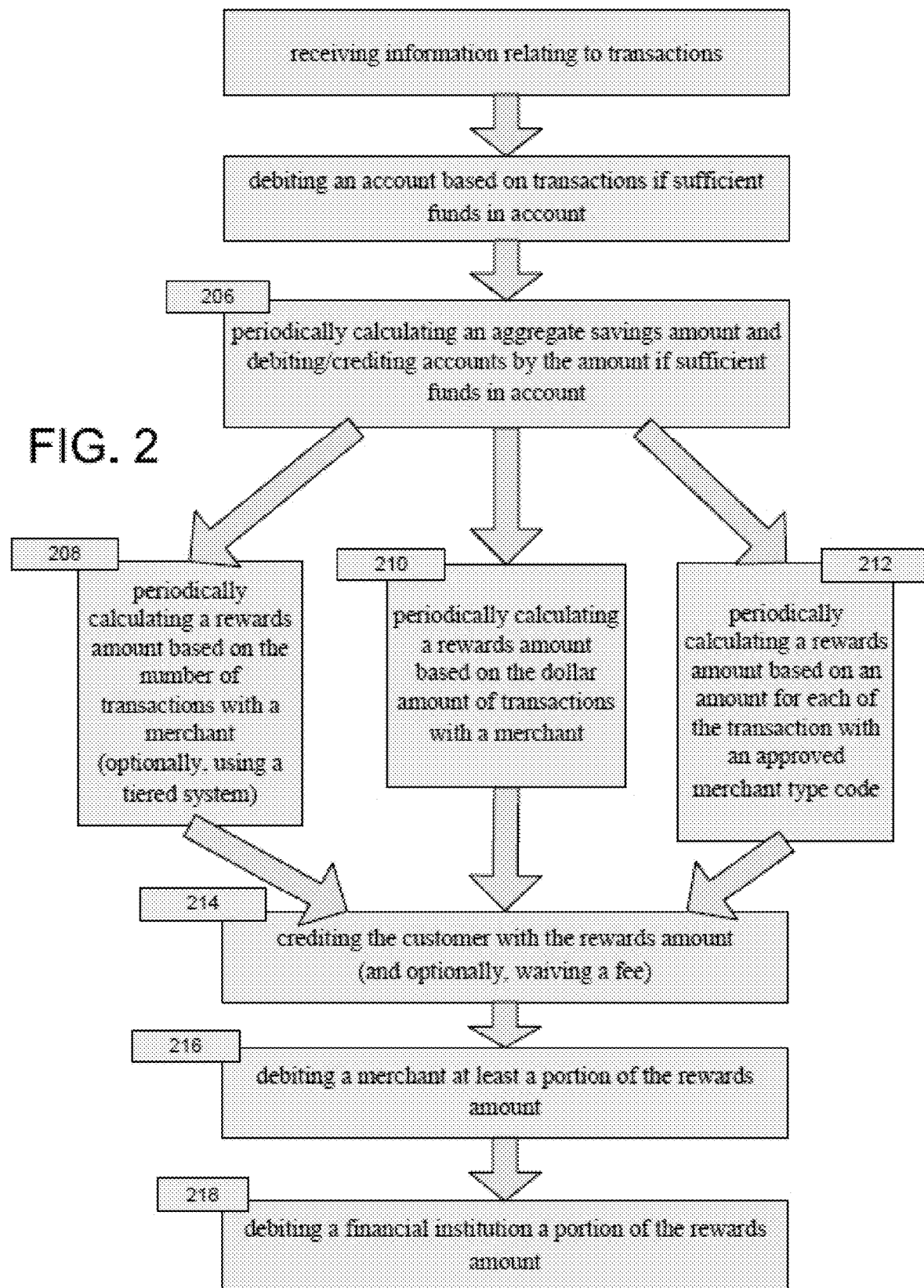
FIG. 2 illustrates a flowchart depicting various steps performed in accordance with aspects of the disclosure.

Each of the above-referenced customizable features may be implemented as a parameter for the user's accounts. In one example, once the user's account has configured for the customized automated savings program, values for the various parameters may be passed to the deposit applications. This information may be passed to deposit applications, in one example, as part of eligibility information. The deposit applications may thereby implement the user's customized savings program in accordance with the parameter values provided. The deposit applications may determine the transferred savings amount based on the parameter designated for the increasing approach ($5 denominations, $10 denominations, and the like). These transferred savings amounts may be aggregated together for each account, and one debit may be charged to the checking account. Referring to FIG. 2, if sufficient funds were available, the transaction may post to the checking account (in step 206) and a request for transfer to the recipient account is sent to a credit engine. The credit engine verifies the existence and status of the receiving account and creates a credit transaction for the transferred savings amount to post in the next processing cycle. It will be appreciated that the amount of customization that is afforded to the user is proportional to the complexity of the system for the financial institution.

In accordance with aspects of the disclosure, the transfer of the savings amount from a source account to a recipient account may occur at various times and/or time intervals. For example, as described in one embodiment in U.S. application Ser. No. 11/161,418 filed Aug. 2, 2005, which was previously incorporated by reference herein, the savings amounts for all transaction in a day may be aggregated and a single transfer may be performed daily. One skilled in the art will appreciate after review of the present disclosure that the transfer operation may occur at various times (e.g., weekly, monthly, bi-weekly, bi-daily, annually, and the like). For example, the savings amount may be transferred in near real-time (i.e., a separate transaction for transferring the savings amount for each transaction may be processed once the triggering transaction has been received at computer system 101.) As such, an account holder may find numerous transfers of savings amounts occurring throughout a day instead of a single aggregated transfer.

Figure 13:
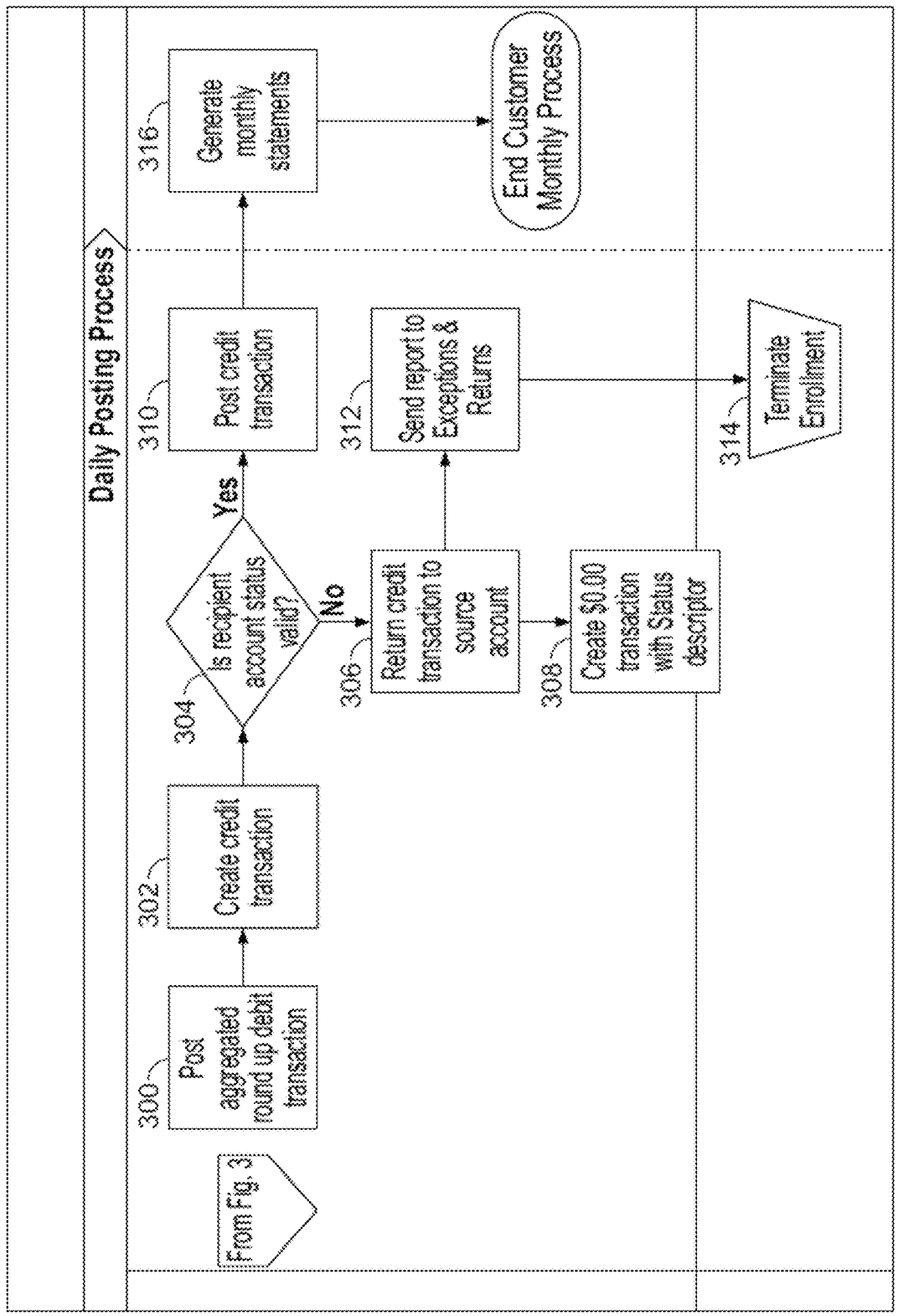
FIG. 13 illustrates a flowchart depicting a posting method in accordance with aspects of the disclosure.

Referring to FIG. 13, a flow diagram of the functionality performed by computer system 101 in accordance with one embodiment of the present invention to perform a daily posting of the automatic investment transaction is shown.

In step 300, the aggregated round up debit transaction is posted.

In step 302, the credit transaction is created.

In step 304, a determination is made if the recipient account(s) selected at step 608 of FIG. 6 is valid. If it is valid, the credit transaction is posted (step 310).

In step 306, if the recipient account(s) is not valid at step 304, the credit transaction is returned to the source account and a $0.00 transaction is created with a status descriptor. A report of the invalid source account is sent to an "exceptions & returns" file and enrollment of the automatic investment account for that customer is terminated (steps 312, 314).

In step 316, monthly statements are generated that include the automatic investment function. Both the source and recipient accounts may display a month-to-date and year-to-date summary of round up transfers on their statements.

In another embodiment of the present disclosure, as eligible transactions are received at the financial institution, they may be posted to the deposit account in a near real-time process. Various techniques may be used to calculate the transferred savings amount using the increasing approach. In one such technique, each transaction received by the deposit account may have its transferred savings amount under the increasing approach calculated and posted at the time of the transaction. The aforementioned transaction may be sent immediately to a credit engine. The credit engine may create a transaction which may be sent immediately to a receiving account. Under another technique, each transaction received by the deposit account would have the transferred savings amount using an increasing approach calculated and stored in a bucket. During the end of day reconciliation, the stored value may be compared to the ending balance, and if the balance remains positive, a transaction may be posted to the deposit account. This amount will be sent to a credit engine to perform the same process as in the aforementioned technique.

In accordance with aspects of the disclosure, the savings amount may be obtained automatically from one or more source accounts. For example, an account holder may designate a checking account at a financial institution as the source account. In another embodiment, the account holder may designate more than one source account, for example, an alternate source account in the event that an account contains inadequate funds. Alternatively, the savings amount may be sourced from multiple accounts and the percentage to be taken from each account may be designated (e.g., 25% from checking account A and 75% from checking account B). Such an embodiment provides additional flexibility of the savings program for the user.

In accordance with various embodiments of the disclosure, the savings amount may be transferred to a recipient account. The recipient account (e.g., savings account) may be a high interest yield account designated for such a savings program. In some embodiments, the recipient account may be configured such that the account holder may not be able to withdraw the transferred savings amount from the recipient account before a predefined period of time (e.g., one year) without incurring additional charges. As such, the savings account encourages the account holder to save money and earn a higher interest yield.

In an alternative embodiment, the savings amount may be transferred from a first source account to multiple recipient accounts (e.g., a money market account, a savings account, retirement account, and the like). In yet another alternative embodiment, the multiple recipient accounts may be owned by different people. Such an embodiment provides additional flexibility of the savings program for the user. U.S. application Ser. No. 11/161,418 filed Aug. 2, 2005, which was previously incorporated by reference herein, lists numerous examples of recipient account configurations.

In another embodiment, the savings amount may be applied against outstanding debt. For example, the savings amount may be used to pay down debt as another use of the money saved. Any matching (or bonus) amount may also be configured to be applied against outstanding debt. For example, instead of creating a deposit to the savings account, a credit generating system in communication with computer system 101 may create a payment to, for example, an associated credit card, a personal or business loan, a home mortgage or home equity loan, a car loan, a student loan, and the like. Moreover, business rules may be formulated and used to determine whether the payment is applied to interest or principle. In an embodiment where the savings amount is applied to a non-credit card debt, a similar technical implementation may be taken. For example, computer system 101 may submit a payment on behalf of the account holder to reduce the outstanding debt. Similar to the technical steps to create a transaction to pay down credit card debt as explained herein, the automated payment of a student loan debt, car loan debt, and other debt vehicles perform accordingly. Rather, the transaction for each type of debt vehicle may require formatting according to the receiving system.

In yet another embodiment, the recipient account may be a retirement account (e.g., an IRA account, Roth IRA account, 401(k) account, and the like). Alternatively, the recipient account may be a gift card account where the account holder's savings are applied to a gift that he/she may use themselves or give to another as a gift. Alternatively, the recipient account may be a health savings account.

Figure 3:
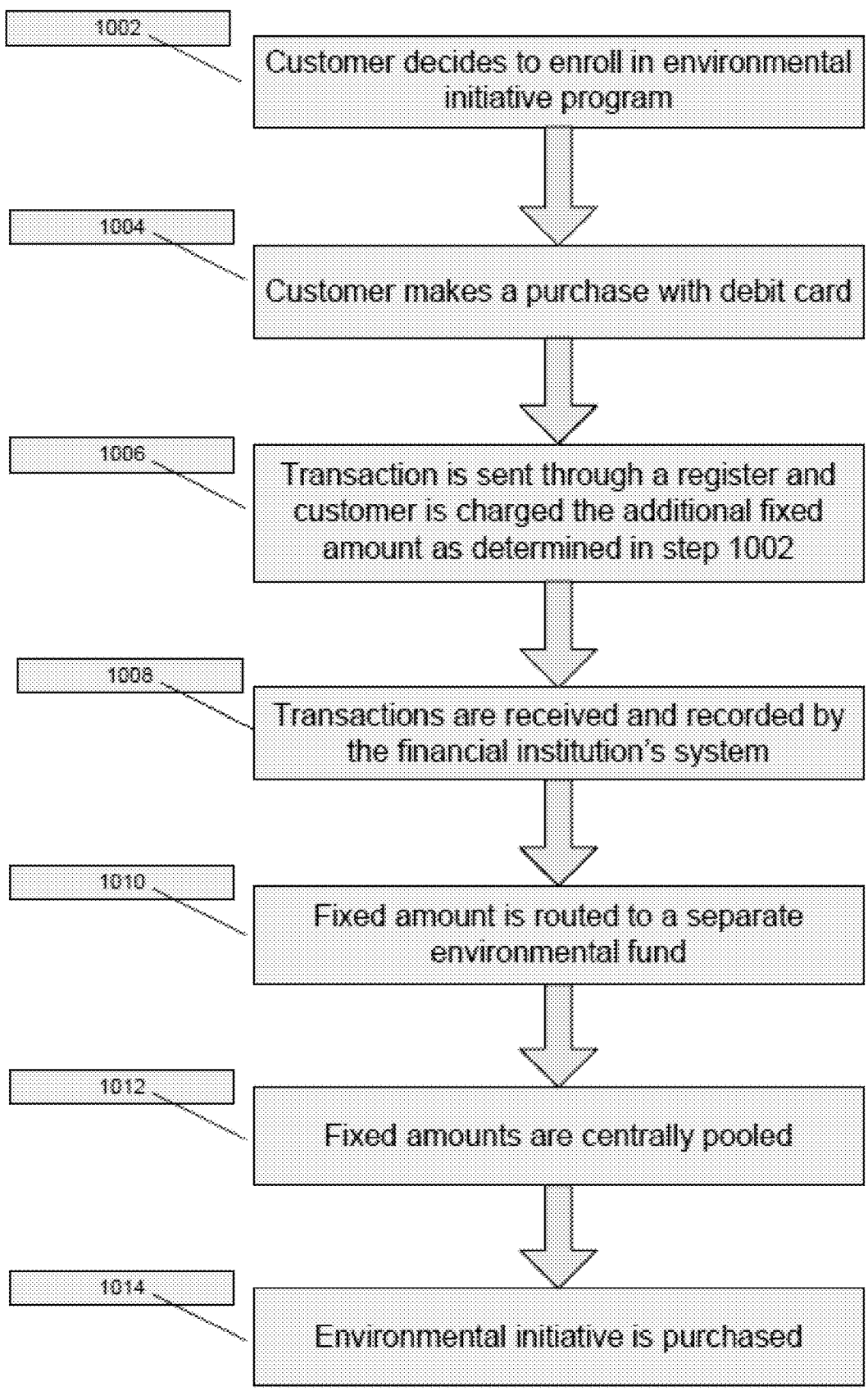
FIG. 3 illustrates a flowchart depicting a method in accordance with aspects of the disclosure.

In yet another example, an automated savings program may allow an account holder to participate in a charitable program. In the example provided with reference to FIG. 3, a user may enroll in a charitable program (step 1002) that draws additional funds through additional charges to debit purchases (step 1006), that is used to purchase an environmental initiative program (step 1014). By enrolling and participating in this environmental program, a financial institution adds a predetermined amount (e.g., $0.01) to the account holder's total purchase amount for each transaction (e.g., each time they use their debit card) (step 1006). One skilled in the art will appreciate that the financial institution has the option of offering differing amounts (e.g., amount higher (or lower) than 1¢ per transaction) to its account holder; thereby creating more (or less) purchasing power to the environmental program. Such an embodiment provides additional flexibility of the savings program for the user.

Next, in participating in a charitable program, the account holder may make a purchase using a debit card (step 1004). This transaction is sent through a point-of-sale (POS) device, such as those described in U.S. application Ser. No. 11/161,418 filed Aug. 2, 2005, which was previously incorporated by reference herein, and the account holder may be charged the additional predetermined amount (step 1006). One skilled in the art will appreciate that this fixed amount could be withdrawn from not only debit card transactions, but also credit card transactions, or other purchases completed by an equivalent account and/or card. When the predetermined amount is withdrawn from the user and transferred to the environment program, the transfer transaction is received and recorded by a computer system at the financial institution (step 1008). In one example in accordance with aspects of the disclosure, the predetermined amount may be routed to a separate, second environment fund (step 1010). The predetermined amounts from each of the users enrolled in the program may be pooled together (step 1012). Following this, the pooled funds can be paid to the environmental program (step 1014).

Another example, similar to the one described above, begins with an account holder selecting to contribute to an environmental program which purchases carbon offsets. This type of environmental program may give the account holder a simple way to partially neutralize their carbon impact and be part of a larger collective initiative. The account holder may configure their participation in the program to add one cent (1¢) to each of his/her debit card transactions. The account holder may then make a purchase of $1.50 using their debit card. The account holder may be charged an additional 1¢ for a total of $1.51. The 1¢ may be routed to a separate account which will be used to purchase carbon offsets and may be centrally pooled together with other account holders participating in the environmental program. Finally, with these pooled funds, carbon offsets may then be purchased. With a program such as this, the account holders of a financial institution may be collectively responsible for: negating the impact of 150,000 SUVs on the road for a year, or protecting the equivalent of 4,800 football fields of tropical rainforest from deforestation, or negating the impact of 1,000 residents of each of the 50 states for a year.

In addition to the use of a debit card as disclosed in U.S. application Ser. No. 11/161,418 filed Aug. 2, 2005, which was previously incorporated by reference, other events/acts may results in an automatic transfer occurring. For example, the use of a credit card in making a purchase may act as a trigger to cause the transfer of a savings amount for the credit card holder. When the holder makes a purchase using a credit card associated with a financial institution, the purchase transaction amount is decreased using a decreasing approach, actually reducing the amount the holder is charged. In some embodiments, the transaction amount may be reduced by less than the aforementioned amount. In one example, the savings amount may be a fixed amount or a percentage of the savings amount.

In addition, the financial institution may transfer the difference between the amount of the transaction under a decreasing approach and the actual transaction amount from the holder's checking account to a second account. For example, User #1 uses a credit card to make a purchase for $10.25. The transaction amount charged to User #1 for the purchase is decreased to $10. Moreover, the financial institution covers the outstanding $0.25 on User #1's behalf as a bonus/matching amount. Furthermore, the bank transfers $0.25 (i.e., the bonus/matching amount) from User #1 checking account at the financial institution to her savings account. As such, the financial institution facilitates a savings program for the account holder. In some embodiments, at the end of the year (or any other period of time), the financial institution may yet again reward the card holder by matching a percentage (e.g., 100%, 50%, and the like) of the transferred savings amounts. Alternatively, the card holder may be rewarded in many of the other ways as described throughout this disclosure. The card holder may choose to have this matched/bonus amount applied against any credit card balance, or may be deposited into any of the holder's accounts (e.g., checking, savings, and the like).

In another embodiment in accordance with aspects of the disclosure, when an account holder makes a purchase using a credit card associated with a financial institution, the difference between the transaction amount and the increased amount under an increasing approach is transferred from the holder's checking account to another account (e.g., a savings account). For example, User #2 uses a credit card to make a purchase for $10.25. The transaction amount for the purchase remains $10.25. Meanwhile, the financial institution deposits $0.75 to a savings account under User #2's name as a bonus amount. As such, the financial institution facilitates a savings program for the account holder.

Furthermore, as described in U.S. application Ser. No. 11/161,418 filed Aug. 2, 2005, which was previously incorporated by reference, a method contemplated to enhance a person's ability to save money may include a feature to protect and/or avoid exceeding the account balance. Such a feature designed to avoid exceeding the account balance may include, in some embodiments, a retroactive feature. In one example such a feature enables a financial institution to postpone the transfer of a savings amount if the transfer would result in the holder's source account exceeding its account balance. The financial institution may retry the postponed transfer at a later time (e.g., after six hours has elapsed, after twelve hours has elapsed, and the like) and/or at regular intervals (e.g., daily, bi-daily, hourly, weekly, and the like). For example, the financial institution may predefine the maximum number of retries (e.g., five retries) and the interval between each retry (e.g., wait one day between each retry) to prevent a scenario where postponed transfers are accrued and retried indefinitely. In yet another example, a portion of the savings amount may be applied without causing a negative account balance, while the remaining portion is postponed (or cancelled) as described in the aforementioned retroactive feature.

Alternatively, a feature designed to avoid exceeding the account balance, in accordance with aspects of the disclosure, may include an option to designate a second source account to be used if a transfer of the savings amount from the first source account would cause it to exceed the account balance. The second source account may be of any type recognized by one of skill in the art as a viable source of funds. Examples of such sources of funds are disclosed or suggested throughout this disclosure.

In yet another embodiment in accordance with aspects of the disclosure, a feature designed to avoid exceeding the account balance may include a grace period during which an account holder may remedy the situation of exceeding the account balance. to avoid charges associated with exceeding the account balance. For example, an account holder may deposit funds in an account before the close of the business day to eliminate any occurrences of exceeding the account balance that may have been caused earlier in the day due to transactions. In such a situation, the account holder may not be charged for exceeding the account balance (or may be charged only a reduced amount or percentage of the normal fee for exceeding the account balance).

In accordance with aspects of the disclosure, a computer system may be used as a base to implement one or more aspects of the feature designed to avoid exceeding the account balance. Accounts that have a negative account balance may have the daily (or other time interval) transaction corresponding to the transfer savings amount added to a retry file with a counter for the number of days (or other time interval) the transaction can be reapplied. The computer system 101 may allow the financial institution to save these files and check the accounts for available funds for a period of time. The transactions from the retry file may be included with the next processing day's posting items. If the account has a negative account balance, the retry counter may be decremented by one and the transaction may be re-added to the retry file. If the account does not have a negative account balance, the aforementioned transactions may be passed forward for processing to create the savings credit. The computer system 101 may input the savings credit into a deposit system for a processing cycle.

Figure 14:
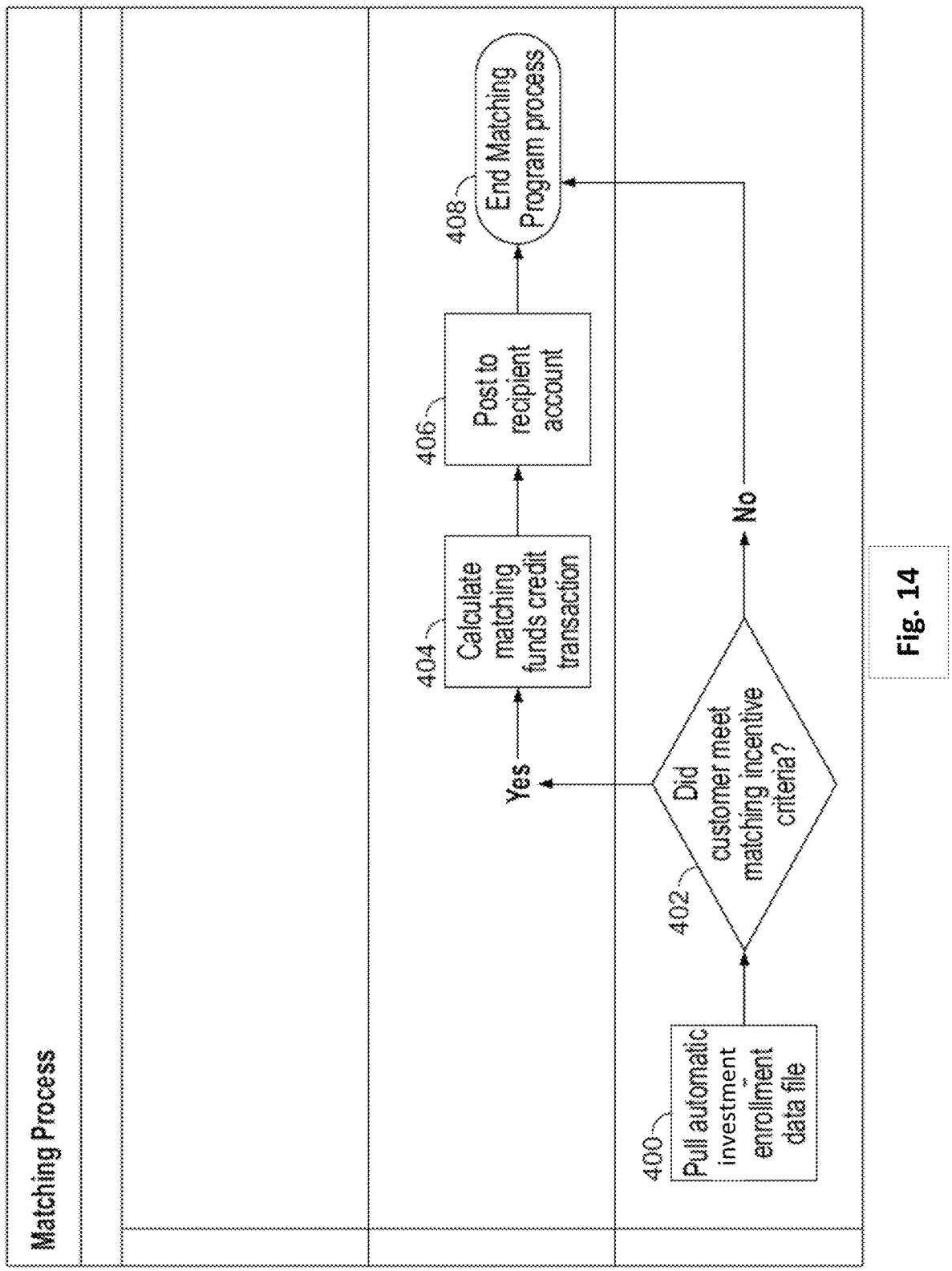
FIG. 14 illustrates a flowchart depicting a method of matching savings in accordance with aspects of the disclosure.

Referring to FIG. 14, a flow diagram of the functionality performed by a computing system 101 in accordance with one embodiment of the present disclosure to implement a matching process in conjunction with the savings program is shown.

In step 400, during the daily posting process of FIG. 14, or at another point in the process (e.g., quarterly, annually, and the like), the customer data file for the automatic investment program is pulled. The data file stores all transactions eligible for matching and other data, such as the length of enrollment for the user, which can be used to determine if the user has met the matching incentive criteria.

In step 402, the computing system determines if the user has met the matching incentive criteria. If not, the matching process is ended (408).

In step 404, if the user meets the matching incentive at step 402, the matching funds credit transaction is calculated. The matching funds are then posted to the recipient account (406).

Referring to FIG. 2, a system and method are disclosed for providing payments as a reward for savings. In one example, the matching (i.e., bonus) paid to the account holder (in step 214) may be based on one or more factors. For example, as described in one embodiment in U.S. application Ser. No. 11/161,418 filed Aug. 2, 2005, which was previously incorporated by reference herein, the financial institution (in step 218) may offer to match the transferred savings amount under the increasing approach (or savings amount under other approaches) by providing $0.05 for every transaction. In another example, the financial institution (in step 218) may offer $1.00 (or any other predefined amount) for every transaction (e.g., debit card purchase, credit card purchase, and the like). The matching may be provided for only a predetermined period of time, for example, during the first six months of enrolling in the program/product. Furthermore, the matching may be a based on a percentage of the transferred savings amount (e.g., 100%—dollar for dollar, or 50%—50 cents to the dollar, and the like). Computer system 101 may verify that an account holder is eligible (in steps 208, 210, and/or 212) for matching/bonus before crediting the match amount to the account holder's recipient account.

In yet another embodiment in accordance with aspects of the disclosure, the matching/bonus amount may be a predetermined amount provided at a regular interval. For example, a $100 may be automatically transferred from an account holder's checking account to a savings account. The $100 transferred savings amount may be entitled to the same (or more or less, as would be apparent to one skilled in the art after review of the present disclosure) of a match/bonus as other savings amounts transferred into the account. For example, under a segmented approach, transferred savings amounts from debit card (or credit card) use may be entitled to full matching, while transferred savings amount from an automatic monthly transfer may be entitled to half matching. In addition, the period of time during which the account holder may qualify for matching on the different types of transferred savings amounts may also vary (e.g., the automatic monthly transfers are eligible for matching for only three months, while the other type may be eligible for six months). In another embodiment, the matching may require that the total balance on the account is growing month after month. In yet another embodiment, the account holder may be required to maintain a minimum balance in an account (e.g., checking and/or savings) to be eligible for matching/bonus.

In yet another embodiment, the total amount of matching/bonus for a given period of time (e.g., one year) may be limited to a predefined maximum value. Alternatively, the number of transactions eligible for matching during a given time period (e.g., a day) may be limited to a predefined maximum number.

In reference to FIG. 1 and FIG. 2, in another example, the match/bonus may be based (in step 208) on a balance tier system (i.e., the amount of balance in a holder's account may categorize them into different tiers with varying matching/bonus levels). An incentive engine executing in a computer system 101 (e.g., using processor 103) may receive the appropriate balance total from a deposit system. The received balance total may be a pre-calculated value that the computer system 101 may use without further intensive processing. Alternatively, the received balance total may be calculated at computer system 101 in numerous ways in accordance with aspects of the disclosure: a multi-month moving average, monthly average, current balance, average daily balance over the prior 12 months, average daily balance over the last 30 days, balance at the time the matching/bonus amount is calculated (i.e., the balance in the account on the date when the, e.g., debit card purchase occurred), minimum balance during the prior 30 days, average over the last 90 days, and the like The incentive engine may comprise of computer-executable instructions used to determine the match level based on this calculated balance. The incentive engine may access (e.g., in memory 115) a table with information about match level and the balance total corresponding to that match level. At least one technical benefit of such a system is that it allows the tiers or match levels to be changed with greater flexibility.

For example, an account holder with a balance less than $1,000 may receive a 2% match on the transferred savings amount. Meanwhile, an account holder with a balance of at least $1,000, but not more than $10,000 may receive a higher match (e.g., 5%) on the savings amount. Moreover, a holder with a balance of $10,000 or more may receive an even higher percentage match. One skilled in the art after review of the present disclosure will appreciate that the matching may be other than a percentage amount. For example, the balance tier may include an approach where, as the balance increases, the matching is a predetermined amount per transaction that also increases with each balance tier.

In another example, the match (or bonus) may be comprised of rewards based on certain user purchase behavior (e.g., double the match for gas purchases). Yet another way to reward users may be based on the number of transactions or purchase volume over certain period of time. For example, an institution may provide a higher matching level to an account holder that achieves more than a threshold number of card transactions (e.g., credit, debit, and the like), or spends greater than a particular amount per month on a card (e.g., credit, debit, and the like)

The aforementioned features in accordance with aspects of the disclosure and as referenced in FIG. 1 and FIG. 2 may be implemented in a computer system 101. When computer system 101 receives POS transaction information, the transactions may have a code associated with it that links the transaction to a merchant type. Such a code may be used to determine the matching (i.e., incentive package) for the transaction. For example, an account holder may receive higher matching/bonus for purchases at a particular merchant (in step 208 and 210), or for particular types of purchases (e.g., bookstore purchases to encourage education, healthcare purchases/costs to encourage good health) (in step 212). In some instances, a financial institution may waive a maintenance fee (e.g., monthly fee) (in step 214) based on the number of transactions (e.g., debit card or credit card) or based on the number of dollars spent on purchases. An incentive engine executing in computer system 101 may track the number of transactions on an account (e.g., debit card account) and/or the amount of dollars spent from each account. If an account exceeds a threshold value (in step 208), an additional bonus/matching (or reward) may be assessed for the account. The incentive engine may be comprised of computer-executable instructions executed by a processor 103 in computer system 101.

In another embodiment, a merchant matching feature may be included in accordance with aspects of the disclosure. For example, a list of merchants may be provided to an account holder that will cause the account holder to achieve increase matching/bonus levels for his/her savings amount. In one example, the merchants may provide (in step 216) a portion or all of the matching/bonus funds transferred to the account holder's account for purchases associated with the merchant. As such, the account holder may be motivated to shop with the merchant. One of ordinary skill in the art after review of the present disclosure will appreciate that various features and aspects of the disclosure may be combined with the aforementioned merchant matching feature and such combinations are contemplated by the disclosure. For example the merchant matching feature may be combined with a tiered approach disclosed herein to provide higher levels of matching/bonus for those account holders with increased number of transactions with a merchant or increase amount of total transaction amount with a merchant.

In yet another example, the matching/bonus may depend on the number of products an account holder has with a financial institution. A computer system 101 may include or communicate with the financial institution's user information system. The user information system may provide information about the overall user relationship (e.g., the number and type of accounts a person has with the institution, how long the person has been an account holder, and the like) and the computer system 101 may determine matching level accordingly. For example, a table in memory 115 at the computer system 101 may link different matching/bonus levels to different levels of user loyalty. A long-time user with a large number of accounts (e.g., auto loan, home loan, home equity loan, investments, deposits, and the like) with substantial balances may be designated at the highest user loyalty level, thus receive a high bonus/matching (e.g., 100% matching).

In yet another example, an account holder may choose to receive the match as reward points that can be redeemed for merchandise, gift cards, airline miles, and the like. For example, the account holder may identify an item they wish to purchase. Once sufficient matching amounts have accumulated for the account holder, a financial institution may contact a merchant selling the product, and procure the product for shipment to the account holder. The account holder may be notified for final approval before the institution makes the final purchase and shipment. Alternatively, the financial institution may procure the product when the sum of the account holder's savings amount (from automatic transfers through a savings program) and match amount is sufficient to purchase the item.

Finally, in another example, the matching/bonus may be based on online bill pay transactions. As such, an account holder may be provided an incentive to use electronic (i.e., online) bill pay. For example, an account holder that registers for electronic statement in lieu of paper statements may be afforded a higher matching/bonus level than a holder that does not. Likewise, an account holder that registers for direct deposit may be allocated a higher matching/bonus level than a holder that does not. Moreover, a financial institution may encourage its account holders to use direct deposit by increasing (e.g., using the increasing approach) their paycheck amount and other amounts directly deposited with the institution. One skilled in the art will appreciate that other online/electronic services may be afforded a greater incentive among users and prospective users when linked to a higher matching/bonus level.

In another example, the matching (i.e., bonus) paid to the account holder may be based on the account holder growing an account balance over a period of time (e.g., subsequent number of months). For example, an account holder may be paid a particular matching/bonus level for the first 3 months, but if the holder increases the balance of a savings account for the subsequent six month following the first 3 months, a financial institution may retroactively apply a bonus (e.g., 2% interest, and the like) to the first 3 months balance. One skilled in the art will appreciate after review of the present disclosure that there are numerous techniques disclosed for calculating balance for a period of time and may be applied to the aforementioned embodiment. In another example, the account holder may be required to maintain a minimum balance (e.g., $300) and/or enroll in an automatic scheduled transfer (e.g., a monthly automated transfer of $25 from a checking to the savings account) to be eligible for the aforementioned retroactively applied bonus feature. Furthermore, in yet another embodiment, if the savings account balance is the same or higher at the one-year anniversary date of enrolling in the savings program, a financial institution may at least double the matching/bonus amount to help grow the savings amount even more.

In yet another embodiment, the match/bonus paid to an account holder may be based on his/her use of online bill pay features. For example, online bill pay transaction codes may be designated in computer system 101 (e.g., by adding the codes to a list of transaction codes identified as eligible for automatic savings and/or matching) to trigger the transfer of automatic savings amounts. Therefore, when such transactions appear on an account holder's statement, the financial institution may determine that an online transaction (e.g., online bill pay transaction or other similar type of online transaction) has occurred, and provide a matching/bonus contribution.

In addition, to encourage additional savings, a financial institution may offer an account holder the option to increase (e.g., double) a matching/bonus level if the account holder enrolls for an automatic scheduled transfer of at least a predetermined amount (e.g., $25/month) to a saving account. The matching/bonus level may be phased out such that the account holder receives full matching for a period of time (e.g., the first 3 months), and then a fraction of that amount (e.g., 10%) ongoing thereafter. In another embodiment, the account holder may be required to maintain a minimum deposit amount (e.g., $300) in his/her savings account in addition to the aforementioned in order to be eligible for the increased matching/bonus level. In another example, if the account holder does not make any withdrawals from the savings account for a period of time (e.g., one year), a financial institution may provide a higher matching level (e.g., double the match from the prior year, increase the matching level for the subsequent year, and the like) In another example, when an account holder deposits large or certain types of funds (e.g., tax refund) into a savings account and does not withdraw the funds for a predefined period of time (e.g., one year), the institution may provide an increased matching/bonus level (e.g., double matching, increased interest rate yield) on the savings amount.

In another example in accordance with aspects of the disclosure, a financial institution may enforce a predefined maximum limit (e.g., $300) for the matching/bonus amount for a given period of time (e.g., one year). Meanwhile, the institution may match the transferred savings amount at 100% for an initial period of time (e.g., 3 months) and a lower matching level (e.g., 5%) thereafter.

Furthermore, to encourage savings, an account holder and financial institution may identify a period of time (e.g., one year) and a savings amount goal for the holder's savings amount. If the holder achieves the goal, the financial institution may reward the account holder by providing an increased matching level (e.g., double the match from the prior year, increase the matching level for the subsequent year, and the like)

In yet another example, when an account holder regularly pays (e.g., for one consecutive year) at least the minimum amount due on a credit card, a financial institution may increase the level of matching/bonus paid on transferred savings amount. As such, the financial institution encourages good financial management among its account holders. Furthermore, to encourage account holders to maintain a credit card and checking account (or debit card) with the financial institution, the institution may offer an increased matching/bonus level to an account holder commensurate with the amount of interest paid on the holder's credit card. In another embodiment, the financial institution may refund a portion (e.g., 1%, 5%, 20%) of the total amount of interest paid on the holder's credit card over a period of time (e.g., one year) for one or more reasons, including, for example, if the account holder regularly pays at least the minimum amount due on a credit card over the time period.

As explained throughout the disclosure herein, the matching amount may be deposited in a recipient account with a financial institution. Some examples of recipient accounts include savings accounts that have restrictions on the account holder's ability to withdraw funds without early withdrawal charges. In addition, the matching amount may be deposited in various different types of recipient accounts (e.g., gift card account, and the like) Furthermore, in some embodiments, the matching amount may be reward points applied towards airline frequent flier mile programs, or other reward-like programs.

In accordance with various aspects of the disclosure, the matching amount may be paid out at one or more times or regular intervals. For example, a financial institution may pay a bonus at the one-year anniversary of enrolling in the savings program on the balance on the one-year date. As such, an account holder that withdraws money prior to the one-year date may not achieve maximum matching/bonus. In another example, the matching amount may be paid at the end of each day. In yet another example, a matching amount may be paid in "near real-time" as transactions eligible for matching are received at computer system 101. In yet another example, matching amounts are paid out only after an aggregate match amount threshold (e.g., $10) has been reached. As such, a financial institution can reduce the number of transfers that are required to implement a savings program in accordance with aspects of the disclosure.

In another embodiment of the present disclosure, after the user selects the recipient accounts to enroll for receiving savings from the program, the server presents the user with an option to enroll in a service for receiving distribute notifications. If the user selects the distribute notification option, the server then presents to the user options for determining the threshold amount that triggers sending the distribute notifications to the user. The options for determining the threshold level for when the distribute notifications will be sent to the user may be based on an absolute monetary amount of savings from the program, a percentage of savings based on a goal selected by the user, a predetermined passage of time, such as a weekly or monthly distribute notification, or other criterion. When the notification threshold has been reached, the server may then send a notification to the user alerting the user that, among other things, the threshold savings amount has been reached.

Figure 7:
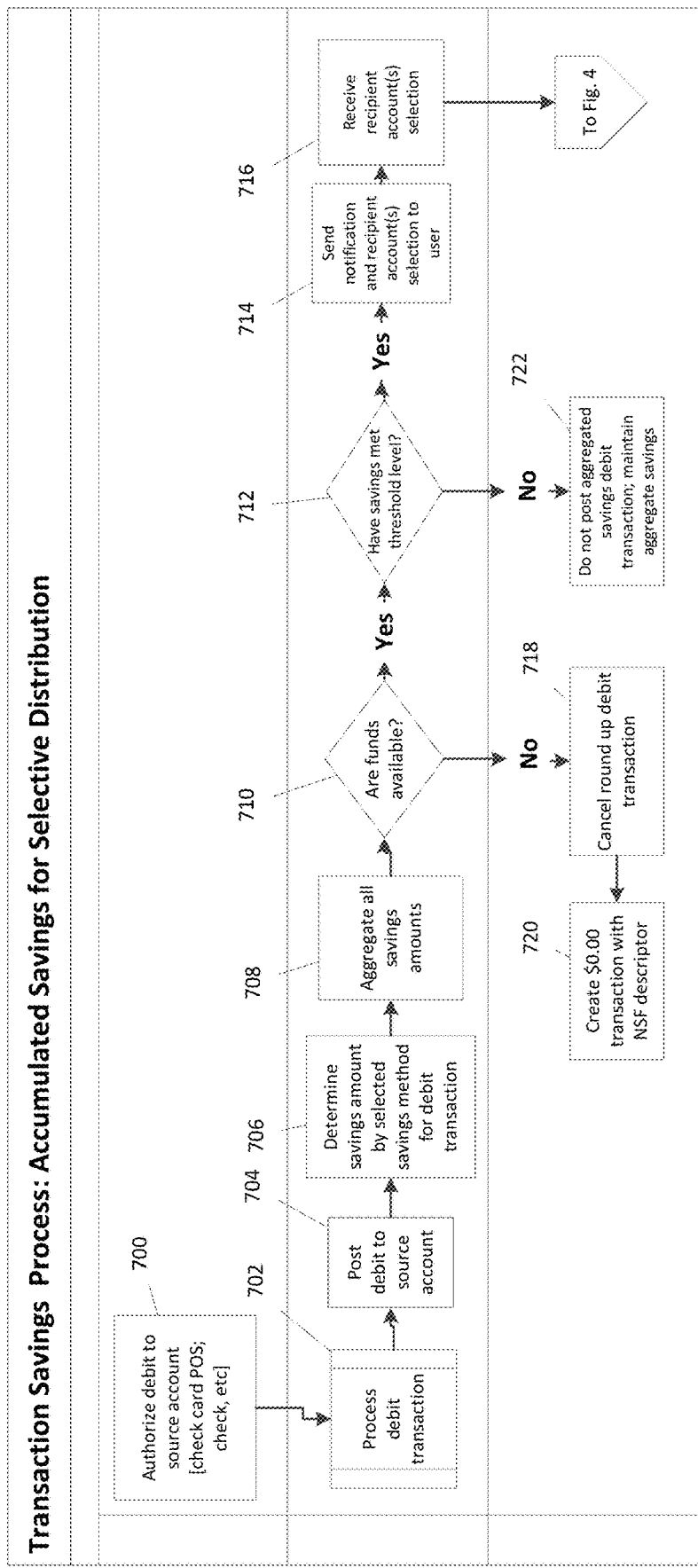
FIG. 7 illustrates a flowchart depicting a method of accumulated savings for selective distribution in accordance with aspects of the disclosure.

Referring to FIG. 7, in step 700, a debit to a source account (e.g., check card POS, check, and the like) is authorized.

In step 702, the debit transaction, such as a purchase at POS 162, disclosed in FIG. 4, using a debit card, may be processed.

In step 704, the debit transaction may be posted to the source account.

In step 706, the method of calculating the savings amount may then be determined. In one embodiment, the savings amount may be determined by either a round up, a discount, a merchant or product based savings, a whole monetary amount, a percentage based, a "treat yourself" method, or other criterion. In another embodiment, in reference to FIG. 4, computer server 101, in communication with the merchants 121, 122 or 123, and accompanying POS devices may determine whether a purchase by the user was a discount purchase.

In step 708, all round up or other savings amounts may be aggregated. This may occur on a daily basis. By aggregating the round ups for one daily posting, exceeding account limits of the source account can be avoided. In one embodiment, the daily posting occurs at the end of the day to further avoid exceeding account limits.

In step 710, a determination may be made if funds are available in the source account. If not, the aggregated round up debit transaction is cancelled (step 718) and a $0.00 transaction is created with a no funds in source account descriptor (step 720).

In step 712, the threshold savings level may be determined. In one embodiment of the present disclosure and in reference to FIG. 5, the distribute notification threshold is determined by selective distribution module 1242A calculating the aggregate savings amount that has not been disbursed to recipient accounts yet. If the threshold level has not been reached, computer system 101 may continue to aggregate savings amount without disbursement (step 722) to a recipient account until the distribute notification threshold has been reached. Upon reaching the distribute notification threshold amount, the selective distribution module 1242A may proceed to send the distribution notification and stores this information in memory.

In step 714, the distribution notification and recipient account selection may be sent to the user. In one embodiment of the present disclosure and in reference to FIG. 5, the distribution notifications are determined by a selective distribution module 1242A in computer system 101 (e.g., using processor 103A). Selective distribution module 1242A determines if the aggregated savings (step 708) stored in data 121A has met a predetermined threshold value as specified by a user in the preceding example. Selective distribution module 1242A may then send an encrypted distribution notification via a modem in communications module 109A through WAN 129 to the Internet, and finally to smartphone 171. Smartphone 171 receives the distribution notification via Internet through communications module 109B and stores the notification in memory 115B. Selective distribution module 1242B in smartphone 171, using processor 103B then initiates presenting the distribution notification via audio interface 222. Audio interface 222 of smartphone 171 receives the notification from selective distribution module 1242B, and the audio interface then converts the electrical notification into an audible signal to the user via speakers 224 of smartphone 171. After receiving the audible distribution notification, selective distribution module 1242B then presents a selection input options of recipient accounts for the user to select for distribution of savings. Selective distribution module 1242B may present the selection input options for recipient accounts via processor 103B communicating with touchscreen GUI 172 of communications module 109B of smartphone 171, to provide a graphical interface for the user to make a selection.

In step 716, the recipient account selections are received. In one embodiment of the disclosure and in reference to FIG. 5, smartphone 171 receives the recipient account selection. Once the user selects the recipient account to receive the distribute savings by touching the corresponding recipient account option via touchscreen GUI 172, that selection is transmitted through communications module 109B to selective distribution module 1242B, where it is then transmitted through communications module 109B to selective distribution module 1242A via the Internet (e.g., network 131) and communications module 109. Upon receiving the recipient account selection information, selective distribution module 1242A then processes, transforms, and transmits the distribute savings selection information through communications module 109 to a bank server 141 via WAN 129 and Internet (e.g., network 131). Bank server 141 receives the distribute savings selection information from selective distribution module 1242A. The distribute savings selection information provides instructions for the bank server 141 to pass on the information to deposit applications and credit engines. The deposit applications debit the savings distribution from the source account, and the credit engines verify the existence and status of the receiving account and create a credit transaction for the transferred savings amount to post to the recipient account in the next processing cycle.

Figure 17:
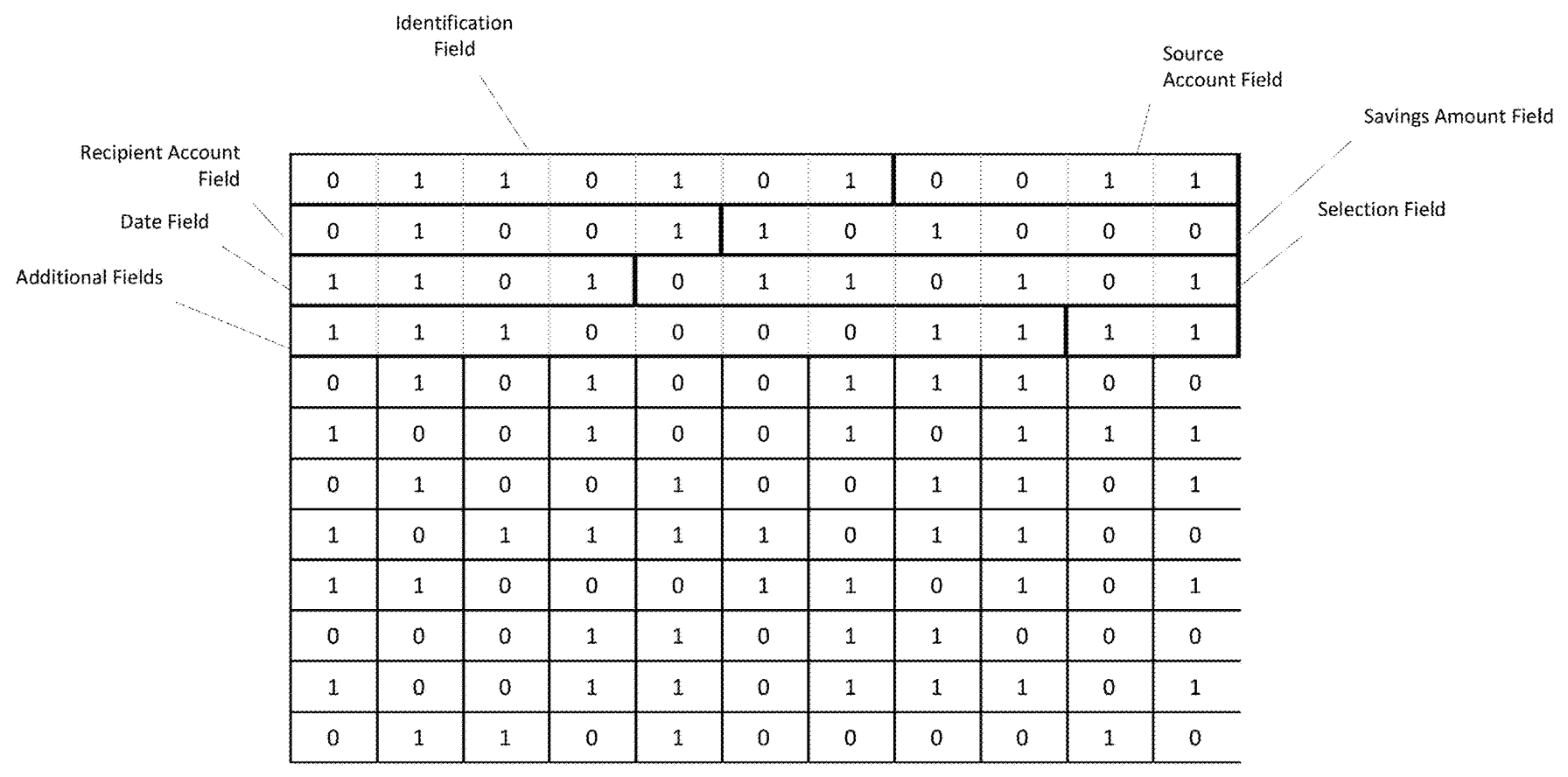

In a further embodiment and in reference to FIG. 5, the distribution notification information sent to the user's wireless device by selective distribution module 1242A may be transformed into a selective distribution message type. Selective distribution module 1242A may format the data in the selective distribution message type into an encrypted packet that when decrypted, may include a message identification field, source account fields, recipient account fields, savings amount field, date fields, and selection field, among other fields. As shown in FIG. 17, the selective distribution message type may be illustrated with the aforementioned fields and formalities.

In reference to FIG. 5, the message identification field when read by distribution selection modules 1242A or 1242B may identify the message as a selective distribution message type. The source account fields may provide information regarding the source accounts to draw the distribution savings from. Recipient account fields may provide information regarding the recipient account. The savings amount field provides information regarding the distribution savings. The date fields may provide the date range for which the savings aggregate for the distribution threshold notification is drawn from, the date of the distribution notification, the date of distribution selection by the user, the date the distribution savings were posted, among other dates. The selection field may provide information relating to the source accounts and recipient accounts that were selected for the distribution savings, as a user may identify multiple source and recipient accounts for a distribution savings. The fields may provide sufficient information so when parsed and transformed by distribution module 1242A and distribution module 1242B to provide banking server 141 or 151 the information needed to obtain any data requests of the selected source and recipient accounts without need for selective distribution modules 1242B to be present at the bank servers to process the data. At least one technological benefit to this arrangement is that the selective distribution module 1242B may separate multiple transfer requests into a plurality of messages that can be scaleably distributed to a plurality of banking servers for processing. As such, the processing load may be shared among a server farm of banking servers.

Additionally, the recipient account selection information sent by selective distribution module 1242B to selective distribution module 1242A may also be transformed into a selective distribution message type. Similarly to the embodiment described above, this selective distribution message type may be formatted by transforming and encrypting the data packets into a selective distribution message type containing message identification field, source account fields, recipient account fields, savings amount field, date fields, and selection fields, among other fields. This may allow the distribution selection modules 1242A to parse the recipient account selection information once received from distribution module 1242B, splice the data, repackage, and transmit the relevant data so as to send to bank servers 141 or 151 of the necessary financial institutions to perform the debits and credits to the selected source and recipient accounts without need for selective distribution modules 1242B to be present at the bank servers to process the data from distribution selection modules 1242A.

Additionally, as the distribution notification information and recipient account selection information may be transformed into selective distribution message types, bank servers 141 and 151 may also have selective distribution modules 1242B so as to process the selective distribution message types without need for selective distribution module 1242A in computer server 101 to transform the selective distribution message type into code readable by the bank servers without selective distribution modules 1242B. In this embodiment, bank servers 141 and 151 may then be able to transform the data for communicating with a variety of other bank and computer servers at other financial institutions and retail locations, among other computers.

One of ordinary skill in the art after review of the entirety disclosed herein and in reference to FIG. 5, will appreciate that various features and aspects of the disclosure allow the user to receive distribution notifications by other wireless devices besides smartphone 171. The user may also associate other devices with the source account to communicate with selective distribution module 1242A in computer system 101 for receiving distribution notifications and for allowing the user to select recipient accounts, such as a user's personal computer 161, tablet 181, or smartwatch 191. Any personal wireless device capable of communicating with computer server 101 and selective distribution module 1242A may be used.

In a further embodiment of the present disclosure, smartwatch 191 may receive distribution notifications from selective distribution module 1242A in computer server 101 via communications module 109B. Smartwatch 191 may not have selective distribution module 1242B, but upon receiving the distribution notifications in communications module 109B, directly present the notification to the user via a graphical message on the smartwatch GUI in communications module 109B, or as an audio alert through a speaker in communications module 109B in smartwatch 191. The smartwatch 191 may present any combination of graphical, audio, or vibration distribution notifications alerts to a user.

Further, smartwatch 191 may allow for the user to make a recipient account selection at the smartwatch touchscreen GUI 172 and then communicate that selection to selective distribution module 1242A via communications module 109B in smartwatch 191, or it may communicate with another wireless device for the user to make a recipient account selection. For example, upon receiving distribution notification from distribution module 1242A, the smartwatch alerts the user. Then, smartwatch 191 communicates the distribution notification with another wireless device of the user, such as tablet 181, which then presents the recipient account selection input to the user.

In accordance with various aspects of the disclosure and in reference to FIG. 5, the distribution notification presented to the user may be communicated in various forms. For example, after the wireless device of the user receives the distribution notification, it may present the notification via vibration of the wireless device. Selective distribution module 1242B of the wireless device, upon receiving the distribution notification, would send the notification signal to a motor within communications module 109B that activates the motor and causes vibration within the wireless device. In another example, the distribution module 1242B upon receiving the distribution notification would transmit a text or image graphical alert through a GUI of the communications module 109B.

Further, selective distribution module 1242B may receive the user input for selection of the recipient accounts through additional means. For example, upon presenting the user with recipient account selections through a GUI in communications module 109B of the wireless device, the user may select the recipient account through voice activation. Selective distribution module 1242B may transmit the recipient account selection information to the GUI via processor 103B with corresponding voice activation phrases for each account, such as "account A" or "grandson's account". When the user speaks one of the voice activation phrases for an account, a microphone within the communications module 109B may detect the phrase and then send that selection information to selective distribution module 1242B.

In another example, the user may select a recipient account through a GUI in the wireless device via a keyboard or mouse in communications module 109B. Still further, selective distribution module 1242B may have pre-selected recipient accounts stored in memory 115B that the user has selected at enrollment in the savings program, and selective distribution module 1242B will automatically select the pre-selected recipient account after sending a distribution notification to the user.

One of ordinary skill in the art after review of the entirety disclosed herein will appreciate that the user's mobile device may receive the recipient accounts information through a number of means. For example, in one embodiment, the selective distribution module 1242B of the wireless device may have the recipient account information stored on the mobile device in memory 115B. In this embodiment, upon receiving the distribution notification, selective distribution module 1242B of the wireless device would then retrieve the recipient accounts information form memory 115B to present the recipient account selection input to the user. In another embodiment, the selective distribution module 1242B receives the recipient account information from computer server 101 along with the distribution notification. The selective distribution module 1242A may encrypt the recipient account information and then transmit this information over the Internet (e.g., network 131) through communications module 109A to the wireless device. Once the wireless device has received the encrypted recipient account information, selective distribution module 1242B then decrypts the information and sends this information to communication module 109B for presenting to the user for selection. In a still further embodiment, the wireless device may communicate directly with bank server 141 for receiving the recipient account information.

In accordance with various aspects of the disclosure and in reference to FIG. 5, the selective distribution module 1242A may exist within a bank server 141 or 151 of a financial institution, such that the selective distribution module 1242A exists within memory 115A of bank server 141 or 151. Distribute notifications and recipient account selection information may then be transmitted directly between bank server 141 or 151 to the user's wireless device. When selective distribution module 1242A in bank server 141 or 151 receives the recipient account selection from the user's wireless device, selective distribution module 1242A through processor 103 then posts the debit of the distribution savings from the source account and posts the credit of the distribution savings to the recipient account in data 121.

Alternatively, the user's wireless device may not contain selective distribution module 1242B within memory 115B. Selective distribution module 1242A may transmit and present both selective distribution notifications and recipient account selections, as well as receive recipient account inputs from the user through the wireless device. Selective distribution module 1242A may communicate wirelessly with communications module 109B in the wireless device to directly send distribution notification signals to the user, as well as sending recipient account selection information directly to the user through communications module 109B. Additionally, when the user makes a recipient account selection, that selection may be transmitted directly from communications module 109B to the computers server 101 for processing by selective distribution module 1242A. In this sense, the user's wireless device is operating as a portal for presenting and receiving selective distribution information from selective distribution module 1242A without requiring selective distribution module 1242B on the wireless device.

In one embodiment of the present disclosure, computer server 101 presents an option for the user to enroll in a service for receiving additional savings notifications. The additional savings notification may prompt the user to add additional funds to the selected savings amounts. The additional amount may be added to a daily savings amount. In another embodiment, the additional savings amount may be added at other time frames, such as weekly or monthly. The user may select any whole monetary amount, among other amounts, to add to the savings round up amounts when prompted by an additional savings notification. The user may additionally select periodic time periods to send additional savings notifications to the user in the future.

In a further embodiment, the additional savings notification may be sent by computer server 101 in conjunction with sending the savings notification notifying the user that they are not reaching their savings goals. The server may also suggest an additional savings amount or additional savings method to add to the savings amounts or savings methods based on the users selected goal and the projection of achieving that goal within a selected time frame.

Figure 8:
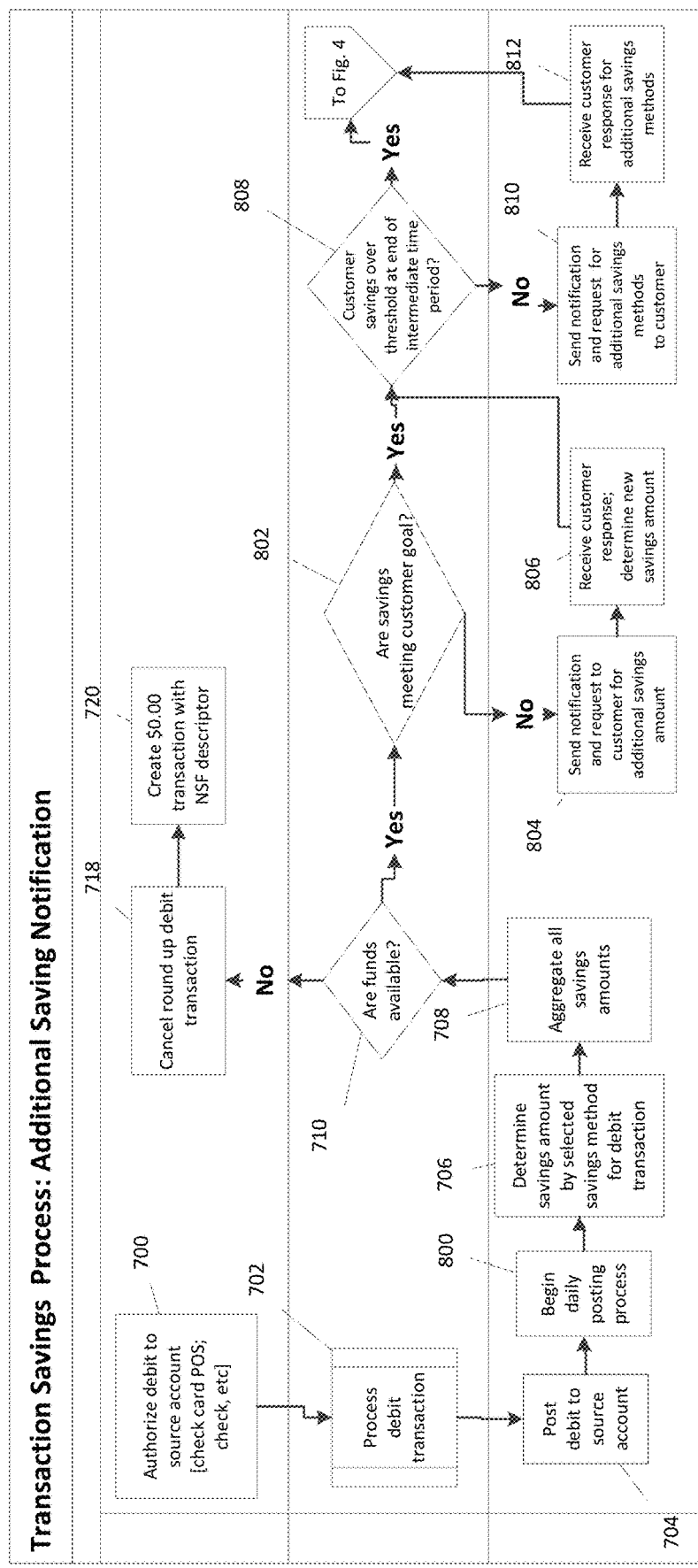
FIG. 8 illustrates a flowchart depicting a method of additional savings notifications in accordance with aspects of the disclosure.

Referring to FIG. 8, an embodiment of a computer implemented savings program for providing additional savings notifications is shown. In step 700, the debit to the source account (e.g., check card POS, check, and the like) selected at 102 is authorized.

In step 702, the debit transaction, such as a purchase at POS 162 disclosed in FIG. 4, using a debit card, may be processed.

In step 704, the debit transaction may be posted to the source account.

In step 800, the daily posting transaction begins.

In step 706, the method of calculating the savings amount may be determined. In one embodiment, the savings amount may be determined by either a round up, a discount, a merchant or product based savings, a whole monetary amount, a percentage based, a "treat yourself" method, or other criterion. In another embodiment, with reference to elements depicted in FIG. 4, the computer server 101, in communication with the merchants 164, 165 or 166, and accompanying POS devices 162 may determine whether a purchase by the user was a discount purchase.

In step 708, all round up or other amounts may be aggregated. This may occur on a daily basis. By aggregating the round ups for one daily posting, exceeding account limits of the source account can be avoided. In one embodiment, the daily posting may occur at the end of the day to further avoid exceeding account limits.

In step 710, a determination may be made if funds are available in the source account. If not, the aggregated round up debit transaction may be cancelled (step 718) and a $0.00 transaction is created with a no funds in source account descriptor (step 720).

In step 802, with reference to elements depicted in FIG. 5, the additional savings module 843A may determine if the savings are on track to meeting the user's savings goal. Additional savings module 843 determines the daily savings needed to meet the user's selected goal by the given time frame by the user. If the user is on track as of that day, then the additional savings module 843A may proceed to step 808. If the user is not on track, then additional savings module 843 may send a request for additional savings 804.

In step 804, the additional savings notification may be sent to the user. In one embodiment of the present disclosure, with reference to elements depicted in FIG. 5, the additional savings notifications may be determined by an additional savings module 843A in computer system 101 (e.g., using processor 103A). Additional savings module 843A determines if the aggregated savings 408 stored in data 121A has met a daily threshold value as specified by a user's end goals and calculated by additional savings module 843A in the preceding example. Additional savings module 843A may then send an encrypted additional savings notification via a modem in communications module 109A through WAN 129 to the Internet (e.g., network 131), and finally to smartphone 171. Smartphone 171 receives the additional savings notification via Internet (e.g., network 131) through communications module 109B and stores the notification in memory 115B. Additional savings module 843B in smartphone 171, using processor 103B then initiates presenting the additional savings notification via audio interface 222. Audio interface 222 of smartphone 171 receives the notification from additional savings module 843B, and the audio interface may then converts the electrical notification into an audible signal to the user via speakers 224 of smartphone 171. After receiving the audible additional savings notification, additional savings module 843B may then presents a selection input options for additional savings for the user to select to add to the savings amount. Additionally, savings module 843B may present the selection input options for additional savings via touchscreen GUI 172 by processor 103B communicating with communications module 109B of smartphone 171 to provide a graphical interface for the user to make a selection.

In step 806, the additional savings selections may be received. In one embodiment of the disclosure, with reference to elements depicted in FIG. 5, smartphone 171 receives the additional savings selections. Once the user selects the additional savings selections by touching the corresponding additional savings option via touchscreen GUI 172, that selection may be transmitted through communications module 109B to additional savings module 843B, where it is then transmitted through communications module 109B to additional savings module 843A of computer server 101 via the Internet (e.g., network 131) and communications module 109. Upon receiving the additional savings selections, additional savings module 843A may then determine a new savings amount.

In step 808, the additional savings module 843A may determine if the user is on track to meet a savings goal based on an intermediate time period. With reference to elements depicted in FIG. 5, the intermediate time period may be a monthly time period since enrollment, in which additional savings module 843A checks the total savings since enrollment and determines if the user is on track to reach the final savings goal based on the user's intermediate time period, which in one embodiment may be a monthly savings total. If additional savings module 843A determines that the user has not met the intermediate savings goal, the additional savings module 843A may send an additional savings method notification 810. If the user has met the intermediate savings goal, but required additional savings request 804, additional savings module 843A may transform and transmits the additional savings selections information through communications module 109 to a bank server 141 via WAN 129 and Internet (e.g., network 131). Bank server 141 may receive the additional savings selections information from additional savings module 843A. Additional savings module 843A provides instructions for bank server 141 to pass on the information to deposit applications for debiting the additional savings selections information from the source account and to credit engines for verifying the existence and status of the receiving account. Bank server 141 may then create a credit transaction for the additional savings selections information to post to the recipient account in the next processing cycle. If the user's savings are on track and did not require additional savings notification 804 or additional savings method notification 801, additional savings module 843A may transmit the savings amount through communications module 109 to a bank server 141 via WAN 129 and Internet (e.g., network 131) for posting the savings amount as in the proceeding example described above.

In step 810, the additional savings method notification may be sent to the user. In one embodiment of the present disclosure and with reference to elements depicted in FIG. 5, the additional savings method notification may be determined by an additional savings module 843A in computer system 101 (e.g., using processor 103). Additional savings module 843A may then send an encrypted additional savings method notification via a modem in communications module 109A through WAN 129 to the Internet (e.g., network 131), and finally to smartphone 171. Smartphone 171 receives the additional savings method notification via Internet (e.g., network 131) through communications module 109B and stores the notification in memory 115B. Additional savings module 843B in smartphone 171, using processor 103B may then initiate presenting the additional savings method notification via audio interface 222. Audio interface 222 of smartphone 171 receives the notification from additional savings module 843B, and the audio interface may then convert the electrical notification into an audible signal to the user via speakers 224 of smartphone 171. After receiving the audible additional savings method notification, additional savings module 843B may then present a selection input option for additional savings method for the user to select to add or alter the savings method of 406 and 804. Additional savings module 843B may present the selection input options for additional savings methods via touchscreen GUI 172 by processor 103B communicating with communications module 109B of smartphone 171 to provide a graphical interface for the user to make a selection.

In step 812, the additional savings method selections may be received. In one embodiment of the disclosure and with reference to elements depicted in FIG. 5, smartphone 171 receives the additional savings method selections. Once the user selects the additional savings method selections by touching the corresponding additional savings method option via touchscreen GUI 172, those selections may be transmitted through communications module 109B to additional savings module 843B, where it is then transmitted through communications module 109B to additional savings module 843A of computer server 101 via the Internet (e.g., network 131) and communications module 109. Upon receiving the additional savings method selections, additional savings module 843A may then determine a new savings method amount. Additional savings module 843A may then transmit the savings amount through communications module 109 to a bank server 141 via WAN 129 and Internet (e.g., network 131) for posting the savings amount as in the proceeding example described above.

One of ordinary skill in the art after review of the present disclosure will appreciate that various features and aspects of the disclosure may allow additional savings module 843A to present a number of additional savings amounts for the user to select at the wireless device in step 804 and 806. The additional saving amounts may be an amount recommended by additional savings module 843A that is calculated to meet the user's daily savings amount to reach the user's selected goal during enrollment. Further, the wireless device in communication with additional savings module 843A may present the option for the user to specify a custom additional savings amount. The additional savings amount may be a whole monetary amount, a percentage of the user's savings amount, or any other criterion that a banking server may be able to process.

Similarly, and with reference to elements depicted in FIG. 5, additional savings module 843A in communication with a wireless device of the user may present a number of additional savings methods for the user to select at the wireless device in step 810 and 812. Additional savings module 843A may present additional savings methods that have been described at previous step 406, such as discount savings, product or merchant based savings, whole monetary amount savings, round up savings, or other methods of savings amounts. Additional savings module 843A may calculate and recommend preferred savings methods for the user based on obtaining a user's specified savings goal.

In one embodiment, the additional savings notification sent to the user's wireless device by additional savings module 843A may be transformed into an additional savings message type. Additional savings module 843A may format the data in the additional savings message type into an encrypted packet that when decrypted, may include a message identification field, source account fields, recipient account fields, savings amount fields, date fields, and selection fields, among other fields. As shown in FIG. 17, the additional savings message type is illustrated with the aforementioned fields and formalities.

Referring to FIG. 17, the message identification field 1700 when read by additional savings module 843A or 843B, may identify the message as an additional savings message type. The source account field 1702 may provide information regarding the source accounts to draw the additional savings from. Recipient account field 1704 may provide information regarding the recipient account. The savings amount field 1706 may provide information regarding the additional savings options. The date field 1708 may provide the date range for which the savings aggregate for the distribution threshold notification is drawn from, the date of the distribution notification, the date of distribution selection by the user, the date the distribution savings were posted, among other dates. The selection field 1710 may provide information relating to the source accounts and recipient accounts that were selected for the distribution savings, as a user may identify multiple source and recipient accounts for a distribution savings. Additional fields 1712 may provide additional information regarding multiple additional savings transactions between multiple source and recipient accounts. Additional savings module 843A or additional savings module 843B may parse and transform the additional savings message type before being sent to banking server 141 or 151. This conversion of the additional savings message into a readable format by bank servers 141 and 151 obviates the need for selective additional savings module 843B to be present at the bank servers to process the message. Further, the information within the fields of the additional savings message may provide sufficient information, so when parsed and transformed by additional savings module 843A or additional savings module 843B, provide sufficient information for bank servers 141 or 151 to create or update a savings debit or credit transaction without need to query additional data from the selected source and recipient accounts. At least one technological benefit to this arrangement is that the selective distribution module 1242B may separate multiple transfer requests into a plurality of messages that can be scaleably distributed to a plurality of banking servers for processing. As such, the processing load may be shared among a server farm of banking servers.

Additionally, the additional savings selection information sent by additional savings module 843B to additional savings module 843A may also be transformed into an additional savings message type. Similarly to the embodiment described above, this additional savings message type may be formatted by transforming and encrypting the data packets into an additional savings message type that may contain message identification field, source account fields, recipient account fields, savings amount fields, date fields, and selection fields, among other fields as described in the proceeding example. This may allow the distribution selection modules 1242A to parse the recipient account selection information once received from distribution module 1242B, splice the data, repackage, and transmit the relevant data so as to send to bank servers 141 or 151. Bank servers 141 or 151 may then perform the debits and credits to the selected source and recipient accounts without need for additional savings module 843B to be present at the bank servers to process the data from additional savings module 843A.

In another embodiment, in reference to FIG. 5, bank servers 141 and 151 may also have additional savings module 843B so as to process the additional savings message type without need for additional savings module 843A in computer server 101 to transform the message type into code readable by the bank servers without additional savings modules 843B. In this embodiment, bank servers 141 and 151 may then be able to transform the data for communicating with a variety of other bank and computer servers at other financial institutions and retail locations, among other computers.

One of ordinary skill in the art after review of the present disclosure will appreciate that various features and aspects of the disclosure allow the user to receive additional savings and additional savings method notifications by other wireless devices besides smartphone 171. The user may also associate other devices with the source account to communicate with additional savings module 843A in computer system 101 for receiving additional savings and additional savings method notifications and for allowing the user to select additional savings and additional savings methods, such as a user's personal computer 161, tablet 181, or smartwatch 191. Any personal wireless device capable of communicating with computer server 101 and additional savings module 843A may be used.

In a further embodiment of the present disclosure, smartwatch 191 may receive additional savings or additional savings method notifications from additional savings module 843A in computer server 101 via communications module 109B. Smartwatch 191 may not have additional savings module 843B, but upon receiving the additional savings or additional savings method notifications in communications module 109B, directly present the notifications to the user via a graphical message on the smartwatch GUI in communications module 109B, or as an audio alert through a speaker in communications module 109B in smartwatch 191. The smartwatch 191 may present any combination of graphical, audio, or vibration distribution notifications alerts to a user.

Further, smartwatch 191 may allow for the user to make an additional savings or additional savings method selection at the smartwatch touchscreen GUI 172 and then communicate that selection to additional savings module 843A via communications module 109B in smartwatch 191, or it may communicate with another wireless device for the user to make an additional savings or additional savings method selection. For example, upon receiving additional savings or additional savings method selection from additional savings module 843A, the smartwatch alerts the user. Then, smartwatch 191 communicates the additional savings or additional savings method notification with another wireless device of the user, such as tablet 181, which then presents additional savings or additional savings method selection input to the user.

In accordance with various aspects of the disclosure, the additional savings or additional savings method notifications presented to the user may be communicated in various forms. For example, after the wireless device of the user receives the notification, it may present the notification via vibration of the wireless device. Additional savings module 843B of the wireless device, upon receiving the additional savings or additional savings method notification, would send the notification signal to a motor within communications module 109B that activates the motor and causes vibration within the wireless device. In another example, the additional savings module 843B upon receiving the additional savings or additional savings method notification would transmit a text or image graphical alert through a GUI of the communications module 109B.

Further, additional savings module 843B may receive the user input for selection of the additional savings or additional savings method through additional means. For example, upon presenting the user with additional savings or additional savings method selections through a GUI in communications module 109B of the wireless device, the user may select the recipient account through voice activation. Additional savings module 843B may transmit the additional savings or additional savings method selection information to the GUI via processor 103B with corresponding voice activation phrases for each additional savings or additional savings method, such as "five dollar additional amount" or "merchant based savings method". When the user speaks one of the voice activation phrases for an account, a microphone within the communications module 109B may detect the phrase and then send that selection information to additional savings module 843B.

In another example, the user may select a recipient account through a GUI in the wireless device via a keyboard or mouse in communications module 109B.

One of ordinary skill in the art after review of the present disclosure will appreciate that the user's mobile device may receive the additional savings information through a number of means. For example, in one embodiment and with reference to elements depicted in FIG. 5, the additional savings module 843B of the wireless device may have the additional savings information stored on the mobile device in memory 115B. In this embodiment, upon receiving the additional savings or additional savings method notification, additional savings module 843B of the wireless device would then retrieve the additional savings or additional savings method information from memory 115B to present the additional savings or additional savings method input to the user. In another embodiment, the additional savings module 843B receives the additional savings or additional savings method information from computer server 101 along with the additional savings or additional savings method notification. The additional savings module 843A may encrypt the additional savings or additional savings method information and then transmit this information over the Internet (e.g., network 131) through communications module 109A to the wireless device. Once the wireless device has received the encrypted additional savings or additional savings method information, additional savings module 843B then decrypts the information and sends this information to communication module 109B for presenting to the user for selection. In a still further embodiment, the wireless device may communicate directly with bank server 141 for receiving the additional savings or additional savings method information.

In accordance with various aspects of the disclosure, the additional savings module 843A may exist within a bank server 141 or 151 of a financial institution, such that the additional savings module 843A exists within memory 115A of bank server 141 or 151. Additional savings or additional savings method information may then be transmitted directly between bank server 141 or 151 to the user's wireless device. When additional savings module 843A in bank server 141 or 151 receives the additional savings or additional savings method information from the user's wireless device, additional savings module 843A through processor 103 then posts the debit of the additional savings from the source account and posts the credit of the additional savings to the recipient account in data 121.

Alternatively, the user's wireless device may not contain additional savings module 843B within memory 115B. Additional savings module 843A may transmit and present both additional savings and additional savings method notifications, as well as receive additional savings or additional savings method inputs from the user through the wireless device. Additional savings module 843A may communicate wirelessly with communications module 109B in the wireless device to directly send additional savings or additional savings method notification signals to the user. Further, when the user makes an additional savings or additional savings method selection, that selection may be transmitted directly from communications module 109B to the computers server 101 for processing by additional savings module 843A. In this sense, the user's wireless device is operating as a portal for presenting and receiving additional savings or additional savings method information from additional savings module 843A without requiring additional savings module 843B on the wireless device.

In one embodiment of the present disclosure, the user may enroll in a service to receive savings goal indicators. If the user enrolls in the savings goal indicator service, computer system 101 may periodically determine the total savings amounts saved from the source account since the user enrolled, and compare the total amounts to the users selected goal. If the server determines that the user has not reached their goal or is not on track to reach their goal, the server may send a savings notification alert to the user. In a further embodiment, the savings notification alert may be sent from computer system 101 to the users selected device, and the alert may be voice activated, text, vibration, audio, or a graphical prompt. Alternatively, the server may also determine if the user is on track to reach their goal by determining if the user has reached any identified intermediate goals, or the server may determine if the user is on track based on the a projection from the time remaining to reach the goal and the amount of total savings accumulated.

In another embodiment of the present disclosure, computer system 101 may periodically send savings notifications updating the user on the amount they have saved in the program and/or the progress the user has made toward achieving their savings goal. Computer server 101 may automatically send updates periodically, or based on a time frame selected by the user.

Figure 9:
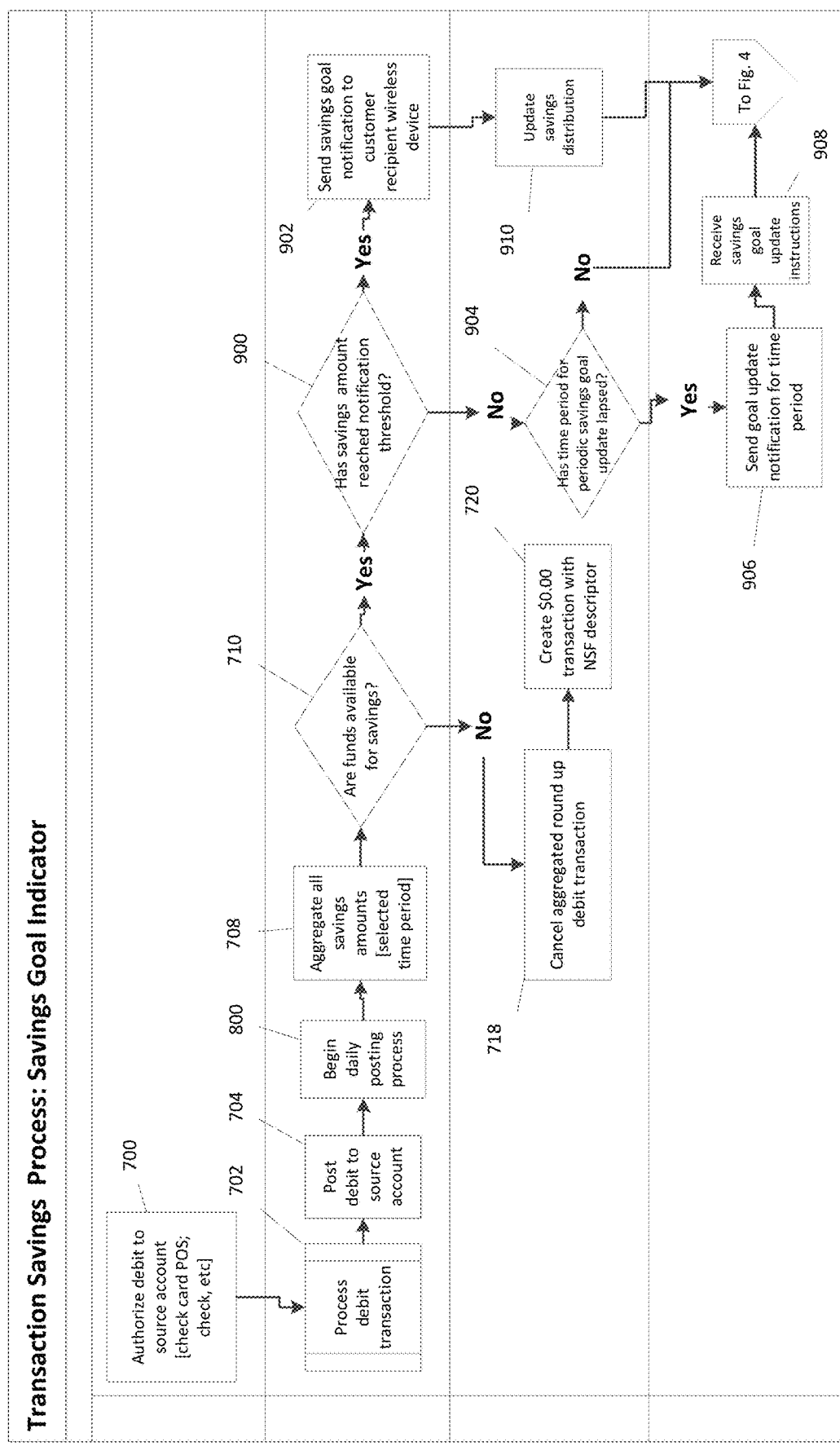
FIG. 9 illustrates a flowchart depicting a method of a savings goal indicator in accordance with aspects of the disclosure.

Referring to FIG. 9, an embodiment of a computer implemented savings program for providing a savings goal indicator is shown. In step 700, the debit to a source account (e.g., check card POS, check, and the like) is authorized.

In step 702, the debit transaction, such as a purchase at POS 162 using a debit card, may be processed.

In step 704, the debit transaction may be posted to the source account.

In step 800, the daily posting transaction begins.

In step 708, all round up or other amounts may be aggregated. This may occur on a daily, weekly, or other time basis. By aggregating the round ups for one daily or other selected time period for posting, exceeding account limits of the source account can be avoided. In one embodiment, the daily posting may occur at the end of the day to further avoid exceeding account limits.

In step 710, a determination may be made if funds are available in the source account. If not, the aggregated round up debit transaction may be cancelled (step 718) and a $0.00 transaction is created with a no funds in source account descriptor (step 720).

In step 900, the savings goal module 944A may determine if the savings amount has reached a savings goal notification threshold. Savings goal module 944A determines the use's total savings amount to date, and compares that savings amount to the notification threshold. The notification threshold may be determined by the user's savings goal, including reaching certain percentages of the savings goal, as well as the end savings goal. If the user has reached a savings goal notification threshold, then savings goal module 944A may proceed to step 902 to notify the user. If the user has not reached the savings goal notification threshold, then savings goal module 944A proceeds to step 904.

In step 902, savings goal module 944A may send a savings goal notification to the user. In one embodiment of the present disclosure as disclosed by FIG. 5, savings goal module 944A may send an encrypted savings goal notification via a modem in communications module 109A through WAN 129 to the Internet (e.g., network 131), and finally to smartphone 171. Smartphone 171 receives the savings goal notification via Internet (e.g., network 131) through communications module 109B and stores the notification in memory 115B. Savings goal module 944B in smartphone 171, using processor 103B then initiates presenting the savings goal notification via audio interface 222. Audio interface 222 of smartphone 171 receives the notification from savings goal module 944B, and the audio interface may then convert the electrical notification into an audible signal to the user via speakers 224 of smartphone 171.

In step 904, the savings goal module 944A may determine if the time period has lapsed for the user to meet the periodic save goal. In one embodiment of the present disclosure and with reference to elements depicted in FIG. 5, savings goal module 944A may determine if a time period has lapsed for sending a periodic savings goal notification. Savings goal module 944A may retrieve this information stored in memory 115A providing the time period between savings goal updates, based on the users selected savings goal during enrollment. If savings goal module 944A determines that the time period for a savings goal update notification has lapsed, it may send a notification to the user.

In step 906, the savings goal module 944A may send a savings goal update notification to the user. In one embodiment of the present disclosure and with reference to elements depicted in FIG. 5, savings goal module 944A may send an encrypted savings goal update notification via a modem in communications module 109A through WAN 129 to the Internet (e.g., network 131), and finally to smartphone 171. Smartphone 171 receives the savings goal update notification via Internet (e.g., network 131) through communications module 109B and stores the notification in memory 115B. Savings goal module 944B in smartphone 171, using processor 103B then initiates presenting the savings goal update notification via audio interface 222. Audio interface 222 of smartphone 171 receives the notification from savings goal module 944B, and the audio interface may then convert the electrical notification into an audible signal to the user via speakers 224 of smartphone 171. After receiving the audible savings goal update notification, savings goal module 944B may then present a selection input options for updating the user's savings goal as defined by the user at enrollment. Savings goal module 944B may present the selection input options for updating their savings goals via touchscreen GUI 172 by processor 103B communicating with communications module 109B of smartphone 171 to provide a graphical interface for the user to make a selection.

In step 908, the savings goal update selection may be received. In one embodiment of the disclosure and with reference to elements depicted in FIG. 5, smartphone 171 receives the savings goal update selection. Once the user selects the savings goal update selections by touching the corresponding savings goal update options via touchscreen GUI 172, that selection may be transmitted through communications module 109B to savings goal module 944B, where it is then transmitted through communications module 109B to savings goal module 944A of computer server 101 via the Internet (e.g., network 131) and communications module 109. Upon receiving the savings goal update selection, savings goal module 944B may then determine a new savings amount notification threshold 900.

In step 910, the savings goal module 944A updates the savings distribution to the user's recipient accounts. In the case where the user has identified multiple recipient accounts to enroll in the savings program or multiple savings goals, the savings goal module 944A determines what percentage of the savings may go to each recipient account for the savings. In another embodiment, where savings goal module 944A determines that one savings goal has been reached, savings goal module 944A may then provide banking server 141 or 151 information so as to divert additional savings into other recipient accounts or other savings goals selected by the user.

One of ordinary skill in the art after review of the present disclosure will appreciate that various features and aspects of the disclosure may allow savings goal module 944A to present a number of savings goal selections for the user to select at the wireless device in step 906. The savings goal selections may be a recommended periodic savings goal determined by savings goal module 944A that is calculated to meet the user's selected end goal during enrollment. Further, the wireless device in communication with additional savings module 843A may present the option for the user to specify a custom periodic or end goal savings amount. Still further, in another embodiment of the present disclosure, the user may select multiple savings goals for multiple recipient accounts, such that different recipient accounts may have different savings goals and different savings notification thresholds, and also different periodic savings goal update time periods. When presented with a savings goal update notification as in step 906, the user may update and alter the savings goals, notification amounts, or periodic update time frames for different recipient accounts at step 908 of the present disclosure.

In one embodiment, the savings goal update notification sent to the user's wireless device by savings goal module 944A may be transformed into a savings goal update message type. Savings goal module 944A may format the data in the savings goal update message type into an encrypted packet that when decrypted, may include a message identification field, source account fields, recipient account fields, savings goal fields, date fields, and selection fields, among other fields. As shown in FIG. 17, the savings goal update message type may be illustrated with the aforementioned fields and formalities.

Referring to FIG. 17, the message identification field 1700, when read by savings goal module 944A or 944B, may identify the message as a savings goal update message type. The source account field 1702 may provide information regarding the source accounts connected to determining the savings totals and savings goals from. The recipient account field 1704 may provide information relating to the recipient accounts connected to receiving the savings amounts toward the user's savings goals. The savings goal field 1714 provides information regarding the additional savings options. The date field 1708 may provide the date range for which the savings aggregate for the savings goal notifications are drawn from, the date of the savings goal notifications, the date of savings goal selections by the user, and the date the savings goals were reached, among other dates. The selection field 1710 may provide information relating to the source accounts and recipient accounts that were selected for the savings goals, as a user may identify multiple source and recipient accounts for a distribution savings. Referring to elements disclosed in FIG. 5, savings goal module 944A or 944B may parse and transform the savings goal update message before being sent to banking server 141 or 151. This conversion of the savings goal update message into a readable format by bank servers 141 and 151 obviates the need for savings goal module 944B to be present at the bank servers to process the message. Further, the information within the fields of savings goal update message may provide sufficient information, so when parsed and transformed by savings goal module 944A or savings goal module 944B, provide sufficient information for bank servers 141 or 151 to create or update savings debit or credit transactions between source and recipient accounts without need to query additional data from the selected source and recipient accounts. At least one technological benefit to this arrangement is that the savings goal module 944B may separate multiple savings update requests into a plurality of messages that can be scaleably distributed to a plurality of banking servers for processing. As such, the processing load may be shared among a server farm of banking servers.

In another embodiment, bank servers 141 and 151 may also have savings goal module 944B so as to process the savings goal update message type without need for savings goal module 944A in computer server 101 to transform the message type into code readable by the bank servers without savings goal module 944B. In this embodiment, bank servers 141 and 151 may then be able to transform the data for communicating with a variety of other bank and computer servers at other financial institutions and retail locations, among other computers.

One of ordinary skill in the art after review of the present disclosure will appreciate that various features and aspects of the disclosure allow the user to receive savings goal and savings goal update notifications by other wireless devices besides smartphone 171. The user may also associate other devices with the source account to communicate with savings goal module 944A in computer system 101 for receiving savings goal and savings goal update notifications and for allowing the user to select savings goal updates, such as a user's personal computer 161, tablet 181, or smartwatch 191. Any personal wireless device capable of communicating with computer server 101 and savings goal module 944A may be used.

In a further embodiment of the present disclosure, smartwatch 191 may receive savings goal and savings goal update notifications from savings goal module 944A in computer server 101 via communications module 109B. Smartwatch 191 may not have savings goal module 944B, but upon receiving the savings goal or savings goal update notifications in communications module 109B, directly present the notifications to the user via a graphical message on the smartwatch GUI in communications module 109B, or as an audio alert through a speaker in communications module 109B in smartwatch 191. The smartwatch 191 may present any combination of graphical, audio, vibration, or other method of distribution notifications alerts to a user.

Further, smartwatch 191 may allow for the user to make a savings goal update selection at the smartwatch touchscreen GUI 172 and then communicate that selection to savings goal module 944A via communications module 109B in smartwatch 191, or communicate with another wireless device for the user to make a savings goal update selection. For example, upon receiving a savings goal update selection from savings goal module 944A, the smartwatch alerts the user. Then, smartwatch 191 communicates the savings goal update notification with another wireless device of the user, such as tablet 181, which then presents savings goal update selection input to the user.

In accordance with various aspects of the disclosure, the savings goal and savings goal update notifications presented to the user may be communicated in various forms. For example, after the wireless device of the user receives the notification, it may present the notification via vibration of the wireless device. Savings goal module 944B of the wireless device, upon receiving the savings goal and savings goal update notification, would send the notification signal to a motor within communications module 109B that activates the motor and causes vibration within the wireless device. In another example, the savings goal module 944B upon receiving the savings goal and savings goal update notification would transmit a text or image graphical alert through a GUI of the communications module 109B.

Further, savings goal module 944B may receive the user input for selection of the savings goal update through additional means. For example, upon presenting the user with savings goal update selections through a GUI in communications module 109B of the wireless device, the user may select the savings goal update amount through voice activation. Savings goal module 944B may transmit the savings goal update selection information to the GUI via processor 103B with corresponding voice activation phrases for each savings goal update, such as "five hundred dollars," or "option A". When the user speaks one of the voice activation phrases for an account, a microphone within the communications module 109B may detect the phrase and then send that selection information to savings goal module 944B.

In another example, the user may select a recipient account through a GUI in the wireless device via a keyboard or mouse in communications module 109B.

One of ordinary skill in the art after review of the present disclosure will appreciate that the user's mobile device may receive the savings goal information through a number of means. For example, in one embodiment, the savings goal module 944B of the wireless device may have the savings goal information stored on the mobile device in memory 115B. In this embodiment, upon receiving the savings goal or savings goal update notification, savings goal module 944B of the wireless device would then retrieve the savings goal and savings goal update information from memory 115B to present the savings goal and savings goal update selection input options to the user. In another embodiment, savings goal module 944B receives the savings goal and savings goal update information from computer server 101 along with the savings goal or savings goal update notification. The savings goal module 944A may encrypt the savings goal or savings goal update information and then transmit this information over the Internet (e.g., network 131) through communications module 109A to the wireless device. Once the wireless device has received the encrypted savings goal or savings goal update information, savings goal module 944B then decrypts the information and sends this information to communication module 109B for presenting to the user for selection. In a still further embodiment, the wireless device may communicate directly with bank server 141 for receiving the savings goal or savings goal update information.

In accordance with various aspects of the disclosure, savings goal module 944A as part of computer system 101 may exist within a bank server 141 or 151 of a financial institution, such that savings goal module 944A exists within memory 115A of bank server 141 or 151. Additional savings or additional savings method information may then be transmitted directly between bank server 141 or 151 to the user's wireless device. When savings goal module 944A in bank server 141 or 151 receives the additional savings or additional savings method information from the user's wireless device, savings goal module 944A through processor 103 then posts the debit of the additional savings from the source account and posts the credit of the additional savings to the recipient account in database 121A.

Alternatively, the user's wireless device may not contain savings goal module 944B within memory 115B. Savings goal module 944A may transmit and present both additional savings and additional savings method notifications, as well as receive additional savings or additional savings method inputs from the user through the wireless device. Savings goal module 944A may communicate wirelessly with communications module 109B in the wireless device to directly send additional savings or additional savings method notification signals to the user. Further, when the user makes an additional savings or additional savings method selection, that selection may be transmitted directly from communications module 109B to the computers server 101 for processing by savings goal module 944B. In this sense, the user's wireless device is operating as a portal for presenting and receiving additional savings or additional savings method information from savings goal module 944A without requiring additional savings module 843B on the wireless device.

In one embodiment, the user may enroll in a merchant or product based saving method service. The savings amount may be determined by a merchant or product based savings method. The merchant or product savings method may be based on funds saved from spending less on a non-preferred merchant or product compared to a user's preferred or historical purchasing behavior for analogous products or merchants. In one example, if a user typically purchases a preferred product, such as a preferred brand and type of cup of coffee substituting that purchase for a less expensive but similar cup of coffee would create a savings between the price of preferred cup of coffee and the price from the less expensive cup of coffee. Those savings may be the product savings amount. Referring to FIG. 5, The desired product may be based on user input to computer system 101, where the user can input from a personal device, such as personal computer 116, tablet 181, smartphone 171, and smartwatch 191 their preferred product purchases for a merchant product module 1045A in computer system 101 to compare to. In another embodiment, merchant product module 1045A may monitor the historical spending behavior of the user to determine future merchant or product based savings amount. When a user makes a purchase through POS 162 or another device capable of making a purchase in communication with computer system 101, merchant product module 1045A in computer system 101 may record the purchase amount and specific merchant and product, and accumulate historical spending amounts for types of products. Merchant product module 1045A in computer system 101 may also determine if the user has saved money based on comparing expenditures from one time period to another from a particular merchant. For example, in one embodiment, merchant product module 1045A could track monthly energy costs for heating or cooling a home to an energy company. Based on historical comparisons from previous months, merchant product module 1045 may determine a merchant based savings amount compared to the costs from that month in prior years.

In another embodiment of the present disclosure, the user may enroll in a merchant or product blacklisting service. Merchant product module 1045A in computer system 101 may blacklist particular merchants or products to force user savings by requiring less expensive alternatives. Computer system 101 may present the user with an option to enroll in merchant or product based savings in addition to other savings methods. If the user chooses to enroll in merchant or product based savings, merchant product module 1045A may present the user with the option of entering desired products or merchants that it wishes to blacklist. If the user enters products or merchants it wants to block, merchant product module 1045A may blacklist those products or merchants to keep the user from purchasing those particular products or all products from those blacklisted merchants from the user's source account. If the user does not select products or merchants it wishes to block, merchant product module 1045A may track historical spending and periodically send blacklist notifications to the user suggesting products or merchants the user may wish to blacklist to increase savings. In another embodiment of the present disclosure, merchant product module 1045A may track historical spending and the merchant or product SKU numbers. Merchant product module 1045A may block certain merchants or products based on SKU numbers, or may send notifications for suggested products or merchants to block based on SKU numbers.

Figure 10:
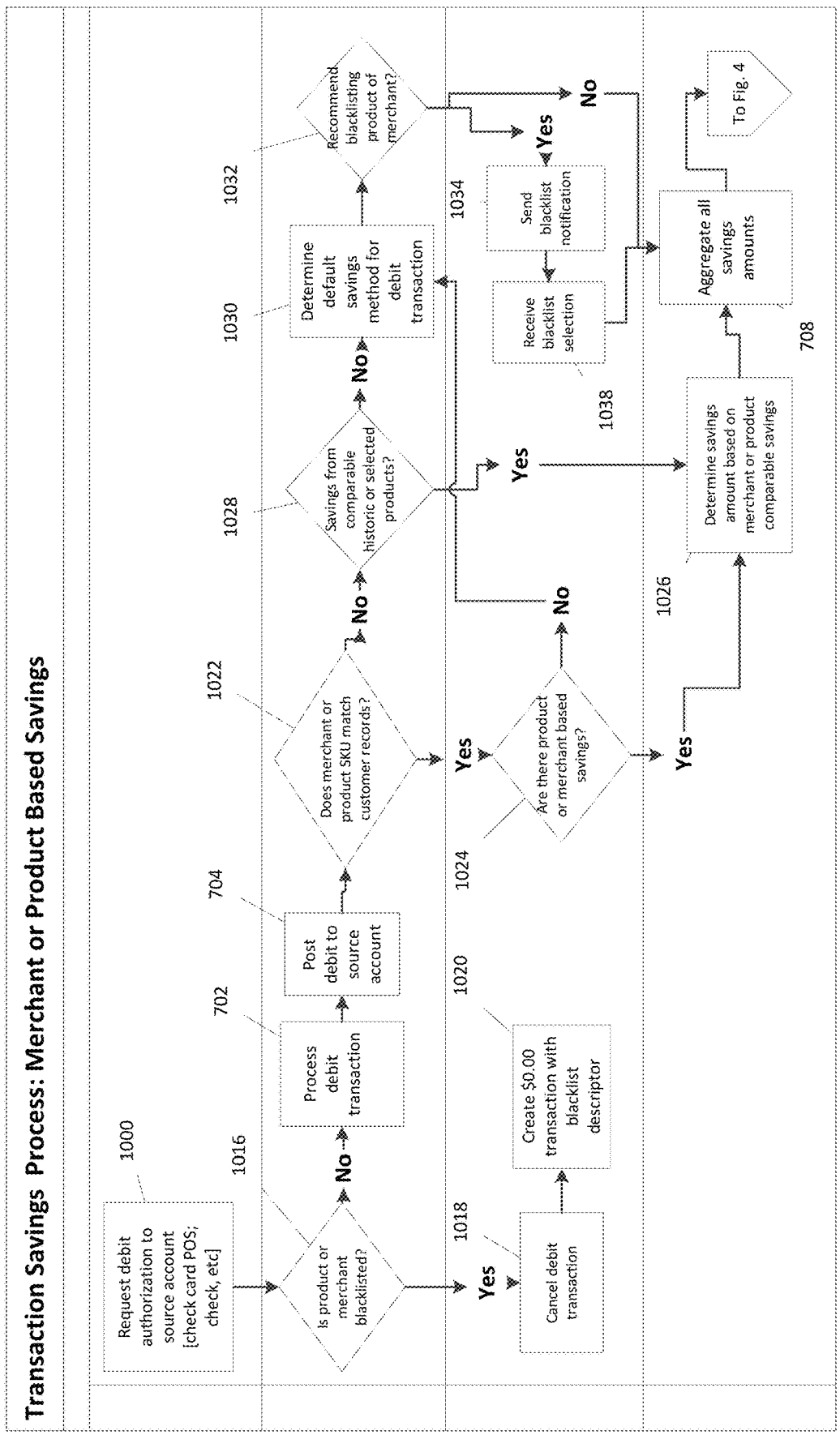
FIG. 10 illustrates a flowchart depicting a method of merchant or product based savings in accordance with aspects of the disclosure.

FIG. 10 provides one embodiment of the merchant or product based savings method. In step 1000, the debit to the source account (e.g., check card POS, check, and the like) is requested for authorization.

In step 1016 and with reference to elements depicted in FIG. 5, merchant product module 1045A may determine if the product or merchant is blacklisted by the user. If the product of merchant is blacklisted, merchant product module 1045A may proceed to cancel the debit transaction (step 1018) and a $0.00 transaction is created with a blacklist descriptor (step 1020).

In step 702, the debit transaction, may be processed.

In step 704, the debit transaction may be posted to the source account.

In step 1022 and with reference to elements depicted in FIG. 5, merchant product module 1045A may determine if the merchant or product SKU matches user records. Merchant product module 1045A (via processor 103A) may search memory 115A of computer system 101 to attempt to match the SKU of the current purchase with the SKU of all previous debit transactions of the selected source account during enrollment in the merchant or product savings program. Additionally, merchant product module 1045A may also compare the current transaction with any selected products or merchants by the user at enrollment. If merchant product module 1045A finds a match between the current transaction SKU and a previously selected or historical product or merchant SKU, the merchant and product module 1045A then proceeds to step 1024. If the current purchase does not match user records, then merchant and product module 1045A proceeds to step 1028.

In step 1024 and with reference to elements depicted in FIG. 5, where merchant product module 1045A has found a SKU match between the current transaction and previous transactions or selections by the user, merchant product module 1045A may determine if there is a merchant or product based savings by comparing the transaction amounts from the current transaction to the previous matching SKU transactions. If merchant product module 1045A determines that a merchant or product savings does exist, merchant product module 1045A proceeds to step 1026 to calculate the savings. If merchant product module 1045A determines that there are no merchant or product based savings, then merchant product module 1045A proceeds to step 1030 to determine the savings method by another means.

In step 1026 and with reference to elements depicted in FIG. 5, merchant product module 1045A may determine the savings amount based on a merchant or product comparable savings amount.

In step 1028 and with reference to elements depicted in FIG. 5, merchant product module 1045A may determine if product or merchant based savings from comparable historic or selected products exist where no SKU match was found in the users records. Merchant product module 1045A may run a matching algorithm to determine if there is a comparable product or service in the user's transaction history stored in memory 115A from which product or merchant based savings methods may be determined based on identifying factors of the product or service that is the subject of the current transaction. If merchant product module 1045A does find a comparable product or service, merchant product module 1045A may determine there are product or merchant savings, and proceed to step 1026. If merchant product module 1045A determines there is no comparable product, or additionally no product or merchant savings, merchant product module 1045A proceeds to step 1030.

In step 1030, the method of calculating the savings amount may be determined for transactions where a product of merchant based method does not apply. In one embodiment, the savings amount may be determined by either a round up, a discount, a whole monetary amount, a percentage based, a "treat yourself" method, or other criterion.

In step 1032 and with reference to elements depicted in FIG. 5, merchant product module 1045A may determine if the product or service that is the subject of the transaction should be recommended to the user for blacklisting. Merchant product module 1045A may search memory 115A to compare the product or service of the current transaction to historical comparable transactions by the user to determine if the user may be able to save with comparable products or services. If merchant product module 1045A determines the user's savings would be enhanced by blacklisting product or service of the current transaction, the merchant product module 1045A may proceed to step 1034. If the merchant product module 1045A determines the product or service should not be recommended, merchant product module 1045A proceeds to step 708.

In step 1034 and with reference to elements depicted in FIG. 5, merchant product module 1045A may send a blacklist recommendation notification to the user. In one embodiment of the present disclosure, merchant product module 1045A may send an encrypted blacklist recommendation notification via a modem in communications module 109A through WAN 129 to the Internet (e.g., network 131), and finally to smartphone 171. Smartphone 171 receives the blacklist recommendation notification via Internet (e.g., network 131) through communications module 109B and stores the notification in memory 115B. Merchant product module 1045B in smartphone 171, using processor 103B then initiates presenting the blacklist recommendation notification via audio interface 222. Audio interface 222 of smartphone 171 receives the notification from merchant product module 1045B, and the audio interface may then converts the electrical notification into an audible signal to the user via speakers 224 of smartphone 171. After receiving the audible blacklist recommendation notification, merchant product module 1045B may then present selection input options for updating the user's product or merchant blacklist. Merchant product module 1045B may present the selection input options for updating the user's product or merchant blacklist via touchscreen GUI 172 of communications module 109B by processor 103B of smartphone 171 to provide a graphical interface for the user to make a selection.

In step 1038 and with reference to elements depicted in FIG. 5, the product or merchant blacklist selection may be received. In one embodiment of the disclosure, smartphone 171 receives the product or merchant blacklist selection from the user. Once the user selects the product or merchant blacklist selections by touching the corresponding product or merchant blacklist input options via touchscreen GUI 172, that selection may be transmitted through communications module 109B to merchant product module 1045B, where it is then transmitted through communications module 109B to merchant product module 1045A of computer server 101 via the Internet (e.g., network 131) and communications module 109. Upon receiving the product or merchant blacklist selection, merchant product module 1045A may then update the blacklist in database 121A in step 1016.

In step 708, all merchant and product based savings, other default savings, or other amounts may be aggregated. This may occur on a daily, weekly, or other time basis. By aggregating the round ups for one daily or other selected time period for posting, exceeding account limits of the source account can be avoided. In one embodiment, the daily posting may occur at the end of the day to further avoid exceeding account limits.

One of ordinary skill in the art after review of the present disclosure will appreciate that various features and aspects of the disclosure allow the user to receive blacklist recommendation notifications by other wireless devices besides smartphone 171. The user may also associate other devices with the source account to communicate with merchant product module 1045A in computer system 101 for receiving blacklist recommendation notification and for allowing the user to select blacklist updates, such as a user's personal computer 161, tablet 181, or smartwatch 191. Any personal wireless device capable of containing merchant product module 1045B or communicating with computer server 101 and merchant product module 1045A may be used.

Further, in another embodiment of the present disclosure and with reference to elements depicted in FIG. 5, smartphone 171 may perform all of the steps outlined in FIG. 10 in the proceeding example without communicating with a computer server 101 or merchant product module 1045A. In one example of such an embodiment, smartphone 171 may interact with a POS device 162 to try to purchase a cup of coffee at a retail location (such as a café) via a user's source account enrolled in the merchant or product based savings service. Upon attempting to purchase a cup of coffee, the POS 162 device at the café may communicate with merchant product module 1045B of smartphone 171 via NFC for attempting to authorize the purchase. Merchant product module 1045B may then identify the identity of the cup of coffee via a product SKU number stored in memory 115B. Merchant product module 1045B may then determine if the product SKU number is on a blacklist stored in memory 115B, and if the product SKU is on a blacklist, merchant product module 1045B may cancel the transaction and send a notification to the user alerting them to the cancelled transaction as being blacklisted. If the product SKU was determined to not be on a blacklist, merchant product module 1045B may process the debit transaction and post the debit to the source account in communication with a bank server 141 or 151. Then merchant product module 1045B may determine the savings amount by determining if the product SKU matches user records for previous product or merchant based savings transactions. If merchant product module 1045B finds a match of product SKU, it may determine a product based savings amount from previous savings amounts based on the monetary amount of a more expensive cup of coffee at another café. If there is no product based savings from the match of product SKUs, merchant product module 1045B may then determine a savings amount based on a default method, such as a round up method described in previous examples. If there was no match in the user records for product SKU, merchant product module 1045B may then search user records for other cups of coffee based on a matching algorithm to determine if any product savings method is available. If the merchant product module 1045B finds a similar cup of coffee in the user records, and a product based savings amount applies, merchant product module 1045B will apply that savings technique. If merchant product module 1045B does not find a similar cup of coffee to apply a product based savings method, merchant product module 1045B may proceed to apply the default savings method and determines a round up savings amount. Merchant product module 1045B may also determine that the user may wish to blacklist this particular product of merchant for the cup of coffee to increase savings, and therefore may send a graphical notification such as a text message to the user recommending that the user add this cup of coffee or café to the blacklist. Merchant product module 1045B may also present the user with a graphical input to determine whether to blacklist the product or merchant. The merchant product module 1045B may receive the user's input to blacklist the cup of coffee product, and may add that product SKU to a blacklist file in database 121. Merchant product module 1045B of smartphone 171 then proceeds to aggregate the savings amounts and to communicate with banking servers 141 or 151 for posting those savings.

From the previous example of an embodiment of the present disclosure, it is clear that any personal mobile device capable of containing merchant product module 1045B and communicating with a POS device such as POS 162, may be able to carry out an embodiment of the present disclosure without need to communicate with a computer server 101 containing merchant product module 1045A.

In a further embodiment of the present disclosure, merchant product module 1045A at computer server 101 or merchant product module 1045B at smartphone 171 may communicate with a server 141 that contains a matching algorithm for determining if similar product purchases by a user are similar to the current transaction for providing product or merchant based savings. In a further example, merchant product module 1045B of smartphone 171, after failing to find a product or merchant SKU match in the user's previous transactions, communicates the SKU with server 141 via communications module 109B through Internet (e.g., network 131). Server 141 may then run the matching algorithm described in the previous example, and determine if there is a similar product based on the user's purchase history to match to the current transaction for determining a product based savings amount. Server 141 may then communicate this information to smartphone 171 for determining the savings amount. In this way, the matching algorithm may be stored on a separate server 141, as opposed to smartphone 171 or other personal wireless device of the user.

In one embodiment of the present disclosure, merchant product module 1045A or 1045B may recommend products to create product based savings after a purchase has occurred as described in the proceeding example. Upon a purchase by a user, merchant product module 1045B may communicate with server 141 to run a matching algorithm to determine if there are matching products that merchant product module 1045B in smartphone 171 may recommend to the user to switch to as a way to increase savings. If the matching algorithm at server 141 determines that a savings match is available, it may communicate that match to smartphone 171 as in the proceeding example.

In a further embodiment of the present disclosure, a user may purchase a cup of coffee with smartphone 171, and merchant product module 1045B fails to find a product or merchant savings amount based on the user's purchase records in memory 115B (step 1022) and also fails to find a product or merchant savings amount based on a matching algorithm. Merchant product module 1045B may then communicate with server 141 to instruct server 141 to run a matching algorithm to provide matches of similar products of cups of coffee that would save the user money if alternatively purchased. Upon finding a match, server 141 would communicate that example with merchant product module 1045B of smartphone 171, which would provide a graphical notification to the user as to the recommendation of the alternative cup of coffee to purchase to increase future savings.

In one embodiment of the present disclosure, merchant product module 1045B in smartphone 171 may identify a merchant or product identity at step 1016 based on a location device 104 in smartphone 171. For example, upon entering a store, merchant product module 1045B via location device 104 may detect the location of the smartphone as within a store and determine that store's merchant identity. Merchant product module 1045B may then compare the location derived merchant identity to the blacklist (step 1016), and may determine that attempts to authorize financial transactions for those merchant products within that location are blacklisted.

In a further embodiment of the present disclosure, smartwatch 191 may receive blacklist recommendation notifications from merchant product module 1045A in computer server 101 via communications module 109B. Smartwatch 191 may not have merchant product module 1045B, but upon receiving the blacklist recommendation notifications in communications module 109B, directly present the notifications to the user via a graphical message on the smartwatch GUI in communications module 109B, or as an audio alert through a speaker in communications module 109B in smartwatch 191. The smartwatch 191 may present any combination of graphical, audio, vibrational, or other method of blacklist recommendation notifications alerts to a user.

Further, smartwatch 191 may allow for the user to make a blacklist recommendation selection at the smartwatch touchscreen GUI 172 and then communicate that selection to merchant product module 1045A via communications module 109B in smartwatch 191, or it may communicate with another wireless device for the user to make a product or merchant blacklist selection. For example, upon receiving a blacklist recommendation selection from merchant product module 1045A, smartwatch 191 may alert the user. Then, smartwatch 191 communicates the blacklist recommendation notification with another wireless device of the user, such as tablet 181, which then presents the product or merchant blacklist selection input to the user.

In accordance with various aspects of the disclosure, the blacklist recommendation notifications presented to the user may be communicated in various forms. For example, after the wireless device of the user receives the notification, it may present the notification via vibration of the wireless device. Merchant product module 1045B of the wireless device, upon receiving the blacklist recommendation notification, would send the notification signal to a motor within communications module 109B that activates the motor and causes vibration within the wireless device. In another example, the merchant product module 1045B upon receiving blacklist recommendation notification would transmit a text or image graphical alert through a GUI of the communications module 109B.

Further, merchant product module 1045B may receive the user input for selection of the savings goal update through additional means. For example, upon presenting the user with blacklist recommendation selections through a GUI in communications module 109B of the wireless device, the user may select the blacklist recommendation through voice activation. Merchant product module 1045B may transmit the blacklist recommendation information to the GUI via processor 103B with corresponding voice activation phrases allowing a user to select blacklist recommendations, such as "blacklist product A". If the user speaks one of the voice activation phrases for an account, a microphone within the communications module 109B may detect the phrase and then send that selection information to merchant product module 1045B.

In another example, the user may select a blacklist recommendation through a GUI in the wireless device via a keyboard or mouse in communications module 109B.

One of ordinary skill in the art after review of the present disclosure will appreciate that the user's mobile device may receive the blacklist recommendation through a number of means. For example, in one embodiment, merchant product module 1045B of the wireless device may have the blacklist recommendation information stored on the mobile device in memory 115B. In this embodiment, upon receiving the blacklist recommendation notification, merchant product module 1045B of the wireless device would then retrieve the blacklist recommendation information from memory 115B to present the blacklist recommendation selection input options to the user. In another embodiment, merchant product module 1045B receives the blacklist recommendation information from computer server 101 along with the blacklist recommendation notification. The merchant product module 1045A may encrypt the blacklist recommendation information and then transmit this information over the Internet (e.g., network 131) through communications module 109A to the wireless device. Once the wireless device has received the encrypted blacklist recommendation information, merchant product module 1045B then decrypts the information and sends this information to communication module 109B for presenting to the user for selection. In a still further embodiment, the wireless device may communicate directly with bank server 141 for receiving the blacklist recommendation information.

In accordance with various aspects of the disclosure, merchant product module 1045A as part of computer system 101 may exist within a bank server 141 or 151 of a financial institution, such that merchant product module 1045A exists within memory 115A of bank server 141 or 151. Blacklisting information may then be transmitted directly between bank server 141 or 151 to the user's wireless device. When merchant product module 1045A in bank server 141 or 151 receives the blacklist information from the user's wireless device, merchant product module 1045A through processor 103 then updates the blacklist information.

Alternatively, the user's wireless device may not contain merchant product module 1045B within memory 115B. Merchant product module 1045A may transmit and present blacklist recommendation notifications, as well as receive blacklist recommendation inputs from the user through the wireless device. Merchant product module 1045A may communicate wirelessly with communications module 109B in the wireless device to directly send blacklist recommendation notification signals to the user. Further, when the user makes a blacklist recommendation selection, that selection may be transmitted directly from communications module 109B to the computers server 101 for processing by merchant product module 1045A. In this sense, the user's wireless device is operating as a portal for presenting and receiving blacklist recommendation information from merchant product module 1045A without requiring merchant product module 1045B on the wireless device.

Figure 16:
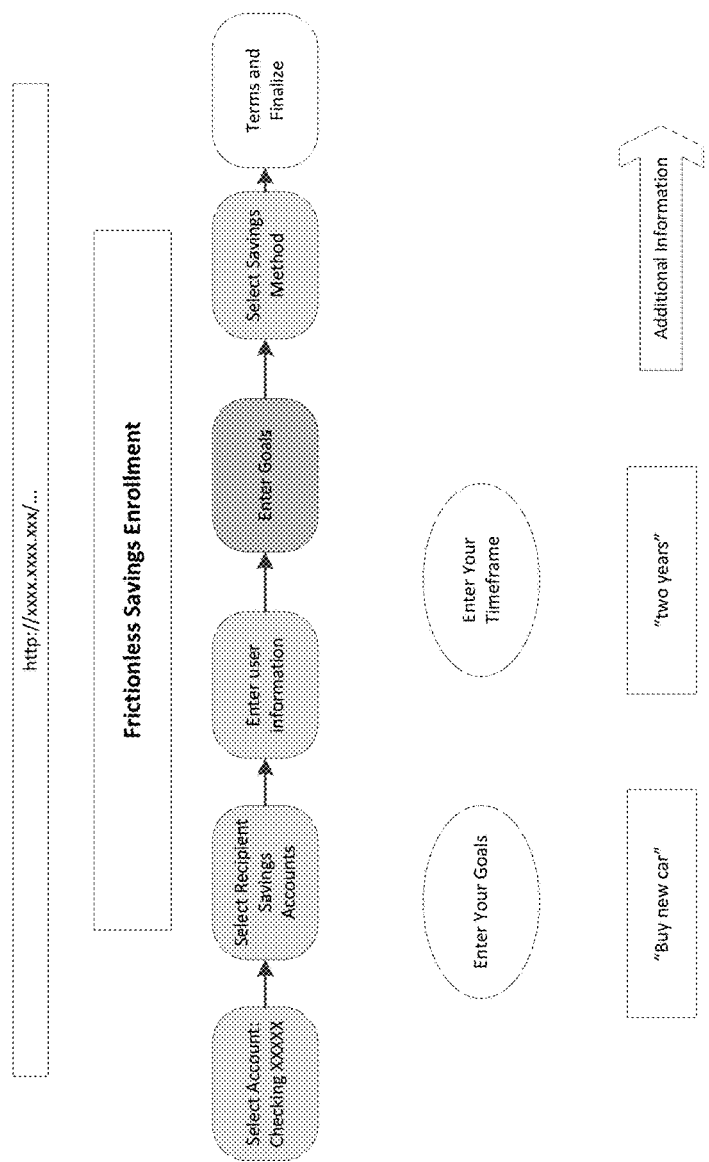
FIG. 16 depicts a graphic user interface depicting a further method of enrollment in accordance with aspects of the disclosure.

In reference to FIG. 16, in one embodiment of the present disclosure, the user is presented with an option to enroll in a frictionless savings service. If the user enrolls in the frictionless savings program, the user may select a source account (step 1600), as well as a recipient account (step 1602). In step 1604, the user may enter user information requested by computer server 101, which can include the user's income and expenditures, family information, and personal information of the user, such as age, health, and education, among any other relative criterion for helping to determine the most appropriate methods for savings. The user may then enter a savings goal for the recipient account (1612), and a time period for achieving the savings goal (step 1614). The user may then select a savings method (step 1608). Additionally, the frictionless savings module 1146A as disclosed in FIG. 5, may instead select appropriate savings methods for achieving the user's savings goal within the proposed time frame without the user selecting a savings method. The user is then presented with terms and conditions for the frictionless savings program and finalizes the enrollment (step 1610). The frictionless savings module 1146A may also track the spending and savings of the user over time, and automatically adjust or change the savings methods to keep the user's total savings on track to meet their selected goal. Frictionless savings module 1146A may also track the user's funds available in the source account, and automatically adjust the savings method to maintain a sufficient level of funds in the source account, or adjust the savings method to increase the savings rate based on the funds in the source account. The sufficient fund level may be determined automatically by the frictionless savings module 1146A based on the user's additional information and the server's records of historical expenditure levels and funds in the source account. Additionally, if the funds in the source account are above recorded fund levels, frictionless savings module 1146A can adjust the savings method to increase savings.

In another embodiment of the present disclosure, the frictionless savings module 1146A may further notify the user when the user's savings goal has been accomplished. Frictionless savings module 1146A may send a notification via Internet (e.g., network 131) to the users selected wireless device for receiving updates, such as personal computer 161, tablet 181, smartphone 171, and smartwatch 181, among any other wireless device able to associate with frictionless savings module 1146A.

Figure 11:
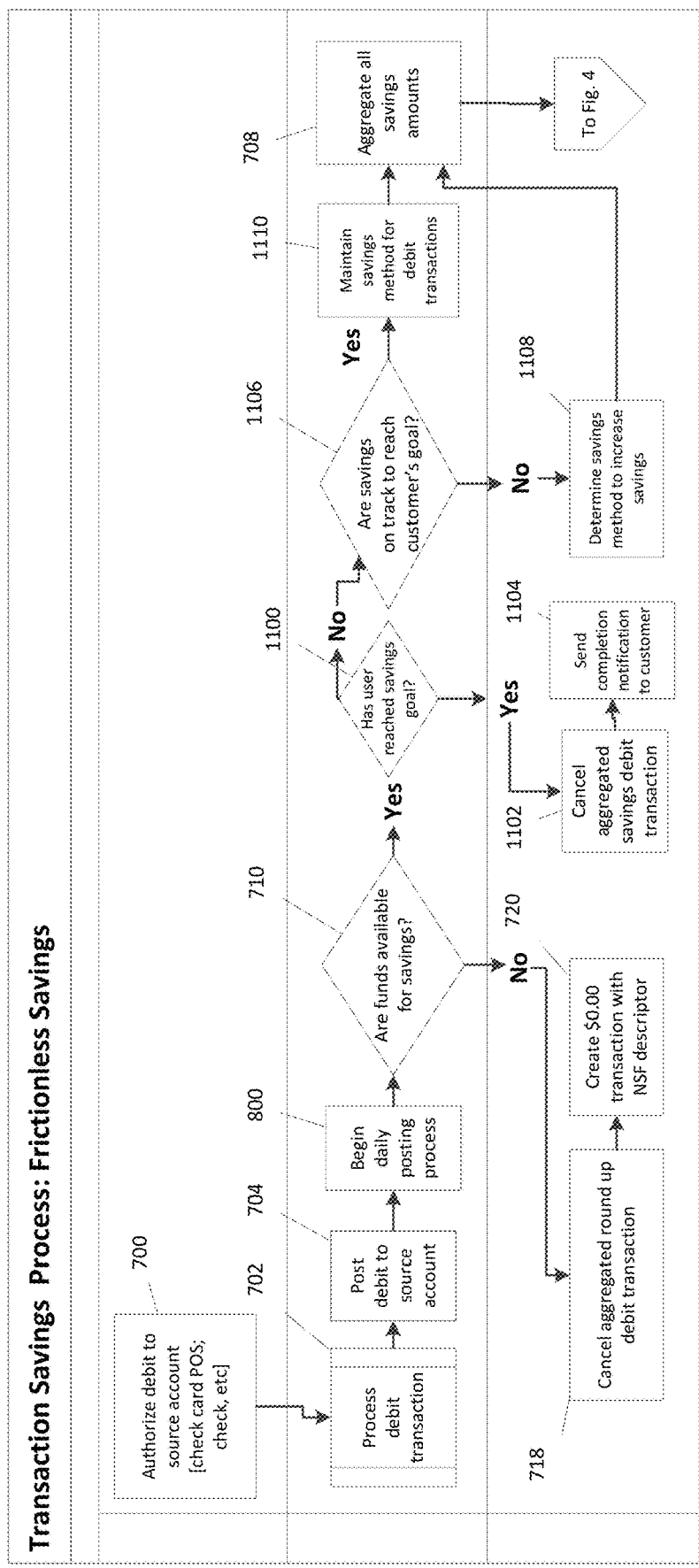
FIG. 11 illustrates a flowchart depicting a method of frictionless savings in accordance with aspects of the disclosure.

FIG. 11 shows an embodiment of the frictionless savings method of the present disclosure. In step 700, a debit to a source account (e.g., check card POS, check, and the like) is authorized.

In step 702, the debit transaction, such as a purchase at POS 162 using a debit card, may be processed.

In step 704, the debit transaction may be posted to the source account.

In step 800, the daily posting transaction begins.

In step 710, a determination may be made if funds are available in the source account. If not, the aggregated round up debit transaction may be cancelled (step 718) and a $0.00 transaction is created with a no funds in source account descriptor (step 720).

In step 1100, a determination may be made if the user has reached their savings goal. The frictionless savings module 1146A determines the total savings of the user and compares this to the savings goal of the user. If the savings have reached the user's savings goal, frictionless savings module 1146A cancels the aggregated savings transaction (step 1102) and sends a completion notification to the user (step 1104).

In step 1104, frictionless savings module 1146A may send a completion notification to the user. In one embodiment of the present disclosure, frictionless savings module 1146A may send a completion notification via a modem in communications module 109A through WAN 129 to the Internet (e.g., network 131), and finally to smartphone 171. Smartphone 171 receives the completion notification via Internet (e.g., network 131) through communications module 109B. Frictionless savings module 1146B in smartphone 171, using processor 103B then initiates presenting the completion notification via audio interface 222. Audio interface 222 of smartphone 171 receives the notification from frictionless savings module 1146B, and the audio interface may then convert the electrical notification into an audible signal to the user via speakers 224 of smartphone 171.

In step 1106, frictionless savings module 1146A may determine if the user's savings amounts are on track to meet the user's savings goal. If frictionless savings module 1146A determines that the user's savings are on track, frictionless savings module 1146A proceeds to step 1110. If the user's savings are determined to not be on track, then frictionless savings module 1146A proceeds to step 1108.

In step 1108, frictionless savings module 1146A determines an alternative savings method to use as the default savings method for transactions to meet the user defined goal.

In step 1110, frictionless savings module 1146A maintains the default savings method.

In step 708, all round up or other amounts may be aggregated. This may occur on a daily, weekly, or other time basis. By aggregating the round ups for one daily or other selected time period for posting, exceeding account limits of the source account can be avoided. In one embodiment, the daily posting may occur at the end of the day to further avoid exceeding account limits Additionally, alterative embodiments of the present disclosure may determine that the user's savings as of the determination in step 1106 are on track by a number of methods. In one embodiment, frictionless savings module 1146A may calculate the aggregate savings over a set time period, such as a week, month, or other time period, and determine if the savings during that time period meet a certain percentage of the savings goal correlating to the percentage of time to the savings goal. In another embodiment, frictionless savings module 1146A may determine if the user's savings are on track based on the percentage of savings relative to available funds.

In accordance with various aspects of the disclosure and with reference to elements depicted in FIG. 5, the frictionless savings module 1146A may determine alternative savings methods to increase savings at step 1108 in a number of ways. In one embodiment, frictionless savings module 1146A determines the alternative savings method based on the average available funds in the source account during the tracked goal period as determined in step 1106. In another embodiment, frictionless savings module 1146A may determine the savings method based on the savings method that will complete the savings goal closest to a given time period selected by the user.

Additionally, frictionless savings module 1146A may determine an alternative savings method at step 1108 from a number of methods. Frictionless savings module 1146A may adopt a round up, whole monetary, percentage based, product or merchant based, discount based, or other alternative savings methods to reach the desired goal.

One of ordinary skill in the art after review of the present disclosure will appreciate that various features and aspects of the disclosure allow the user to receive completion notifications by other wireless devices besides smartphone 171. The user may also associate other devices with the source account to communicate with frictionless savings module 1146A in computer system 101 for receiving completion notifications and for allowing the user to select blacklist updates, such as a user's personal computer 161, tablet 181, or smartwatch 191. Any personal wireless device capable of communicating with computer server 101 and frictionless savings module 1146A may be used.

In a further embodiment of the present disclosure, smartwatch 191 may receive completion notifications from frictionless savings module 1146A in computer server 101 via communications module 109B. Smartwatch 191 may not have frictionless savings module 1146A, but upon receiving the completion notifications in communications module 109B, directly present the notifications to the user via a graphical message on the smartwatch GUI in communications module 109B, or as an audio alert through a speaker in communications module 109B in smartwatch 191. The smartwatch 191 may present any combination of graphical, audio, vibrational, or other method of completion notifications alerts to a user.

In accordance with various aspects of the disclosure, the completion notifications presented to the user may be communicated in various forms. For example, after the wireless device of the user receives the notification, it may present the notification via vibration of the wireless device. Frictionless savings module 1146B of the wireless device, upon receiving the completion notifications, would send the notification signal to a motor within communications module 109B that activates the motor and causes vibration within the wireless device. In another example, the frictionless savings module 1146B upon receiving completion notifications would transmit a text or image graphical alert through a GUI of the communications module 109B.

One of ordinary skill in the art after review of the present disclosure will appreciate that the user's mobile device may receive the completion notifications through a number of means. For example, in one embodiment, frictionless savings module 1146B of the wireless device may have the completion notification information stored on the mobile device in memory 115B. In this embodiment, upon receiving the completion notification, frictionless savings module 1146B of the wireless device would then retrieve the completion notification information from memory 115B to present the completion notification to the user. In another embodiment, frictionless savings module 1146B receives the completion notifications from computer server 101. The frictionless savings module 1146A may transmit the completion notifications information over Internet (e.g., network 131) through communications module 109A to the wireless device. Once the wireless device has received the completion notifications, frictionless savings module 1146B then sends this information to communication module 109B for presenting to the user for selection. In a still further embodiment, the wireless device may communicate directly with bank server 141 for receiving the blacklist recommendation information.

In accordance with various aspects of the disclosure, frictionless savings module 1146A as part of computer system 101 may exist within a bank server 141 or 151 of a financial institution, such that frictionless savings module 1146A exists within memory 115A of bank server 141 or 151. Blacklisting information may then be transmitted directly between bank server 141 or 151 to the user's wireless device. When frictionless savings module 1146A in bank server 141 or 151 receives the completion notification from the user's wireless device, frictionless savings module 1146A through processor 103 then updates the blacklist information.

Alternatively, the user's wireless device may not contain frictionless savings module 1146B within memory 115B. Frictionless savings module 1146A may transmit and present blacklist recommendation notifications, as well as receive blacklist recommendation inputs from the user through the wireless device. Frictionless savings module 1146A may communicate wirelessly with communications module 109B in the wireless device to directly send blacklist recommendation notification signals to the user. Further, when the user makes a blacklist recommendation selection, that selection may be transmitted directly from communications module 109B to the computers server 101 for processing by frictionless savings module 1146A. In this sense, the user's wireless device is operating as a portal for presenting and receiving blacklist recommendation information from frictionless savings module 1146A without requiring frictionless savings module 1146B on the wireless device.

In an additional embodiment of the present disclosure, frictionless savings module 1146A may determine a savings method using comparisons to savings rates for demographically similar users. For example, frictionless savings module 1146A in computer server 101 may communicate with frictionless savings module 1146B of bank servers 151 via communications modules 109A and 109B through Internet (e.g., network 131) to compare the user's saving rate to demographically similar user based on their information saved in memory 115B of computer servers 151. Bank servers 151 may determine demographically similar user based on the goals and information entered when the users enrolled in the frictionless savings program. Upon determining demographically similar users, bank servers 151 may send the demographically similar user savings rate information to frictionless savings module 1146A of computer server 101, which will then incorporate the demographically similar savings rate into calculating a frictionless savings amount.

Further, frictionless savings module 1146A may communicate with servers 141 representing social media servers, to determine a savings method using comparisons to savings rates for demographically similar users. For example, a user may be enrolled in social media applications and link his frictionless savings account to his social media applications. Frictionless savings module 1146A in computer server 101 may communicate with those social media application servers 141 to determine demographically similar users according to the proceeding example. Frictionless savings module 1146A may then incorporate those demographically similar user's savings rates in calculating a frictionless savings amount.

Further, in another embodiment of the present disclosure, the user may enroll in the frictionless savings program and connect the frictionless savings program to a social media application for the purpose of comparing savings rates with those of friends who are also enrolled in the frictionless savings program and the social media application.

In one embodiment of the present disclosure, the user may enroll in a savings and investment program. A user may select recipient investment account for their savings, and select an associated investment portfolio with the investment account from which the savings will be invested into.

Figure 6B:
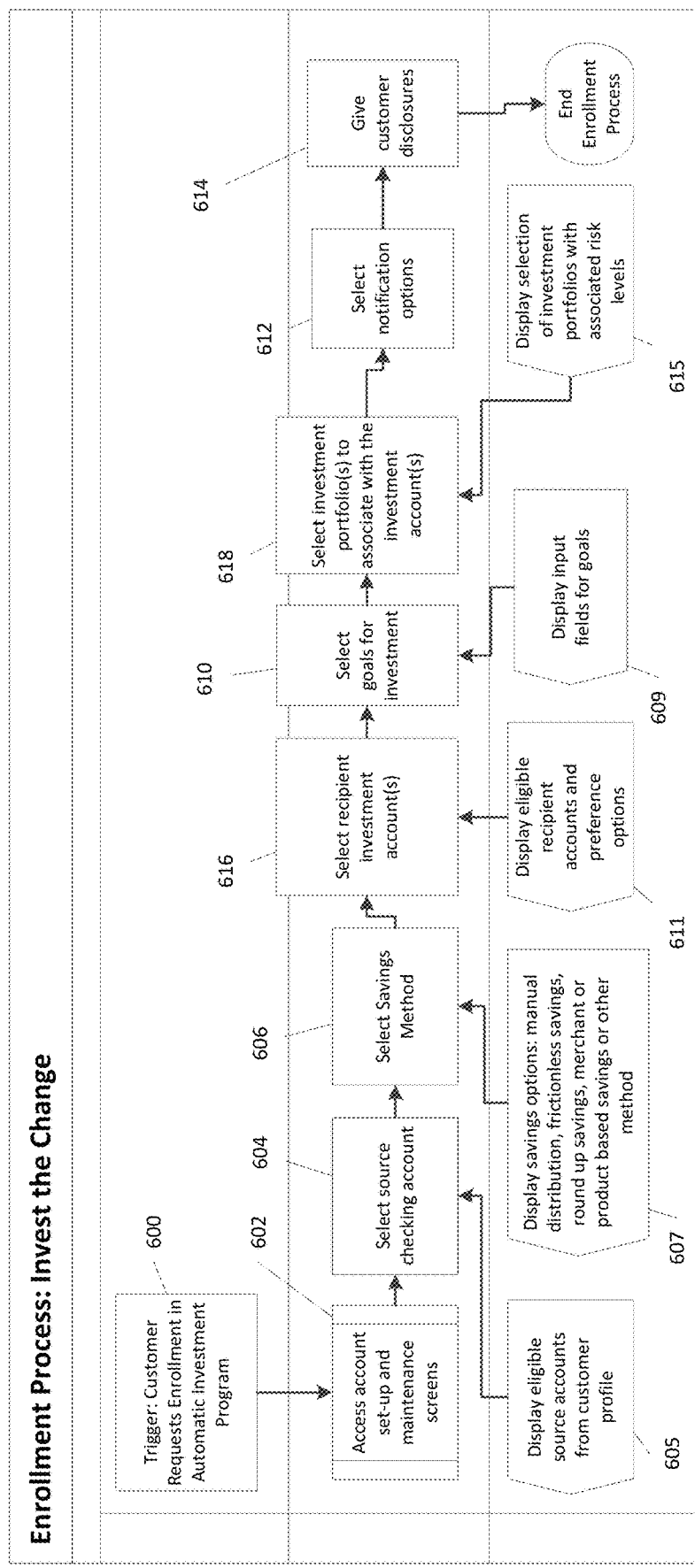
FIG. 6B illustrates a flowchart depicting an additional enrollment method in accordance with aspects of the disclosure.

FIG. 6B is a flow diagram of the functionality performed by computer system 101 in accordance with one embodiment of the present disclosure in order to enroll a user in the savings and investment program.

In step 602, account set-up and maintenance screens/interfaces are accessed in response to a user request to enroll in the automatic savings program. In one embodiment, the screens/interfaces are accessed by bank personnel at a terminal locally or remotely connected to computer system 101. In another embodiment, a user may access the screens/interfaces at a terminal remotely connected to computer system 101 through Internet (e.g., network 131). In another embodiment, the user may access the screens/interfaces with any wireless device capable of connecting to the computer system 101 through Internet (e.g., network 131), such as ATM 163, personal computer 161, tablet 181, smartphone 171, or smartwatch 191.

In step 604, the checking account that is the source of the automatic savings amount is selected. The eligible source accounts are displayed from the user's profile. In other embodiments, another type of account instead of a checking account can be used, as long as the selected account is a source of funds.

In step 606, the savings method is selected. One method may be a "round up," which refers to one method used to calculate a savings amount from a transaction. In one embodiment, the round up amount is an amount of excess funds produced by applying a rounder transaction to the amount of a transaction such as a credit/debit card charge at POS 162. If the rounder transaction rounds up to the nearest dollar, for example, a purchase made for $54.08 would generate a rounded amount of $0.92. Other embodiments of the present disclosure may round up to a predetermined amount besides the nearest dollar. Still further, other embodiments of the present disclosure may calculate the savings amount using a method other than round up. For example, a fixed percentage can be applied to each transaction to calculate a savings amount, or a fixed amount of money (e.g., $1.20) can be considered the savings amount. The available debits/transaction types to be round up are displayed (step 607) and can include check card/debit card POS transactions, or any other types of debits. Examples of other debits that can be the subject of round up or other calculation of a savings amount include paper checks, electronic bill pay, electronic checks, automatic payments and Automated Clearing House ("ACH") transfers.

In step 616, the recipient investment account or accounts for the savings amount may be selected based on the displayed eligible recipient accounts and preference option fields for the accounts can be inputted. In one embodiment, possible recipient accounts include the user's own recipient investment account, person-to-person transfer (e.g., a grandparent's round ups being credited to a grandchild's recipient investment account), and the like. In general, any recipient investment account that can accept transfers can be eligible for selection. If multiple recipient investment accounts are selected, the user can choose a percentage distribution for each of the recipient accounts, or another mechanism that can be used to divide the savings amount between the multiple investment accounts or create a preference for savings between the accounts.

In step 610, goals may be selected for the recipient investment account or accounts. In one embodiment, the server may present the user with an option to input the user's desired financial goals. To determine the user's desired financial goals, the server may request information from the user regarding the user's qualitative or quantitative goals, such as "buy a car," "pay for child's college education" or "save $2,000." The server can additionally request a time frame to achieve this goal, and may also request the user's income and expenditures, and any additional information that may be relevant to ascertaining the appropriate savings method for the user. A separate goal can be selected for each recipient investment account if multiple recipient investment accounts are selected for the program. The user may also select intermediate goals for a recipient investment account to help the user stay on track for reaching their goal for the recipient investment account.

In step 618, the user may select an investment portfolio to associate with the recipient investment account for the savings to be applied to. The savings amounts that are directed into the investment account may then be invested into the selected investment portfolio. The user may select multiple investment accounts, and split up the round up amounts between the multiple selected investment accounts. Each individual investment account may be associated with a separate investment portfolio. In another embodiment of the disclosure, the investment portfolio may be pre-defined, in which the investments of the portfolio have been pre-selected by another individual. For example, the investment portfolio may be designed by an investment manager at the bank of the investment account, or another third party that provides the portfolio to the bank.

In step 612, notification services may be selected for the savings accounts.

In step 614, user disclosures may be presented to the user to agree to before enrollment.

Figure 18:
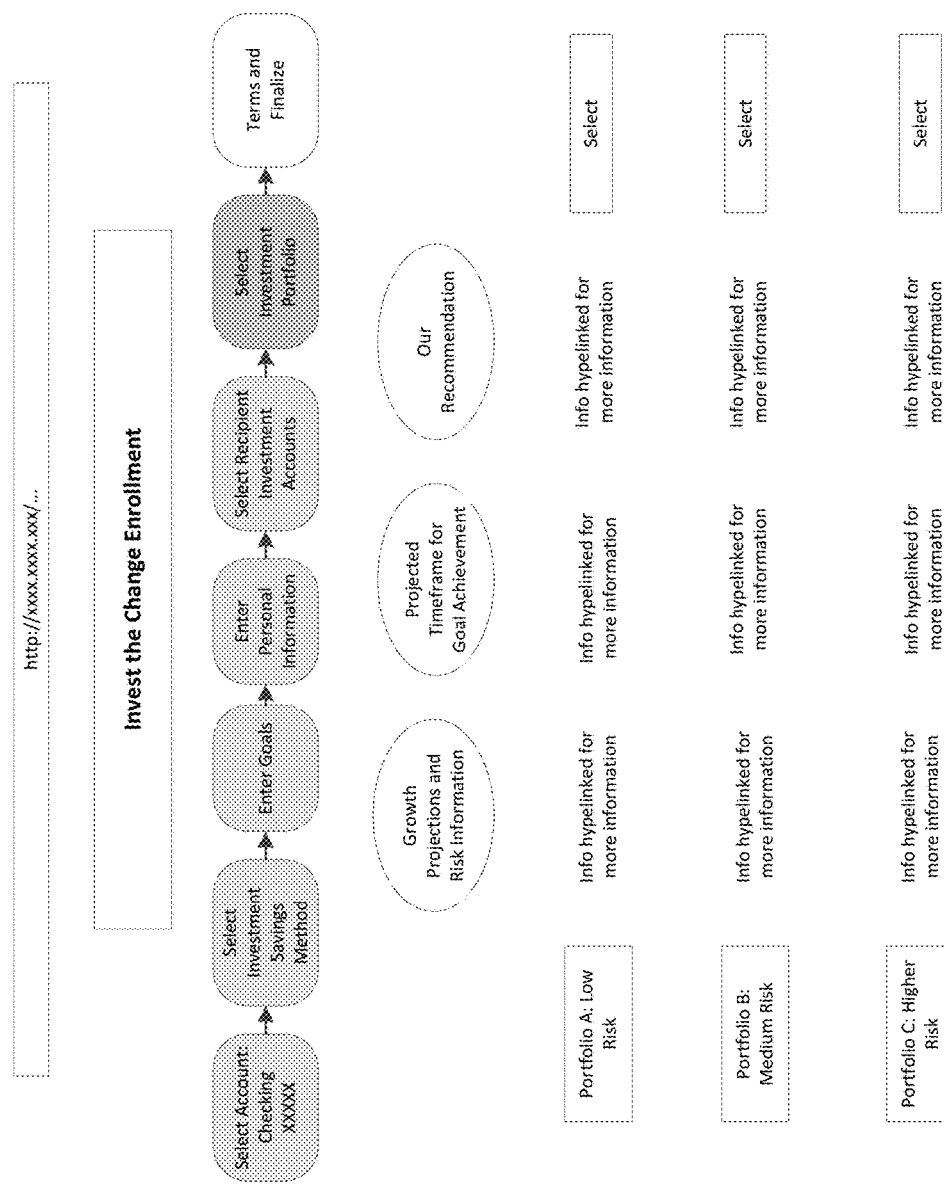
FIG. 18 depicts a graphic user interface depicting a further method of enrollment in an investment savings program in accordance with aspects of the disclosure.

Referring to FIG. 18, enrolling a user in a savings and investment program through a GUI is shown. GUI 1800 shows an interface presented to a user with selectable inputs 1822 for selecting a portfolio. Element 1816 shows display elements for the portfolio risk levels and the performance levels of each portfolio. The user may select element 1804 for entering in financial goals for the recipient account. Element 1818 of the GUI 1800 shows a display element for the growth projection of each portfolio.

In a further embodiment of the present disclosure, once a user has identified the investment account where the round up investments will go, the user may select a pre-defined investment portfolio from a number of portfolio options presented to the user, and the user chooses a preferred investment portfolio based on the risk levels respectively indicated for the portfolio options. A pre-defined portfolio may be designed based on an overall risk level for the portfolio, e.g., as determined by an investment manager. In one embodiment, an investment portfolio may be defined as "low risk," "medium risk," or "high risk." A "low risk" portfolio may be characterized by having a relatively low rate of return but also a relatively low risk of loss as compared to "medium risk" or "high risk" portfolios. A "medium risk" portfolio may be characterized by having a relatively higher rate of return and a relatively higher risk of loss as compared to a "low risk" portfolio, but also by having a relatively lower rate of return and a relatively lower risk of loss as compared to a "high risk" portfolio. A "high risk" portfolio may be characterized by having a relatively higher rate of return and a relatively higher risk of loss as compared to both a "low risk" portfolio and a "medium risk" portfolio. As an example, a pre-defined investment portfolio may be designated as "low risk" by having an estimated rate of return of 3% and a relatively low corresponding risk of loss, while a "medium risk" portfolio may have estimated rate of return of 6%, and a relatively medium corresponding risk of loss, and a "high risk" portfolio may have estimated rate of return of 10% with a relatively high corresponding risk of loss. Still further, other embodiments of the present application may include rates of return and risks of loss that vary over time with risk designations, for example, in response to changes in inflation rates. Additionally, there may be more varied levels of risk of portfolios to accommodate a greater variety of user preferences.

Additionally, after obtaining the information requested from the user regarding their goals for the investment account, computer server 101 may recommend a pre-defined investment portfolio based on the user's information. Computer server 101 may additionally recommend multiple pre-defined portfolios based on the selection of investment savings methods, which may adjust the time to reach the user's savings goal. Also, computer server 101 may present an estimate as to when any of the recommended pre-defined investment portfolios would meet the user's savings goal, and also present the growth projection based on the performance of the pre-defined investment portfolio. In another embodiment, the server may allow the user to configure the investment portfolios to meet their specific needs, by allowing the user to combine or edit investment portfolios. For example, a user may wish to combine two investment portfolios into one to create a custom risk and reward expectation. Still further, in another embodiment a user may wish to edit a single portfolio to create a safer or riskier portfolio than is available. Once a user has configured the pre-defined investment portfolios to meet the users customized needs, the server may analyzed this new customized portfolio and provide the user with information regarding the estimated rate of return and risk of losses, growth projections, and time estimates to meet the user's goals.

In another embodiment, the savings amount may be determined by a discount method. Many retailers and companies provide discounts on goods or services based on user membership or in coordination with the user's financial institution. When a user makes a purchase from their source account, and is provided a discount by the provider of goods or services in affiliation with the bank of the source account, the computer system 101, in communication with the retailer/provider, determines the difference between the discounted amount and the full price. This is the discount amount. The user is then charged the full price, with the discount amount then being applied to the recipient account from the source account as a savings amount. An example of this embodiment is a purchase made by a user at a grocery store. In affiliation with a bank, a grocery store chain may provide discounts for members of the bank who make purchases at the grocery store with their bank cards. A user who is enrolled in the program may pay the "full price," but the discount amount is actually being saved into the recipient investment account from the user's source account.

Figure 12:
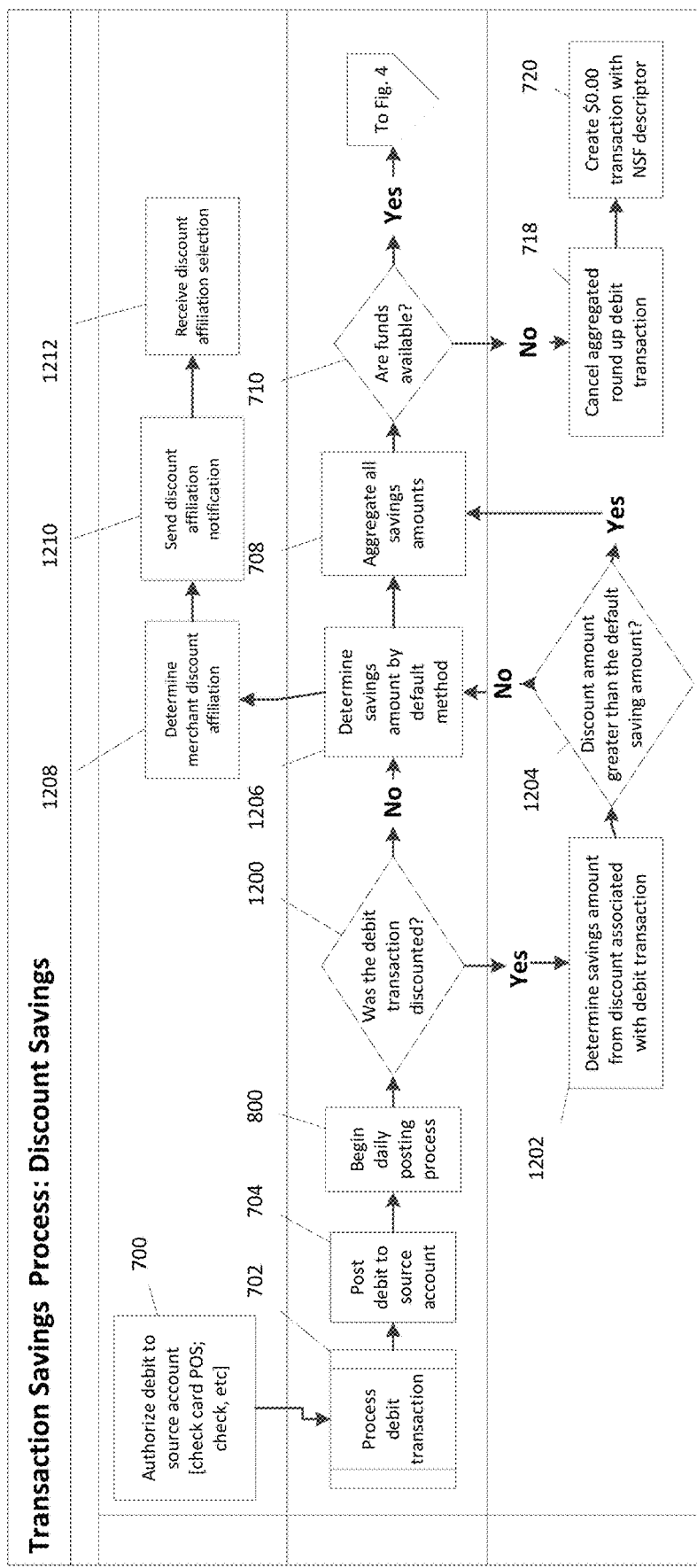
FIG. 12 illustrates a flowchart depicting a method of discount savings in accordance with aspects of the disclosure.

FIG. 12 displays one embodiment of the discount savings method. In step 700, a debit to a source account (e.g., check card POS, check, and the like) is authorized.

In step 702, the debit transaction is processed.

In step 704, the debit transaction may be posted to the source account.

In step 800, the daily posting transaction begins.

In step 1200, and with reference to elements depicted in FIG. 5, discount savings module 1238A in computer system 101 may determine if the debit transaction was a discounted transaction. Discount savings module 1238A may communicate with POS device 162 via communication module 109A through Internet (e.g., network 131) to determine if a savings discount was applied to the transaction.

In step 1202, and with reference to elements depicted in FIG. 5, discount savings module 1238A may determine the discount amount associated with the transaction. Discount savings module 1238A may communicate with POS device 162 via communication module 109A through Internet (e.g., network 131) to determine the savings discount amount. Discount savings module 1238A then stores that discount amount in memory 115A.

In step 1204, discount savings module 1238A compares whether the discount savings amount is greater than the default savings method.

In step 1206, and with reference to elements depicted in FIG. 5, the savings amount may be determined by the default savings method. In one embodiment, this method may be a non-discount savings method that discount savings module 1238A applies where there were no discounts in the transaction, or where a discount savings method may provide fewer saving than the default method. Further, the default savings amount may be determined by either a round up, a discount, a merchant or product based savings, a whole monetary amount, a percentage based, a "treat yourself" method, or other criterion. The default method may be selected by the user during enrollment in the discount savings method.

In step 708, all discount or default savings amounts, or other amounts, may be aggregated. This may occur on a daily basis. By aggregating the round ups for one daily posting, exceeding account limits of the source account can be avoided. In one embodiment, the daily posting may occur at the end of the day to further avoid exceeding account limits.

In step 1208, and with reference to elements depicted in FIG. 5, discount savings module 1238A may determine if a merchant discount affiliation option is available to the user to increase future savings. In one embodiment of the present invention, discount savings module 1238A via communication module 109A through Internet (e.g., network 131) may communicate with a computer server 141 that is affiliated with the merchant associated with the transaction at step 700 of FIG. 12. Discount savings module 1238A may request information regarding any possible membership or affiliation discounts that the user may enroll in with the merchant or retailer associated with the transaction that may increase future savings.

In step 1210, and with reference to elements depicted in FIG. 5, discount savings module 1238A may send a discount affiliation notification to the user. In one embodiment of the present disclosure, discount savings module 1238A may send a discount affiliation notification via a modem in communications module 109A through WAN 129 to the Internet (e.g., network 131), and finally to smartphone 171. Smartphone 171 receives the discount affiliation notification via Internet (e.g., network 131) through communications module 109B and stores the notification in memory 115B. Discount savings module 1238B in smartphone 171, using processor 103B then initiates presenting the discount affiliation notification via audio interface 222. Audio interface 222 of smartphone 171 receives the notification from discount savings module 1238B, and the audio interface may then converts the electrical notification into an audible signal to the user via speakers 224 of smartphone 171. After receiving the audible discount affiliation notification, discount savings module 1238B may then present discount affiliation information and selection input options for creating the user's merchant affiliation or membership. Discount savings module 1238B may present the selection input options for creating the user's merchant affiliation or membership via touchscreen GUI 172 of communications module 109B by processor 103B of smartphone 171 to provide a graphical interface for the user to make a selection.

In step 1212, and with reference to elements depicted in FIG. 5, the discount affiliation selection may be received. In one embodiment of the disclosure, smartphone 171 receives the discount affiliation selection from the user. Once the user selects the discount affiliation selections by touching the corresponding discount affiliation input options via touchscreen GUI 172, that selection may be transmitted through communications module 109B to discount savings module 1238B, where it is then transmitted through communications module 109B to discount savings module 1238A of computer server 101 via the Internet (e.g., network 131) and communications module 109. Upon receiving the discount affiliation selection, discount savings module 1238A may then communicate with a computer server 141 that is affiliated with discount affiliation for creating the user's membership or affiliation.

In step 710, a determination may be made if funds are available in the source account. If not, the aggregated round up debit transaction may be cancelled (step 718) and a $0.00 transaction is created with a no funds in source account descriptor (step 720).

One of ordinary skill in the art after review of the present disclosure will appreciate that various features and aspects of the disclosure allow the user to receive discount affiliation notifications by other wireless devices besides smartphone 171. The user may also associate other devices with the source account to communicate with discount savings module 1238A in computer system 101 for receiving discount affiliation notifications and for allowing the user to select discount affiliations, such as a user's personal computer 161, tablet 181, or smartwatch 191. Any personal wireless device capable of containing discount savings module 1238B or communicating with computer server 101 and discount savings module 1238A may be used.

Further, in another embodiment of the present disclosure, smartphone 171 may perform all of the steps outlined in FIG. 12 in the proceeding example without communicating with a computer server 101 or discount savings module 1238A. In one example of such an embodiment, smartphone 171 may interact with a POS device 162 to try to purchase a cup of coffee at a café via a user's source account enrolled in the discount savings service. Upon attempting to purchase a cup of coffee, the POS 162 device at the café may communicate with discount savings module 1238B of smartphone 171 via NFC for authorizing the purchase. Discount savings module 1238B may then determine if a discount was applied to the cup of coffee via a membership affiliation between the user and the merchant. If a discount was not applied, discount savings module 1238B may then communicate with computer server 141 affiliated with the merchant to determine if a membership or affiliation discount exists, and if such a membership exists, discount savings module 1238B may send a notification to the user alerting them to a membership or affiliation savings. Discount savings module 1238B may send a graphical notification such as a text message to the user recommending that the user may enroll in a membership of affiliation with the merchant. Discount savings module 1238B may also present the user with a graphical input to determine whether to enroll in a membership with the merchant. The discount savings module 1238B may receive the user's input to enroll in the membership. Discount savings module 1238B then communicates with computer server 141 affiliated with the merchant to update the user's enrollment. If there is no discount based savings from a membership of affiliation, discount savings module 1238B may then determine a savings amount based on a default method, such as a round up method described in previous examples. Discount savings module 1238B of smartphone 171 then proceeds to aggregate the savings amounts and to communicate with banking servers 141 or 151 for posting those savings to the recipient investment account.

From the previous example of an embodiment of the present disclosure, it is clear that any personal mobile device capable of containing discount savings module 1238B and communicating with a POS 162 or computer system 141 may be able to carry out an embodiment of the present disclosure without need to communicate with a computer server 101 containing discount savings module 1238A.

In one embodiment of the present disclosure and with reference to elements depicted in FIG. 5, discount savings module 1238B in smartphone 171 may identify a merchant identity to enroll in a membership or affiliation at step 1208 based on a location device 104 in smartphone 171. For example, upon entering a store, discount savings module 1238B via location device 104 may detect the location of the smartphone as within a store and determine that store's merchant identity. Discount savings module 1238B may determine if there is a membership or affiliation available for the user to enroll in to increase savings (step 1208), and may send a discount affiliation notification to the user.

In a further embodiment of the present disclosure, smartwatch 191 may receive discount affiliation notification from discount savings module 1238A in computer server 101 via communications module 109B. Smartwatch 191 may not have discount savings module 1238B, but upon receiving the discount affiliation notification in communications module 109B, directly present the notifications to the user via a graphical message on the smartwatch GUI in communications module 109B, or as an audio alert through a speaker in communications module 109B in smartwatch 191. The smartwatch 191 may present any combination of graphical, audio, vibrational, or other method of discount affiliation notification alerts to a user.

Further, smartwatch 191 may allow for the user to make a discount affiliation selection at the smartwatch touchscreen GUI 172 and then communicate that selection to discount savings module 1238A via communications module 109B in smartwatch 191, or it may communicate with another wireless device for the user to make a discount affiliation selection. For example, upon receiving a discount affiliation selection from discount savings module 1238B, smartwatch 191 may alert the user. Then, smartwatch 191 communicates the discount affiliation notification with another wireless device of the user, such as tablet 181, which then presents the product or merchant discount affiliation selection input to the user.

In accordance with various aspects of the disclosure, the discount affiliation notifications presented to the user may be communicated in various forms. For example, after the wireless device of the user receives the notification, it may present the notification via vibration of the wireless device. Discount savings module 1238B of the wireless device, upon receiving the discount affiliation notification, would send the notification signal to a motor within communications module 109B that activates the motor and causes vibration within the wireless device. In another example, the discount savings module 1238B upon receiving discount affiliation notification would transmit a text or image graphical alert through a GUI of the communications module 109B.

Further, discount savings module 1238B may receive the user input for selection of the discount affiliation enrollment through additional means. For example, upon presenting the user with discount affiliation selections through a GUI in communications module 109B of the wireless device, the user may select the discount affiliation through voice activation. Discount savings module 1238B may transmit the discount affiliation information to the GUI via processor 103B with corresponding voice activation phrases allowing a user to select discount affiliations, such as "enroll in membership A". If the user speaks one of the voice activation phrases for an account, a microphone within the communications module 109B may detect the phrase and then send that selection information to discount savings module 1238B.

In another example, the user may select a discount affiliation notification through a GUI in the wireless device via a keyboard or mouse in communications module 109B.

One of ordinary skill in the art after review of the entirety disclosed herein will appreciate that the user's mobile device may receive the discount affiliation notification through a number of means. In one embodiment, discount savings module 1238B of the mobile device receives the discount affiliation notification information from computer server 101 along with the discount affiliation notification. The discount savings module 1238B may transmit this information over the Internet (e.g., network 131) through communications module 109A to the wireless device. Once the wireless device has received the discount affiliation notification, discount savings module 1238B then sends this information to communication module 109B for presenting to the user for selection. In a still further embodiment, discount savings module 1238B of the mobile device may communicate directly with merchant server 141 for receiving the discount affiliation notification without communicating with computer server 101.

Alternatively, the user's wireless device may not contain discount savings module 1238B within memory 115B. Discount savings module 1238A may transmit and present discount affiliation notifications, as well as receive discount affiliation inputs from the user through the wireless device. Discount savings module 1238A may communicate wirelessly with communications module 109B in the wireless device to directly send discount affiliation notification signals to the user. Further, when the user makes discount affiliation selection, that selection may be transmitted directly from communications module 109B to the computers server 101 for processing by discount savings module 1238A. In this sense, the user's wireless device is operating as a portal for presenting and receiving discount affiliation information from discount savings module 1238A without requiring discount savings module 1238B on the wireless device.

Another embodiment of the disclosure includes forms of computer-readable media. Computer-readable media include any available media that can be accessed by a computing device 101. Computer-readable media may comprise non-transitory storage media and communication media. Non-transitory storage media include volatile and nonvolatile, removable and non-removable media implemented in any method or technology for storage of information such as computer-readable instructions, object code, data structures, program modules, or other data.

Although not required, one of ordinary skill in the art after review of the present disclosure will appreciate that various aspects described herein may be embodied as a method, a data processing system, or as a computer-readable medium storing computer-executable instructions. For example, a computer-readable medium storing instructions to cause a processor to perform steps of a method in accordance with aspects of the disclosure is contemplated. For example, aspects of the method steps disclosed herein may be executed on a processor on a computing device 101. Such a processor may execute computer-executable instructions stored on a computer-readable medium.

Aspects of the disclosure have been described in terms of illustrative embodiments thereof. Numerous other embodiments, modifications and variations within the scope and spirit of the appended claims will occur to persons of ordinary skill in the art from a review of this disclosure. For example, one of ordinary skill in the art after review of the entirety disclosed herein will appreciate that the steps illustrated in the illustrative figures may be performed in other than the recited order, and that one or more steps illustrated may be optional in accordance with aspects of the disclosure. Also, one of ordinary skill in the art after review of the entirety disclosed herein will appreciate that various features and aspects of the disclosure may be combined with other features and aspects disclosed herein.

For example, one of ordinary skill in the art after review of the present disclosure will appreciate that a user may select to enroll in multiple savings methods. For example, a user may decide to enroll in both the product/merchant based savings method and also the discount method. In this embodiment, during a financial transaction at a retail location, computer sever 101 may communicate with a POS device 162 at the retail location to determine if product or merchant based savings exist, and additionally if a discount savings exist. Merchant product module 1045A may determine that a merchant or product based savings exists. Additionally, discount savings module 1238A may also determine that a discount savings exists. The merchant product module 1045A and discount savings module 1238A in computer server 101 may communicate to determine which of the savings methods provides greater savings for the user, and send a notification to user via the user's smartphone 171. In a further embodiment, merchant product module 1045A and discount savings module 1238A may communicate to determine if discount savings may apply in conjunction with product or merchant savings to create greater savings than only applying a product or merchant based savings method alone.

In another example that one of ordinary skill in the art after review of the present disclosure will appreciate, a user may select to enroll in multiple notifications as well as multiple savings methods. For example, a user may select to enroll in a selective distribution service as well as an additional savings service. In this example, selective distribution module 1242A in computer system 101 may determine that savings have met a threshold for sending a selective distribution notification to the user at smartphone 171. In addition, additional savings module 843A may also determine that the user is not on track for their savings goal, and may send an additional savings notification in conjunction with the selective distribution notification, prompting a user to add additional savings to the selective distribution amount. In a still further embodiment, the user may also be enrolled in the savings goal module, such that the user is also sent periodic savings goal notifications from savings goal module 944A, in addition to receiving selective distribution notifications and additional savings notifications from selective distribution module 1242A and additional savings module 843A, respectively.

In another example that one of ordinary skill in the art after review of the present disclosure will appreciate, particular embodiments and technology from a savings method described may be combined with particular embodiments and technology from a different savings method. For example, a user may be enrolled in a merchant and product savings service, and the savings goal service. The user's transactions from their enrolled source account would be monitored by merchant product module 1045A for any merchant or product based savings, and the user may also receive periodic savings goal notifications from savings goal module 944A. Still further, the user may also connect their source account with social media applications used by the user, such that savings goal module 944A may communicate with frictionless savings module 1146A of computer 101 and frictionless savings module 1146B of bank servers 151 via communications modules 109A and 109B through Internet (e.g., network 131) to compare the user's saving rate to demographically similar user based on their information saved in memory 115B of computer servers 151. In this way, when the user receives periodic savings goal notifications from savings goal module 944A, the notifications may also include a comparison of saving rates from demographically similar users who are connected to the user via social media applications.

In accordance with one aspect of the disclosure, a parent (e.g., a caregiver, guardian, or other authority figure) may provide a debit card to their child (e.g., caregivee or other subordinate), but wish to restricts use of the debit card in particular scenarios. Moreover, the parent may provide their child some other instrument or device that provides payment for the child's discretionary purchases. Some non-exhaustive examples of such instruments or devices are credit cards, person-to-person payment tools, debit cards, payments vehicles (such as an e-check) directly debiting against (e.g., withdrawing from) an account at a financial institution, and other mechanisms. In a caregiver-caregivee or parent-child relationship, the disclosed system grants the caregiver/parent the opportunity to approve a questionable transaction, in real-time, before the caregivee/child can complete the purchase at a point of sale 162 (e.g., a retail location or even an online shopping cart).

Figure 19:
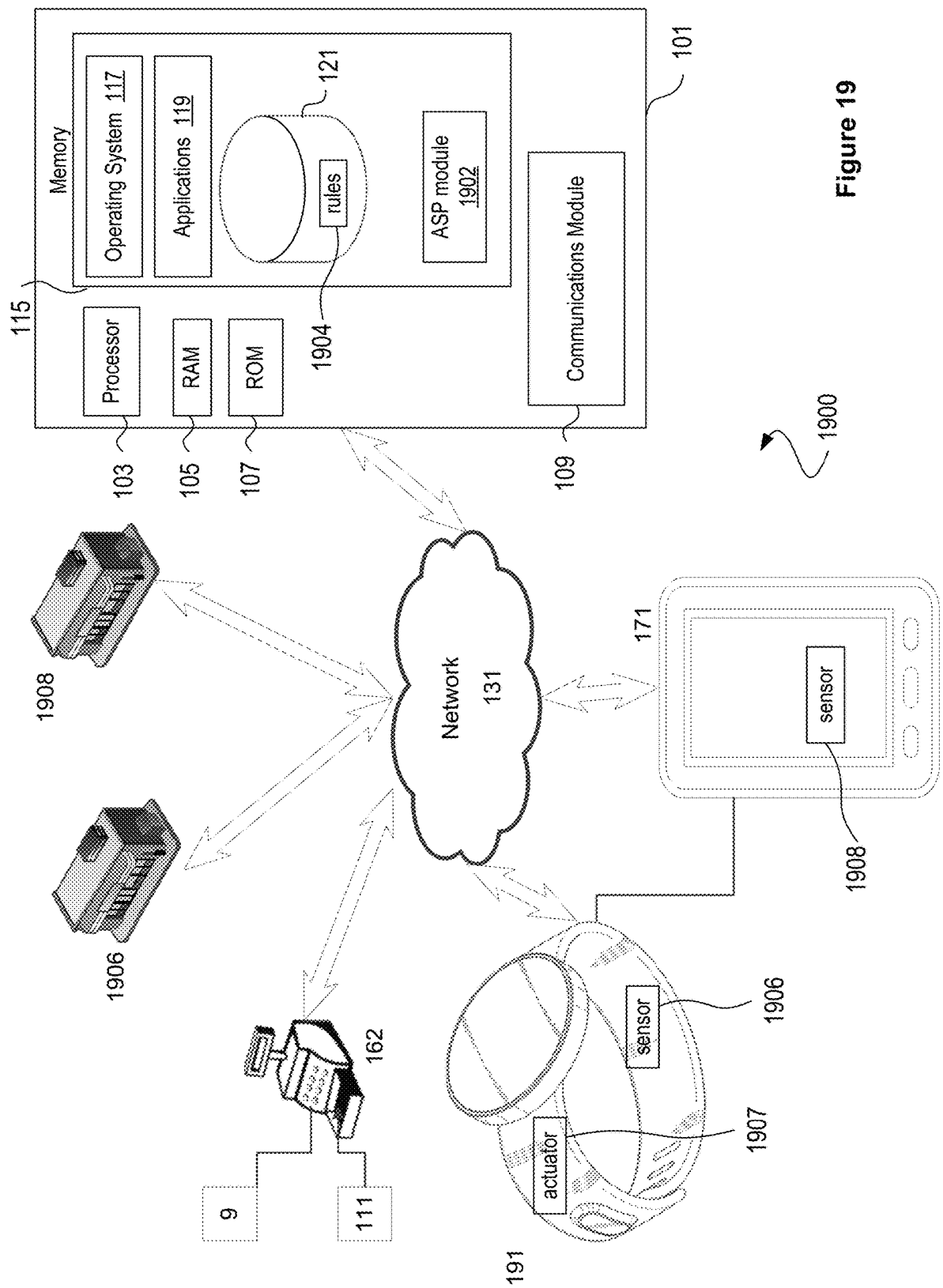
FIG. 19 shows an illustrative operating environment in which various aspects of the disclosure may be implemented.

In one embodiment, a dynamic, permissions-based networked system is disclosed to assist in controlling spending and to encourage savings. FIG. 19 illustrates one example of a networked environment in which a technological solution is implemented to address one or more aforementioned shortcomings in the industry. The networked system in FIG. 19 shows innovative technological features that allow a back-end server to identify which financial transactions require approval and which do not. For example, in one basic example, the system of FIG. 19 may require approval for purchases over an amount threshold. In a more complex example, the system of FIG. 19 may permit customization and tailoring of particular rules 1904 stored at a central server 101 to identify which transactions require approval from a caretaker or parent, and which do not require any parental approval.

Figure 26:
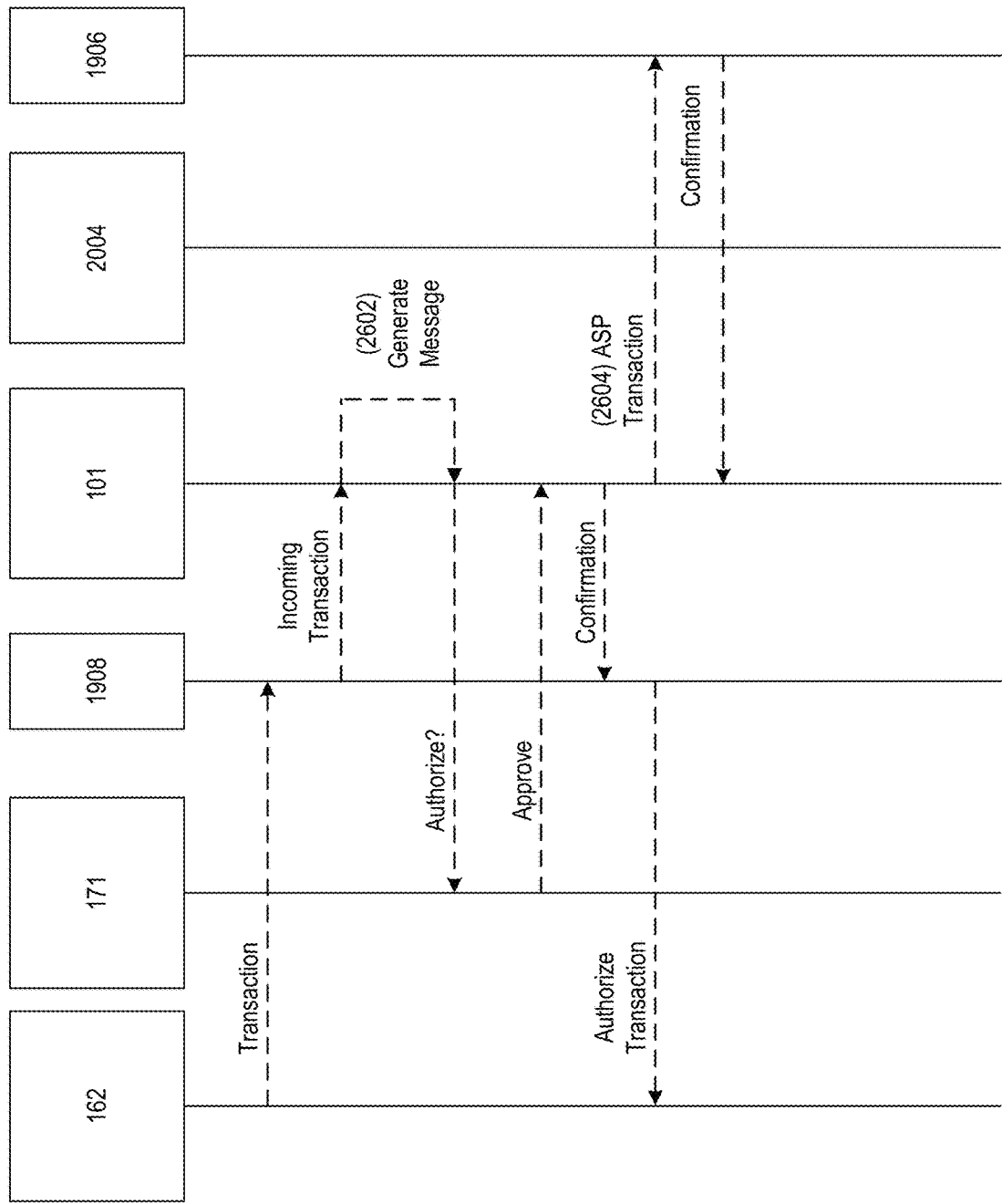
FIG. 26 illustrates interactions between components in a heterogeneous system in which a supervisory user manages real-time authorization or denial of electronic financial transactions requested by a junior user, including other aspects disclosed herein.

As depicted in FIG. 26, a child may use any debit card or other payment vehicle at a point of sale device 162. The transaction is submitted over a network 131 to a payment processor 1908 associated with the point of sale device 162. The payment processor 1908 could be affiliated with a financial institution or it may be affiliated with a payment vendor. In any event, as illustrated in FIG. 26, the payment processor 1908 sends the incoming transaction, which was received from the point of sale device 162, to a central server computer 101 for processing. In one example, the payment processor 1908 may forward the incoming transaction exactly as it received it from the point of sale device 162. As such, when the central server computer 101 would have access to exactly the same data fields in the transaction message as the payment processor 1908. As explained herein, the central server computer 101 includes, in some embodiments, various modules 1902, 2002, and memories 115, 121, 2104 to facilitate the function and operation of the novel system.

Moreover, the aforementioned approach has the added benefit of minimizing the need for the payment processor 1908 to modify its previous operation and functionality. In other words, in a heterogeneous network of payment processors 1908, 1906, and point of sale devices 162, 191, 171, requiring each node in the network to completely rewrite its programming code would be an onerous and technologically impractical requirement. Rather, the technological solution offered here is to make computer server 101 openly available for access via the network 131. Whenever computer server 101 receives an incoming transaction from a trusted node, such as payment processor 1908, it confirms the trusted status by confirming the IP address of the node and/or decrypting the payload of the incoming transaction using an encryption key. In any event, once the incoming transaction has arrived at the computer server 101, the computer-executable computer instructions at the computer server 101 analyze it.

The computer 101 (e.g., server farm 2102) accesses the data store 121 of rules 1904 to determine if any rule is associated with the same source account that is the source of payment for the transaction submitted at the point of sale device 162. As explained herein, the rules 1904 may be in the form of a lookup table, or other form of searchable data store, where each entry has associated with it a source identifier and other parameters. If the source identifier in any of the rules 1904 matches that of the incoming transaction, then the other parameters of the matched rule are further evaluated. For example, the data fields of the incoming transaction storing a merchant identifier ID, a location (e.g., GPS), dollar amount, date (e.g., day of week, month), and other fields (including one or more of those illustrated in FIG. 17) is evaluated against what, if anything, the matched rule or rules instructs about what value triggers one or more actions identified in the rule. FIG. 25 provides some illustrative pairings of parameters and actions that might be stored as rules in the data store 121. For example, if a child buys coffee from a known merchant ID for coffeehouses, then the rule 1904 may be setup to trigger the computer server 101 to generate a message (step 2602) to the parent's smartphone 171 requesting authorization for the child's purchase. Unlike the examples depicted in FIG. 22, FIG. 23, and FIG. 24, the point of sale device 162 does not asynchronously receive authorization from the payment processor 1908. Instead, the payment processor 1908 will not send an authorization approval message to the point of sale device 162 until it receives confirmation/approval from the central server 101 that the parent's device 171 has approved the transaction, as illustrated in FIG. 26.

Only after the payment processor 1908 receives an approval message from the central server 101 does the payment processor 1908 send an authorization approval to the point of sale device 162. The payment processor 1908 code is updated to include in serial (i.e., synchronous and not asynchronous) a call/request to the central server 101 before authorizing transactions. In some examples, if no authorization is required, such as if the user is not under supervision, then the central server 101 may nearly immediately reply back with an confirmation/approval message instead of generating a message, as in step 2602.

In addition, the system 1900 and its data store 121 of rules 1904 incorporates and is robustly designed automated savings programs. For example, a parent may identify greater automated savings for those transactions of its child at particular merchants. For example, a rule 1904 may state that when an incoming transaction is for a fast food merchant on a weekday, then the automated savings program module 1902 at server 101 automatically generates an automated savings program (ASP) transaction and sends it to the transaction processing system 1906 at another financial institution. The ASP transaction may comprise a debit transaction and a credit transaction instructing that financial institution to transfer a particular amount of funds from a checking account (or other source account) and into a savings account (or other destination account). See FIG. 23, step 2302. In another example, ASP module 1902 at the server 101 may generate message packets to pass to deposit applications and credit engines at system 1906. In short, using one or more novel features disclosed herein, a parent can store dynamic rules at data store 121 to encourage greater or normal savings levels by their child based on the plethora of parameters and variables described herein.

In addition to the aforementioned caregiver-caregivee relationships, the system may also use a peer-based approval/filtering/regulation system for securing approval—e.g., at particular stores or locations or for types of goods. For example, before a user purchases an item, her social media group of friends and colleagues might be alerted of her purchase and are allowed to recommend ways for her to save before she completes the purchase—e.g., when she goes to buy a new TV, friends that have recently bought TVs or are knowledgeable about TVs might help her find a better deal or provide her with tips before she finalizes her purchase—a different, yet useful form of encouraging savings. Besides encouraging saving of money, the particular rules may be used to encourage better behavior among adolescents (e.g., children, adolescents) and caregivees. The better behavior may be in the form of the types of things purchased, dates when purchased are made, amount of purchases, and may further the financial health of the caregivees. Additional features involving the financial health of a user are described herein.

In one embodiment in accordance with various aspects of the disclosure, a financial health tracking device is disclosed. Analogous to a fitness tracking device, described herein is a financial health tracking device worn, for example on the wrist of or carried by, a user. In one example, the financial health device may be embodied in a system for tracking financial health of a user, the system including: a smartwatch configured to be worn by the user, where the smartwatch includes a sensor and an actuator; a mobile device configured to detect behavioral activities of the user using a detection system installed on the mobile device; and a central server computer with an automated savings module, in network signal communication with the smartwatch and the mobile device; the automated savings module stores computer-executable instructions that, when executed by a processor of the central server computer, causes the central server computer to perform various steps. For example, the system may include the step of receiving an incoming transaction, from the mobile device, where the incoming transaction originated from the detection system of the mobile device detecting the behavioral activities of the user. The system may also include verifying authenticity of the incoming transaction. The system also includes identifying a rule in an automated savings table that matches criterion with the incoming transaction. The system may also include generating a new financial transaction including a debit transaction from a source account of the user for a monetary amount and a credit transaction to a savings account of the user for the monetary amount. The system may also include sending the new financial transaction to a payment processing system to complete the debit transaction and the credit transaction. The system may also include, upon confirmation of the completion of the debit transaction and the credit transaction, generating a notification to the smartwatch, where the notification causes the actuator of the smartwatch to vibrate. Of course, a system of one or more computers can be configured to perform the particular operations or actions by virtue of having software, firmware, hardware, or a combination of them installed on the system that in operation causes or cause the system to perform the actions. And one or more computer programs can be configured to perform particular operations or actions by virtue of including instructions that, when executed by data processing apparatus, cause the apparatus to perform the actions.

In one example, the graphical user interface (FIG. 27) on the aforementioned device displays different graphic elements with various metrics being collected, calculated, and transmitted. In one example, the financial health feature may encourage savings by requiring the user to save X number of dollars for indulgent real world activity—for example, if the user's device, such as a smartwatch or tablet, detects the user watching videos online, it tracks the number of minutes the user watches the videos, and the user is notified that X number of dollars were transferred into their savings from their other account as savings—i.e., punishment for the indulgence. Other examples could involve calorie intake, dessert consumption, Facebook screen time, and other examples. A few illustrative examples are described below.

For example, the system 1900 includes rules 1904 in the automated savings table stored in memory 115. A particular rule may state that when the incoming transaction has an amount of time field greater than one hour and a message identifier field indicating social media access time, then to cause the central server computer to perform the generating of the new financial transaction. In another example, the system may involve a smartwatch including an activity monitor. And a particular rule in the automated savings table may state that when the incoming transaction has a number of calories field greater than three hundred and the message identifier field indicating exercise activity, then to cause the central server computer to perform the generating of the new financial transaction. In yet another example, the system may be such that the detection system of the mobile device includes an image capture device. And a particular rule in the automated savings table indicates that when the incoming transaction has an amount of time field greater than thirty minutes and a message identifier field indicating video screen time, then to cause the central server computer to perform the generating of the new financial transaction. In finally another example, the system may be such that the detection system of the mobile device includes a location detection system. And a particular rule in the automated savings table indicates that when the incoming transaction has a location field equal to a fast food restaurant area and a message identifier field indicating diet restrictions, then to cause the central server computer to perform the generating of the new financial transaction. Implementations of the described techniques may include hardware, a method or process, or computer software on a computer-accessible medium.

Figure 28:
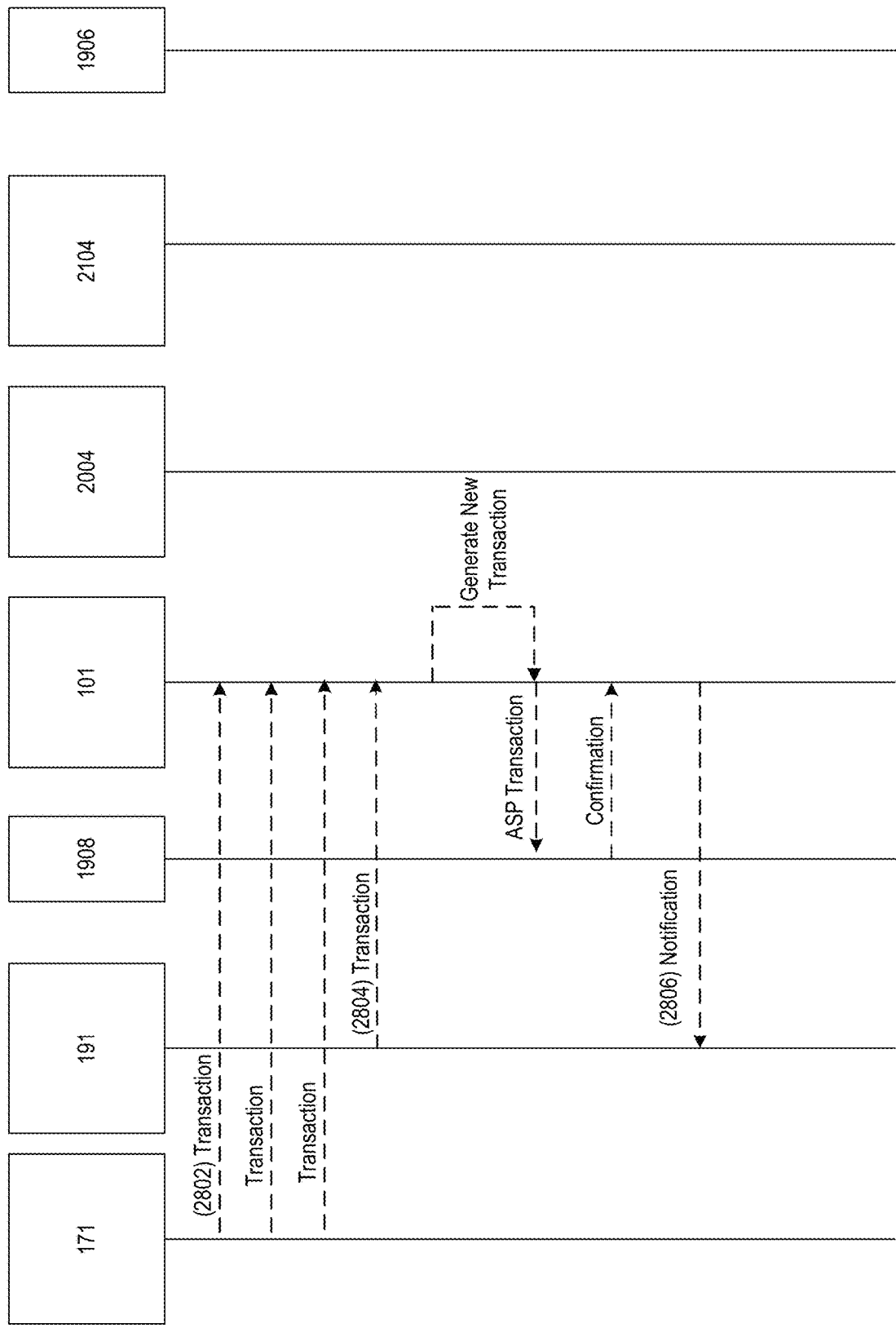
FIG. 28 illustrates interactions between components in a networked system in which a user receives notifications related to an automated savings program, including other aspects disclosed herein.

Referring to FIG. 28, in step 2802, a transaction may originate from device 171. The device 171 may be a tablet or other electronic computing device configured to collect behavioral activities of the user and perform novel calculations with those values. For example, perhaps a user's biometrics might show telltale signs of impulsive purchases (e.g., heart rate and neurological changes when making an excessive purchase) and the smartwatch might alert the users to these just before the point of purchase. In another example, the central server computer 101 may receive transactions from a smartwatch 191 in step 2804.

Figure 22:
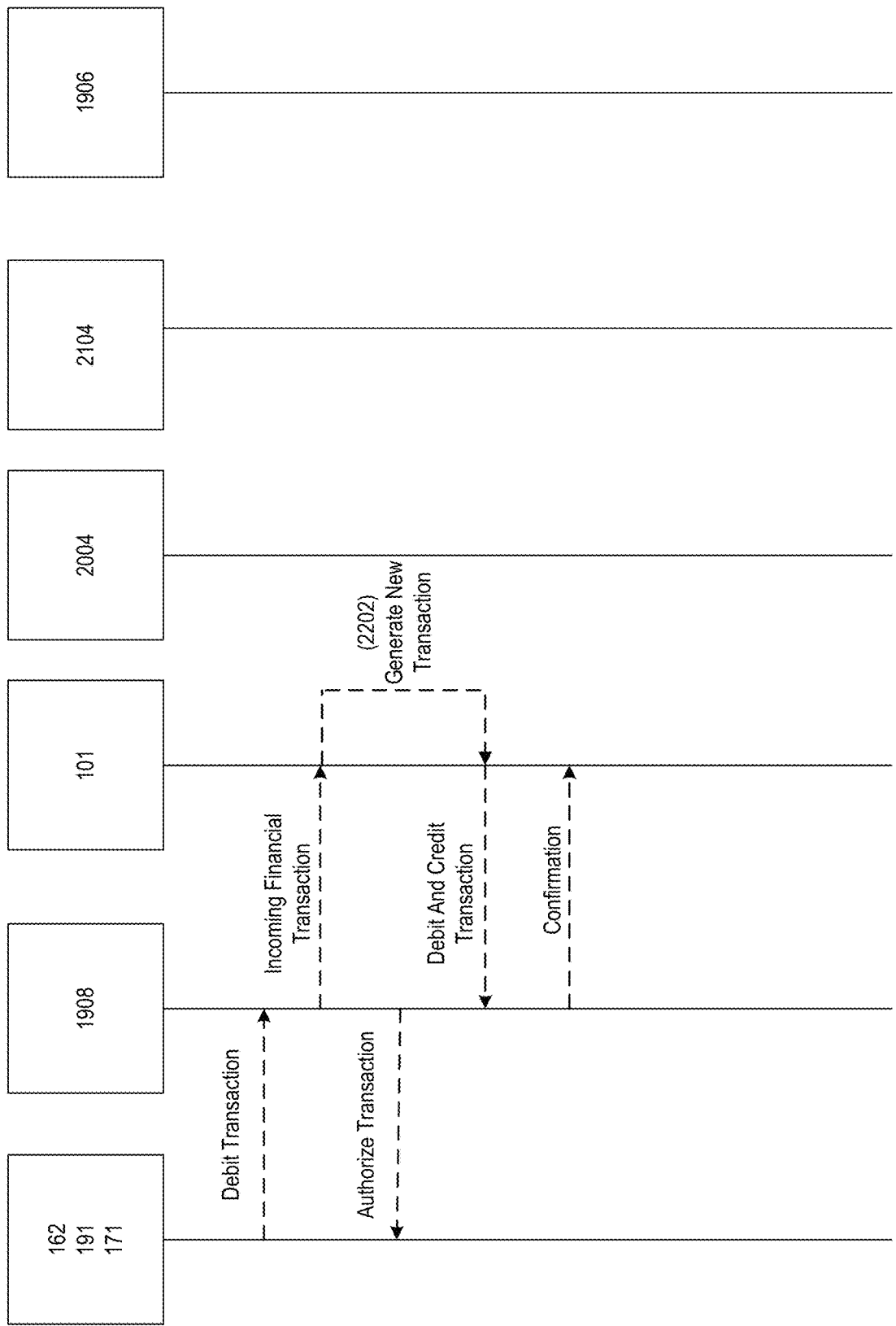
FIG. 22 illustrates interactions between components in a homogenous system where an automated savings program is provided for regular debit card transactions.
Figure 23:
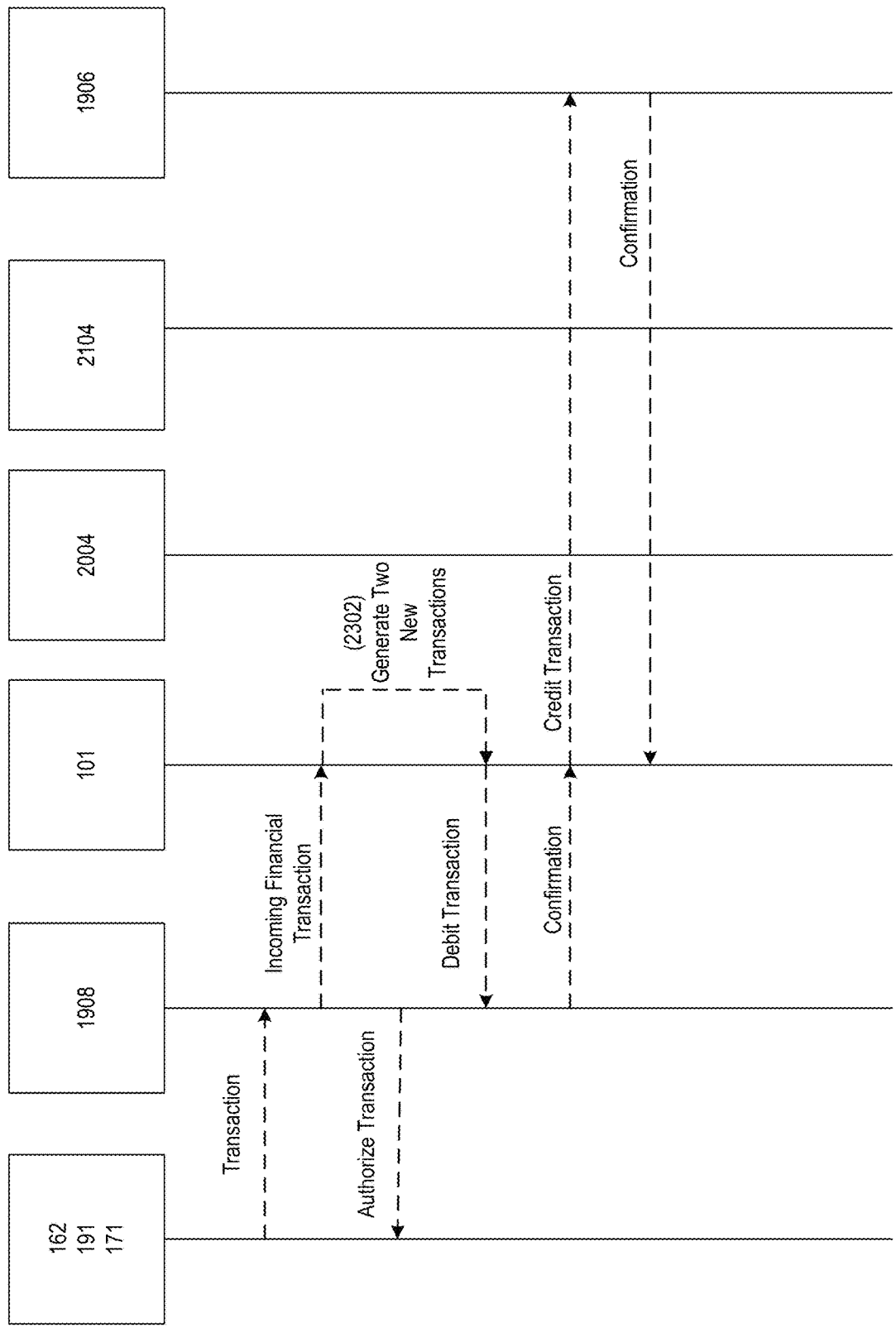
FIG. 23 illustrates interactions between components in a heterogeneous system where an automated savings program is provided for electronic financial transactions.

The aforementioned transactions of step 2802 and step 2804, in contrast to the incoming financial transactions described in FIG. 22 and FIG. 23, is formatted with fields to accommodate behavioral activities to further a financial health smartwatch embodiment. The transaction message type, like the query message type from FIG. 24, includes data fields that allow for the transfer of information from the computing device 171 to the central server computer 101. Step 2806 in FIG. 28 illustrates a notification being sent from the central server 101 to a user's smartwatch device 191. As illustrated in FIG. 19, the smartwatch 191 may include a sensor 1906 and actuator 1907.

Figure 27:
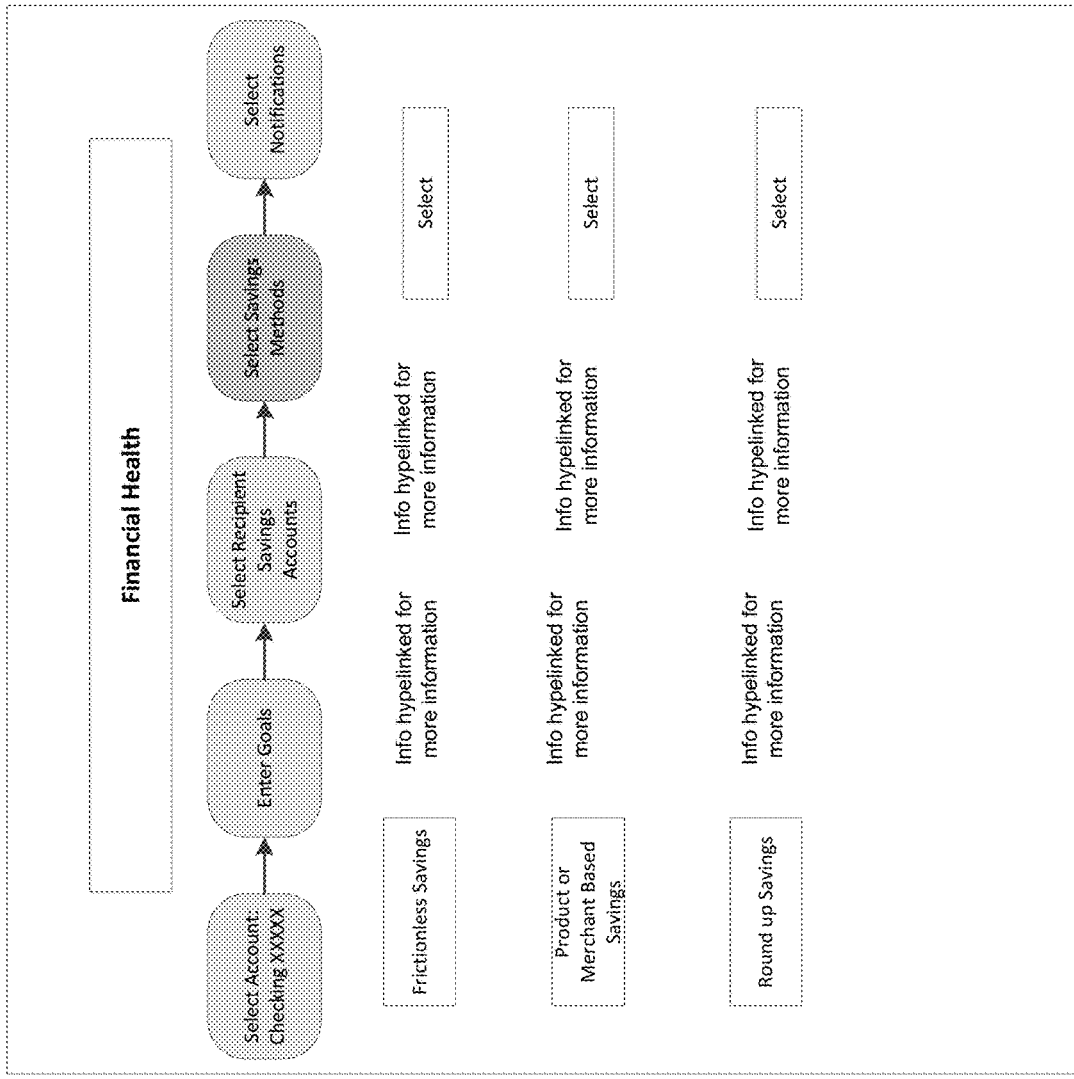
FIG. 27 depicts a graphic user interface of an illustrative smartwatch device in accordance with aspects of the disclosure.

Although FIG. 19 illustrates a smartwatch 191, the disclosure contemplates other user devices capable of receiving a notification of the type described herein. For example, an augmented reality headset or virtual reality glasses are contemplated in FIG. 19, although not illustrated. In alternative embodiments the form factor may be other than a smartwatch—e.g., a GUI on a mobile phone, a virtual reality (VR) headset, an augmented reality (AR) headset that integrates the image with the real world, etc. FIG. 27 is an illustrative display on a computing device, such as a smartwatch 191, implementing one or more of the features disclosed herein. The disclosure contemplates one or more metrics to be displayed on the end user visual display, e.g., of a smartwatch or other device.

FIG. 19 shows an illustrative operating environment in which various aspects of the disclosure may be implemented generally relating to an innovative network architecture that enables the seamless connectivity of an automated savings program to an existing network of transactional systems. The transactional system may comprise a plurality of homogenous computer systems belonging to a single entity. For example, a single financial institution may communicatively couple a network of transactional systems comprising a debit network. These transactional systems assist in performing transactions, such as debit transactions, associated with users of the financial institution. The innovative network architecture seamlessly connects to the transactional system to permit universal sign-on and/or enrollment to an automatic savings program. The connectivity is seamless, in some embodiments, because an existing transactional system might not natively include an automatic savings program, but the innovative network architecture enables a computer server configured with computer-executable instructions for an automatic savings program to interface with the existing transactional system. In one embodiment, the interface may be through a web service that integrates into an existing network of transactional system. In another embodiment, the interface may be through overloading of method calls of objects in an existing transactional system. Other methods of integration with existing heterogeneous computer systems are also possible and contemplated by this disclosure.

In another example, a network of transactional systems comprising an existing credit payment network may communicatively couple with a computer server configured to implement an automatic savings program. The transactional systems assists in performing credit transactions associated with users of the financial institution. The compute server configured to implement an automatic savings program seamlessly connects to the transactional system to permit universal sign-on and/or enrollment to an automatic savings program. See step 2202 in FIG. 22. For example, when a user pays at a retail point-of-sale (POS) device for a $77.25 purchase using a credit card, then an additional 75 cents will be charged interest-free to her credit card, and that 75 cents is sent to her savings. Execution of such a transaction includes multiple steps as elaborated below.

In accordance with various aspects of the disclosure, the monetary amount automatically transferred from an account holder's source account to a recipient account in the form of savings, may be calculated based on one or more factors. For example, under an increasing approach a transaction amount may be increased to the next highest integer value. Meanwhile, under another approach, the transferred savings amount may be calculated by decreasing the transaction amount to the previous lowest integer value if the transaction is not already an integer dollar amount. If the transaction amount is already an integer value, under alternative embodiments in accordance with aspects of the disclosure, the transaction amount may still be decreased to the previous lowest integer value, or alternatively, remain unchanged. The aforementioned approach of decreasing the transaction amount may be referenced in this disclosure as "the decreasing approach." The decreasing approach may be useful in the case of a savings program based on credit card transactions. In another example, the savings amount may be a fixed amount (e.g., $1, $0.50, $5, and the like) per transaction. In yet another example, the total savings amount for a period of time (e.g., a year) may be limited to a predefined maximum amount.

In an alternative embodiment, an account holder may customize (e.g., through an online graphical user interface) the specifics of its automated savings program. For example, the user may configure, at account enrollment and thereafter, one or more various features of the automated savings account discussed herein including, but not limited to, the following: the source account(s), the recipient account(s), the savings scheme (round-up, percentage amount, predetermined dollar amount, and the like), the aggressiveness of the savings scheme (e.g., in the case of an increasing approach, the amount of transferred savings), charitable savings, payment of exiting loans, or savings for a specified purchase item. For example, a user may designate the increasing approach to use the next highest $5 denomination. As such, the amount of transferred savings amount is greater. Likewise, the aggressiveness of the transferred savings amount may be controlled for other types of monetary amounts (e.g., savings amounts) disclosed herein and contemplated by one of skill in the art after review of the entirety disclosed herein. Such an embodiment provides customization of the savings program for the user account. Such a computer system may send information about user preferences/settings are used by an incentive engine and/or provided to a parameter-based rules engine (e.g., an incentive engine that accepts different parameters to customize the matching/savings aspects for a user in accordance with various aspects of the disclosure).

While prior art credit card systems existed, but none included a native automatic savings program such as described herein. Moreover, by implementing an automatic savings program as seamlessly integrated with a network of transactional systems, there are numerous technological benefits previously unrealized by prior art transaction systems. While the aforementioned example refers to a credit payment network, the disclosure is not so limited. Similarly, a financial institution may communicatively couple a network of transactional systems comprising a debit network, a credit network, an online billpay network, a person-to-person payment network, a cypto-currency network, and/or any other payment network.

Figure 20:
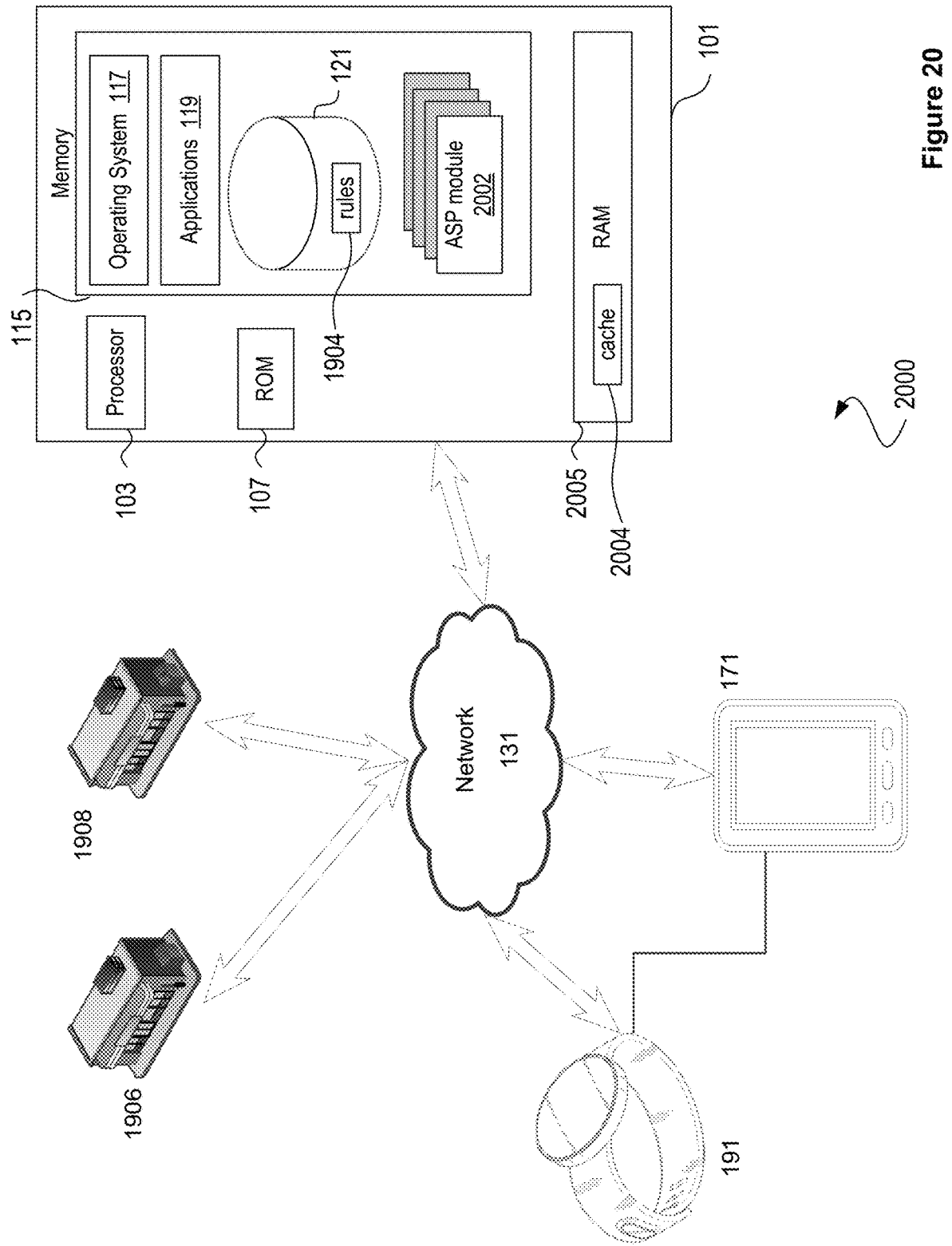
FIG. 20 shows an illustrative operating environment incorporating an enhanced cache memory in which various aspects of the disclosure may be implemented.

Referring to FIG. 20, in other embodiments, the transactional system 2000 may comprise heterogeneous computer systems 1906, 1908 belonging to a plurality of entities. The seamless connectivity of central server computer 101 permits universal sign-on and/or enrollment to an automatic savings program, as illustrated in FIG. 23. The connectivity is seamless, in some embodiments, because an existing transactional system might not natively include an automatic savings program, but the innovative network architecture enables a computer server configured with an automatic savings program to interface with the existing transactional system. In one embodiment, the interface may be through a web service that integrates into an existing network of transactional system. In another embodiment, the interface may be through overloading of method calls of objects in an existing transactional system.

Figure 24:
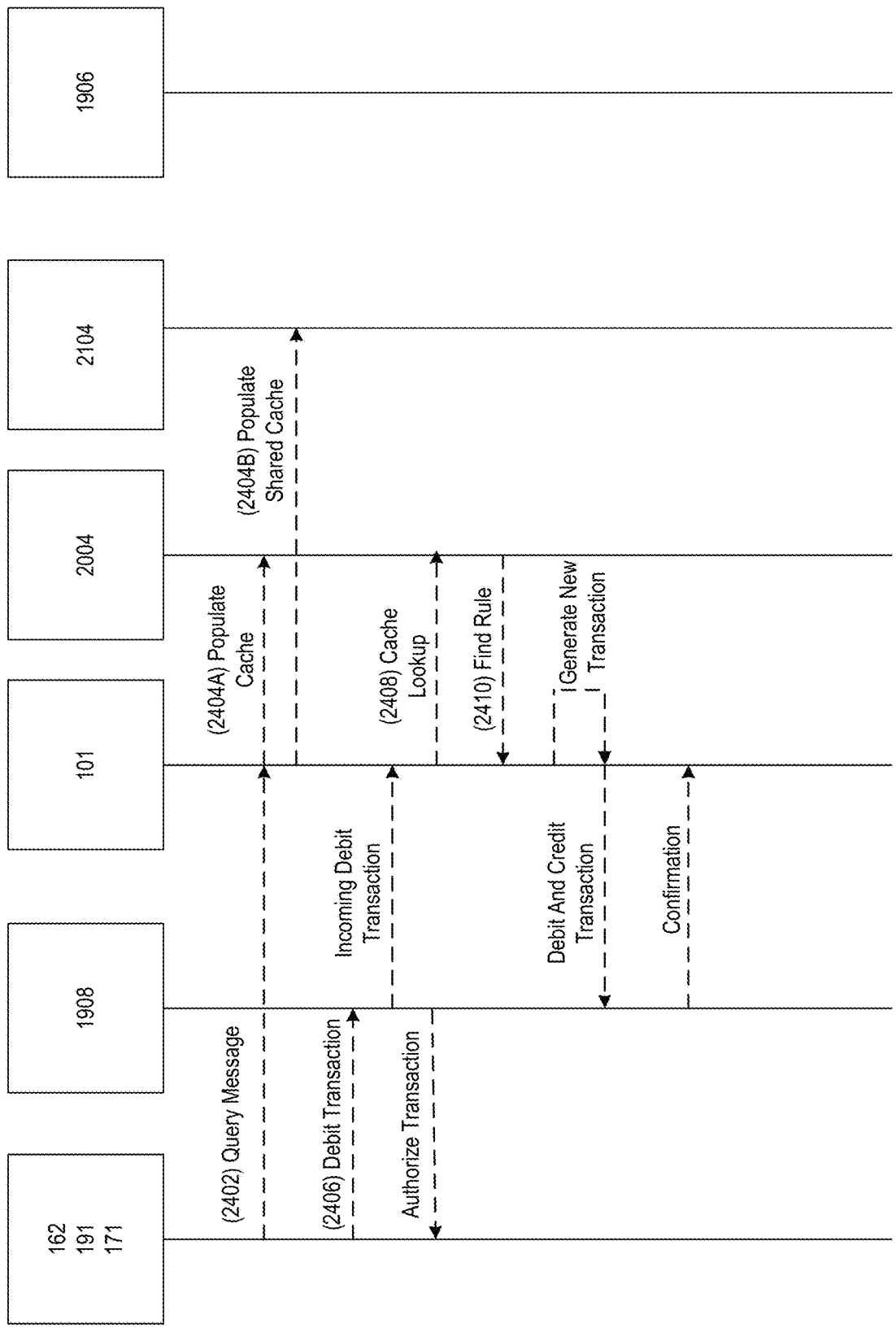
FIG. 24 illustrates interactions between components in a networked system where an automated savings program with an enhanced cache memory is provided for electronic financial transactions, including person-to-person transactions.

Referring to FIG. 20, the computing device 101 may operate in a networked environment supporting connections to one or more remote computing devices. In particular, FIG. 20 shows an illustrative operating environment incorporating an enhanced cache memory 2004 in which various aspects of the disclosure may be implemented. A plurality of ASP modules 2002 may access the cache 2004 in memory to obtain faster access to particular rules 1904 that were originally stored in a data store 121. FIG. 24 illustrates that step 2404A populates a basic cache, and step 20408B populates a shared cache located at electronic component 2104. At least one benefit of a cache is faster access to the data to be requested as a result of a transaction 2406. For example a query message 2402 may be sent to the central server computer 101 to trigger a cache 2004, 2106 update with the relevant rules from the automatic savings program (ASP) table.

Figure 21:
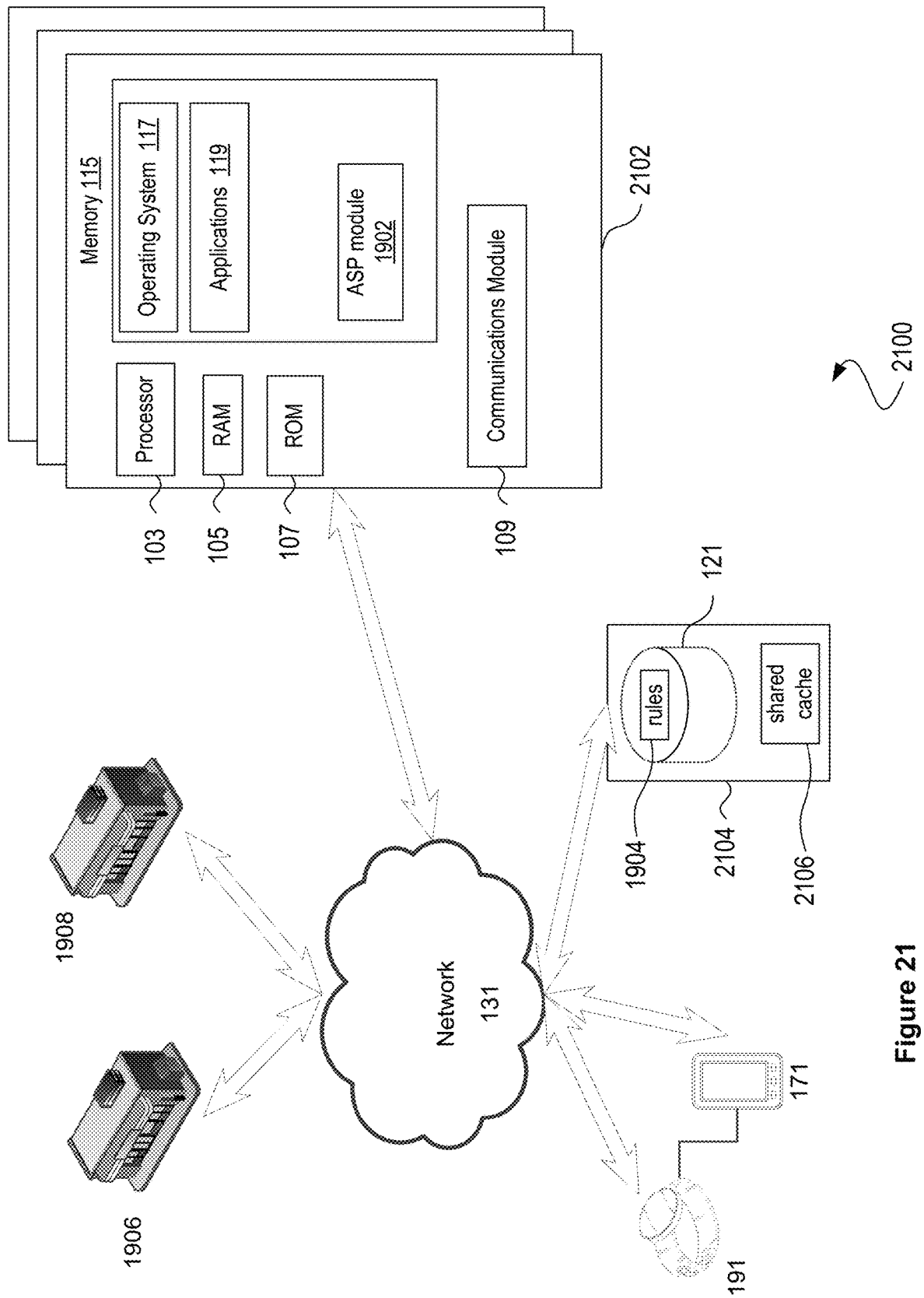
FIG. 21 shows an illustrative operating environment incorporating a shared cache memory coupled to a central server farm in which various aspects of the disclosure may be implemented.

Meanwhile in FIG. 21, a server farm 2102 is illustrated to distribute the load across a plurality of server computers. To that end, a separately coupled shared memory 2104 may store a shared cache 2106 that is accessible to the server farm 2102. At least one technological benefit of the configuration of FIG. 21 is that multiple server computers may benefit from the shared cache.

Also, one of ordinary skill in the art after review of the present disclosure will appreciate that various features and aspects of the disclosure may be combined with other features and aspects disclosed herein. For example, various aspects of the numerous examples provided with regards to debit card use may be applied to embodiments regarding credit card use. Likewise the different matching/bonus features listed herein may be combined or substituted for other matching/bonus features to fully appreciate the embodiments contemplated by the entirety of the disclosure. Additionally, different saving/notification features may be combined or substituted for other savings/notification features to fully appreciate the embodiments contemplated by the entirety of the disclosure.

We claim:

1. A system for tracking financial health of a user, the system comprising:
a wearable electronic device configured to be worn on the user, wherein the wearable electronic device comprises a sensor and an actuator;
a mobile device configured to detect behavioral activities of the user using a detection system installed on the mobile device; and
a central server computer with an automated savings module, in network signal communication with the wearable electronic device and the mobile device;
the automated savings module stores computer-executable instructions that, when executed by a processor of the central server computer, causes the central server computer to perform steps comprising:
receiving an incoming transaction, from the mobile device, wherein the incoming transaction originated from the detection system of the mobile device detecting the behavioral activities of the user;
verifying authenticity of the incoming transaction;
identifying a rule in an automated savings table that matches criterion with the incoming transaction;
generating a new financial transaction comprising a debit transaction from a source account of the user for a monetary amount and a credit transaction to a savings account of the user for the monetary amount;
sending the new financial transaction to a payment processing system to complete the debit transaction and the credit transaction; and
upon confirmation of the completion of the debit transaction and the credit transaction, generating a notification, wherein the notification, when received by the wearable electronic device, causes the actuator of the wearable electronic device to vibrate, wherein the incoming transaction is a behavioral activity message type comprising fields for message identifier, amount of time, user identity, and date.

2. The system of claim 1, wherein the sensor of the wearable electronic device comprise a location detection system and an image capture device.

3. The system of claim 1, wherein the rule in the automated savings table indicates that when the incoming transaction has an amount of time field greater than one hour and a message identifier field indicating social media access time, then causing the central server computer to perform the generating of the new financial transaction.

4. The system of claim 1, wherein the wearable electronic device further comprises an activity monitor, and wherein the rule in the automated savings table indicates that when the incoming transaction has a number of calories field greater than three hundred and the message identifier field indicating exercise activity, then causing the central server computer to perform the generating of the new financial transaction.

5. The system of claim 1, wherein the detection system of the mobile device comprises an image capture device, wherein the rule in the automated savings table indicates that when the incoming transaction has an amount of time field greater than thirty minutes and a message identifier field indicating video screen time, then causing the central server computer to perform the generating of the new financial transaction.

6. The system of claim 1, wherein the detection system of the mobile device comprises a location detection system, wherein the rule in the automated savings table indicates that when the incoming transaction has a location field equal to a fast food restaurant area and a message identifier field indicating diet restrictions, then causing the central server computer to perform the generating of the new financial transaction.

7. The system of claim 1, wherein the verifying of the authenticity of the incoming transaction includes confirming that a source of the incoming transaction corresponds to an authorized device.

8. The system of claim 1, wherein the verifying authenticity of the incoming transaction further comprises:
parsing the incoming transaction into a plurality of fields; and
matching an IP address field of the incoming transaction to an IP address in the automated savings table.

9. The system of claim 1, wherein the verifying authenticity of the incoming transaction further comprises:
parsing the incoming transaction into a plurality of fields;
extracting an encryption key field of the incoming transaction to obtain an encryption key; and
decrypting at least one field of the plurality of fields using the encryption key.

10. A method comprising:
receiving, by a processor, an incoming transaction, from a mobile device of a user, wherein the incoming transaction originated from a detection system of the mobile device detecting behavioral activities of the user;
identifying, by the processor, a rule in an automated savings table that matches criterion with the incoming transaction;
generating, by the processor, a new financial transaction comprising a debit transaction from a source account of the user for a monetary amount and a credit transaction to a savings account of the user for the monetary amount;
sending, by the processor, the new financial transaction to a payment processing system to complete the debit transaction and the credit transaction; and
upon confirmation of the completion of the debit transaction and the credit transaction, generating, by the processor, a notification, wherein the notification, when received by a wearable electronic device, causes an actuator of the wearable electronic device to vibrate, wherein the incoming transaction is a behavioral activity message type comprising fields for message identifier, amount of time, user identity, and date.

11. The method of claim 10, wherein a sensor of the wearable electronic device comprise a location detection system and an image capture device.

12. The method of claim 10, wherein the rule in the automated savings table indicates that when the incoming transaction has an amount of time field greater than thirty minutes and a message identifier field indicating social media access time, then causing the processor to perform the generating of the new financial transaction.

13. The method of claim 10, further comprising:
verifying, by the processor, authenticity of the incoming transaction by confirming that a source of the incoming transaction corresponds to an authorized device.

14. The method of claim 10, further comprising:
verifying, by the processor, authenticity of the incoming transaction by at least:
parsing the incoming transaction into a plurality of fields; and
matching an IP address field of the incoming transaction to an IP address in the automated savings table.

15. A non-transitory computer-readable medium storing computer-executable instructions that, when executed by a processor, causes a computer system to:
receiving, by the processor, an incoming transaction about a user, wherein the incoming transaction originated from a detection system of a mobile device detecting behavioral activities of the user;
identifying, by the processor, a rule in an automated savings table that matches criterion with the incoming transaction;
generating, by the processor, a new financial transaction comprising a debit transaction from a source account of the user for a monetary amount and a credit transaction to a savings account of the user for the monetary amount;
sending, by the processor, the new financial transaction to a payment processing system to complete the debit transaction and the credit transaction; and
upon confirmation of the completion of the debit transaction and the credit transaction, generating, by the processor, a notification to a wearable electronic device of the user, wherein the notification causes an actuator of the wearable electronic device to vibrate, wherein the wearable electronic device further comprises an activity monitor, and wherein the rule in the automated savings table indicates that when the incoming transaction has a number of calories field greater than three hundred and a message identifier field indicating exercise activity, then causing the processor to perform the generating of the new financial transaction.

16. The non-transitory computer-readable medium of claim 15, wherein the rule in the automated savings table indicates that when the incoming transaction has an amount of time field greater than two hours and a message identifier field indicating social media access time, then causing the processor to perform the generating of the new financial transaction.

17. The non-transitory computer-readable medium of claim 15, wherein the detection system of the mobile device comprises an image capture device, wherein the rule in the automated savings table indicates that when the incoming transaction has an amount of time field greater than thirty minutes and a message identifier field indicating video screen time, then causing the processor to perform the generating of the new financial transaction.

* * * * *